(12) United States Patent
Lemme et al.

(10) Patent No.: US 8,147,773 B2
(45) Date of Patent: Apr. 3, 2012

(54) METHOD AND APPARATUS FOR MODIFYING PRESSURE WITHIN A FLUID DISPENSER

(75) Inventors: Charles D. Lemme, Tucson, AZ (US); Vincent R. Rizzo, Jr., Tucson, AZ (US); Bobbi Druyor-Sanchez, Mesa, AZ (US); Anthony Ford, Tucson, AZ (US); Bronwen Heilman, Tucson, AZ (US); Darin McDaniel, Tucson, AZ (US); Brian McGraw, Tucson, AZ (US); Stephen Mead, Bradenton, FL (US); William Richards, Tucson, AZ (US); Wayne Showalter, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 13/050,707

(22) Filed: Mar. 17, 2011

(65) Prior Publication Data
US 2011/0168744 A1 Jul. 14, 2011

Related U.S. Application Data

(60) Continuation of application No. 10/913,932, filed on Aug. 6, 2004, now abandoned, which is a continuation-in-part of application No. 10/060,602, filed on Jan. 30, 2002, now abandoned, which is a continuation-in-part of application No. 09/896,649, filed on Jun. 29, 2001, now Pat. No. 6,945,128, which is a continuation of application No. 09/483,218, filed on Jan. 14, 2000, now Pat. No. 6,416,713, which is a division of application No. 08/995,052, filed on Dec. 19, 1997, now Pat. No. 6,045,759, which is a continuation-in-part of application No. 08/909,335, filed on Aug. 11, 1997, now Pat. No. 6,093,574.

(51) Int. Cl.
*B01L 3/02* (2006.01)

(52) U.S. Cl. ........ 422/501; 422/521; 422/527; 422/537; 422/538; 73/863.32; 73/864; 73/864.01; 73/864.03; 73/864.11; 73/864.13; 73/864.15; 73/864.16

(58) Field of Classification Search .................. 422/501, 422/537, 538, 542, 546, 521, 527; 73/863.32, 73/864, 864.01, 864.03, 864.11, 864.13, 73/864.15, 864.16
See application file for complete search history.

(56) References Cited

U.S. PATENT DOCUMENTS 2,234,079 A 3/1941 Miller
(Continued)

FOREIGN PATENT DOCUMENTS

FR 2 541 244 8/1984
(Continued)

OTHER PUBLICATIONS

International Search Report, Application No. PCT/US98/16604 dated Aug. 11, 1998.
(Continued)

*Primary Examiner* — Brian R Gordon
(74) *Attorney, Agent, or Firm* — Hayes Soloway P.C.; Huw R. Jones, Esq.

(57) ABSTRACT

A fluid dispenser useful in automated biological reaction systems comprising a barrel having a reservoir chamber, the barrel having an upper portion and a lower portion, a cap located on top of the upper portion of the barrel and connected to the reservoir chamber, the cap having an external surface with at least one hole therethrough, a valve comprising a biasing member and a hole sealer, the valve being located in the hole in the cap at the point where a downward force is applied against the cap, a coupler having a dispense chamber, the coupler being coaxial with the barrel and wherein the barrel lower portion moves into the dispense chamber during dispensing of fluid, and a vent located between the cap and the reservoir chamber, the vent including a vent opening and a vent material composed of oliophobic material.

16 Claims, 50 Drawing Sheets

U.S. PATENT DOCUMENTS

| | | |
|---|---|---|
| 3,650,437 A | 3/1972 | Binnings et al. .............. 222/136 |
| 3,695,281 A | 10/1972 | Leon .................................. 137/1 |
| 3,726,442 A | 4/1973 | Davidson et al. |
| 3,854,703 A | 12/1974 | Gibbs et al. ...................... 259/11 |
| 4,126,558 A | 11/1978 | Luceyk |
| 4,298,358 A | 11/1981 | Ruschke |
| 4,362,977 A | 12/1982 | Evans et al. |
| 4,455,280 A | 6/1984 | Shinohara et al. .............. 422/63 |
| 4,964,544 A | 10/1990 | Hanna et al. .................. 222/181 |
| 4,971,913 A | 11/1990 | Manabe et al. ................. 436/55 |
| 5,232,664 A | 8/1993 | Krawzak et al. ................ 422/64 |
| 5,289,385 A | 2/1994 | Grandone |
| 5,314,825 A | 5/1994 | Weyrauch et al. .............. 436/43 |
| 5,316,726 A | 5/1994 | Babson et al. .................. 422/65 |
| 5,348,705 A | 9/1994 | Koreyasu et al. |
| 5,373,972 A | 12/1994 | Bystrom et al. |
| 5,417,356 A | 5/1995 | Franklin et al. |
| 5,425,918 A | 6/1995 | Healey et al. ................... 422/64 |
| 5,428,470 A | 6/1995 | Labriola, II .................... 359/119 |
| 5,431,309 A | 7/1995 | Ophardt ...................... 222/181.3 |
| 5,439,646 A | 8/1995 | Tanimizu et al. ............... 422/64 |
| 5,439,649 A | 8/1995 | Tseung et al. ................... 422/99 |
| 5,443,791 A | 8/1995 | Cathcart et al. |
| 5,445,288 A | 8/1995 | Banks ............................. 222/95 |
| 5,446,652 A | 8/1995 | Peterson et al. .............. 364/578 |
| 5,468,388 A | 11/1995 | Goddard et al. ......... 210/321.75 |
| 5,474,541 A | 12/1995 | Ritsky et al. .................. 604/213 |
| 5,474,744 A | 12/1995 | Lerch ............................ 422/100 |
| 5,507,417 A | 4/1996 | Webb |
| 5,573,727 A | 11/1996 | Keefe et al. |
| 5,595,326 A | 1/1997 | Bougamont et al. ........ 222/321.7 |
| 5,595,707 A | 1/1997 | Copeland et al. ................ 422/64 |
| 5,650,327 A | 7/1997 | Copeland et al. ................ 436/46 |
| 5,654,199 A | 8/1997 | Copeland et al. |
| 5,654,200 A | 8/1997 | Copeland et al. ............... 436/46 |
| 5,687,882 A | 11/1997 | Mueller |
| 5,695,718 A | 12/1997 | Imai et al. ....................... 422/62 |
| 5,779,674 A | 7/1998 | Ford .............................. 422/103 |
| 5,860,456 A | 1/1999 | Bydlon et al. |
| 5,961,492 A | 10/1999 | Kriesel et al. |
| 6,045,759 A | 4/2000 | Ford et al. |
| 6,093,574 A | 7/2000 | Druyor-Sanchez et al. |
| 6,192,945 B1 | 2/2001 | Ford et al. ......................... 141/2 |
| 6,199,766 B1 | 3/2001 | Fox et al. .......................... 239/3 |
| 6,245,041 B1 | 6/2001 | Kriesel ......................... 604/131 |
| 6,416,713 B1 | 7/2002 | Ford et al. ........................ 422/63 |
| 6,623,631 B1 | 9/2003 | Graus et al. ................... 210/120 |

FOREIGN PATENT DOCUMENTS

| | | |
|---|---|---|
| SU | 777440 | 12/1980 |
| WO | WO 2005/000731 | 1/1995 |
| WO | WO 92/04004 | 3/2002 |

OTHER PUBLICATIONS

"Vernay Umbrella Check Valves", Vernay Laboratories, Inc., © 1995.

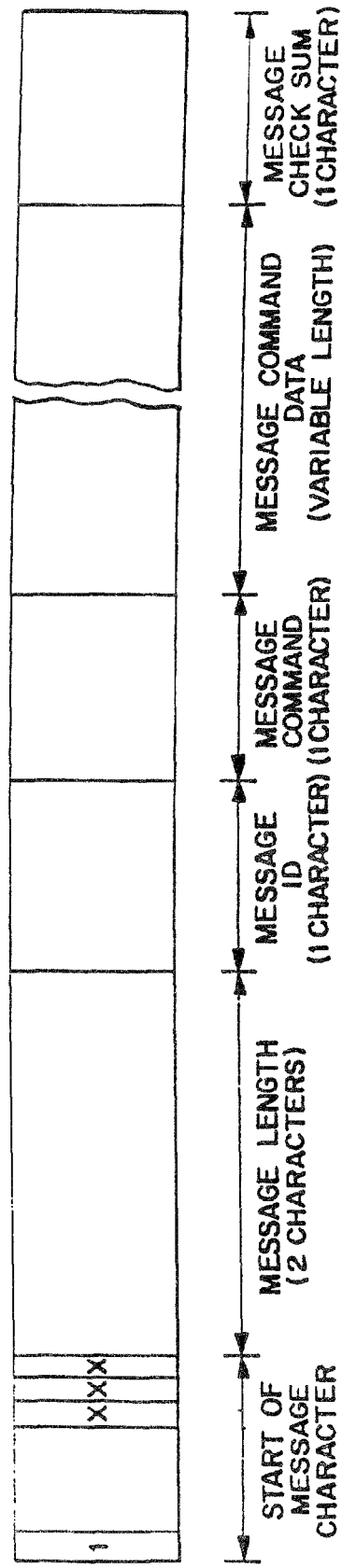

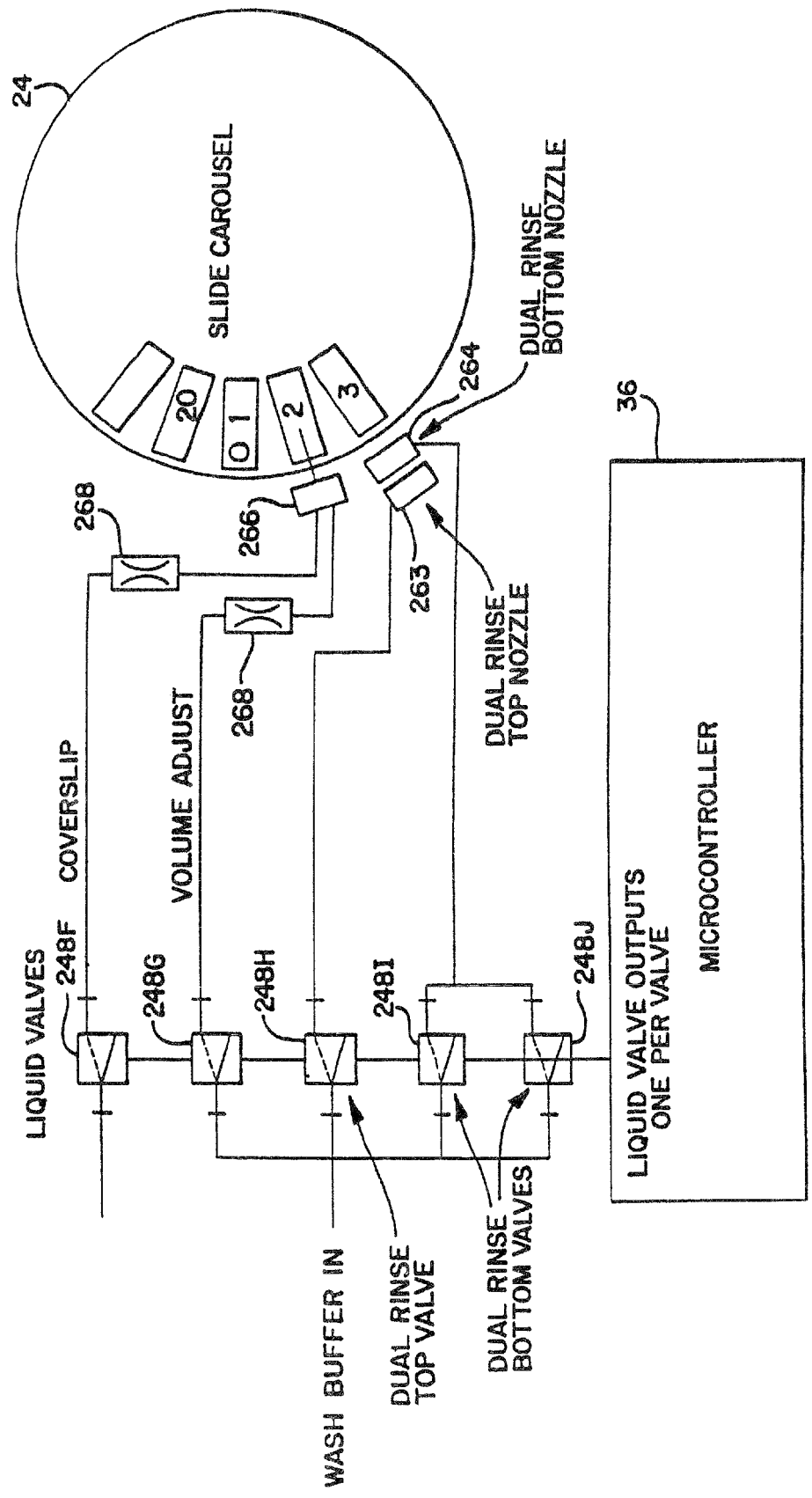

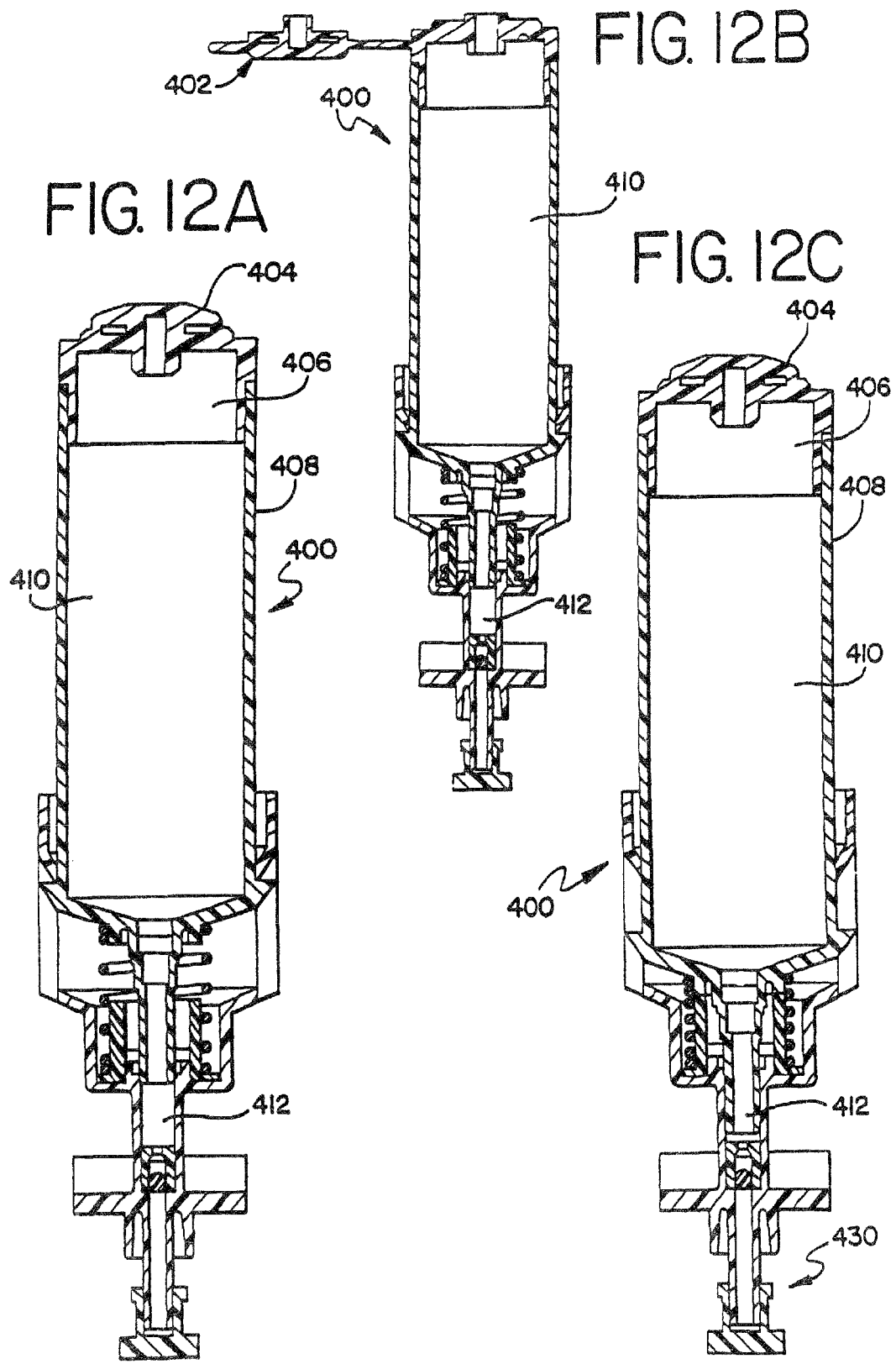

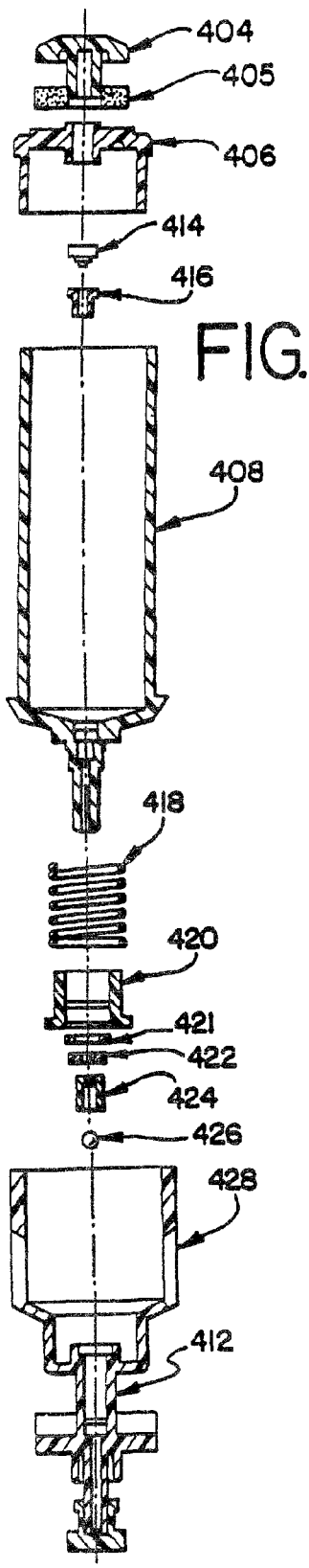
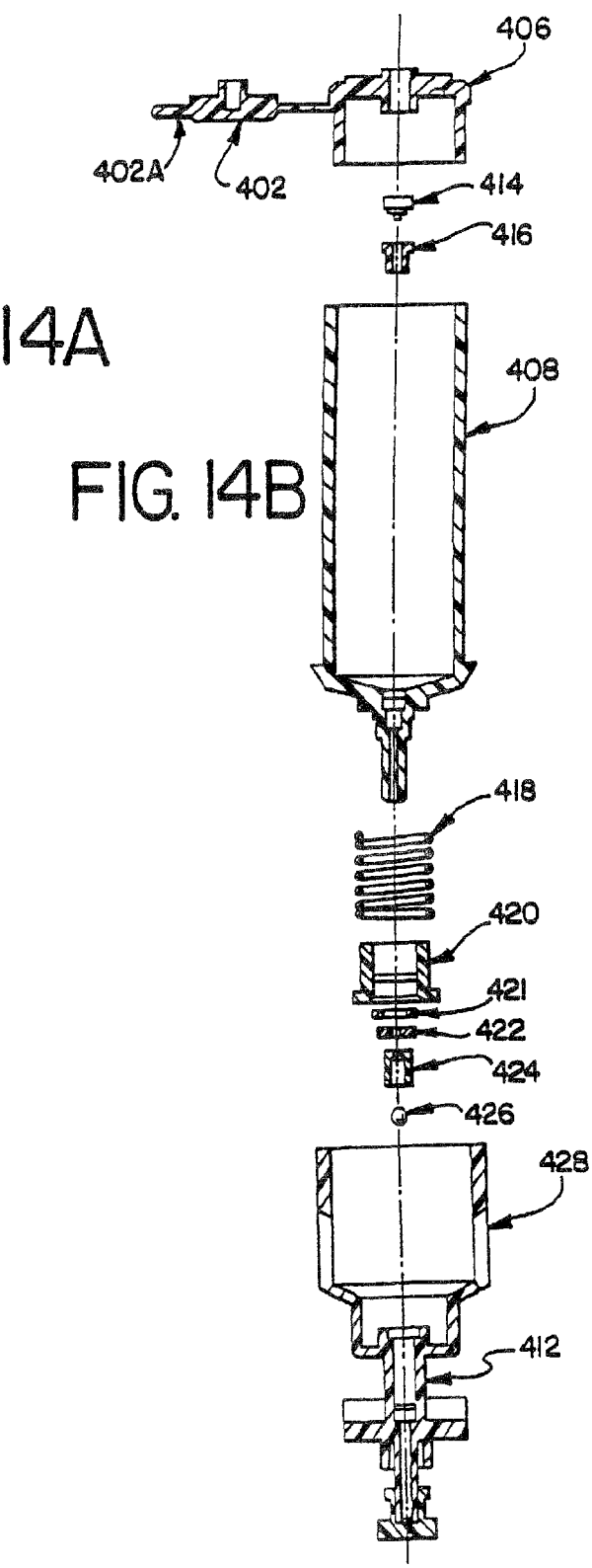
FIG. 14A
FIG. 14B

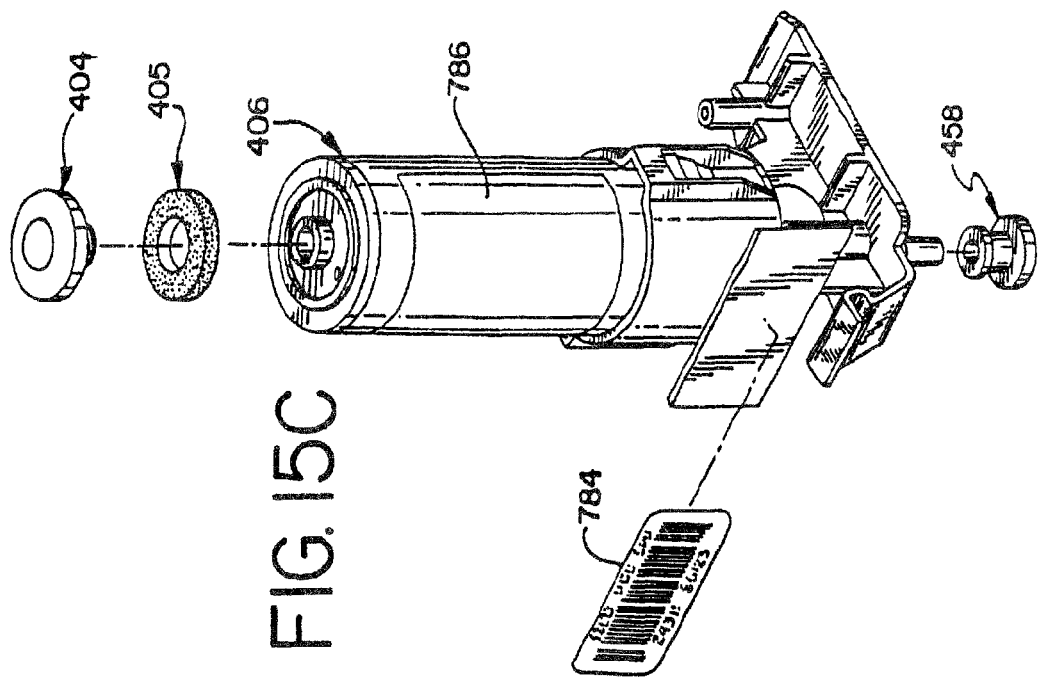
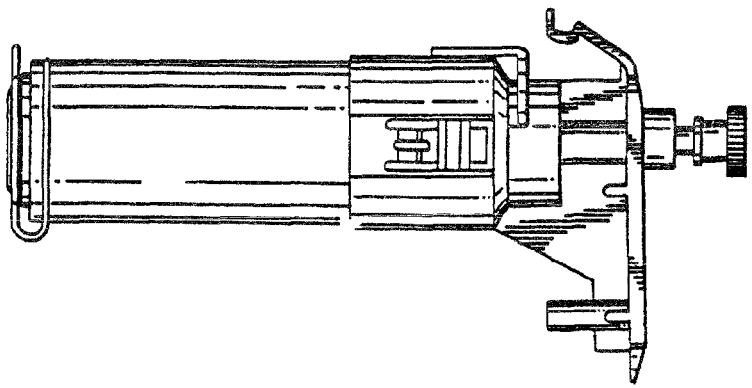
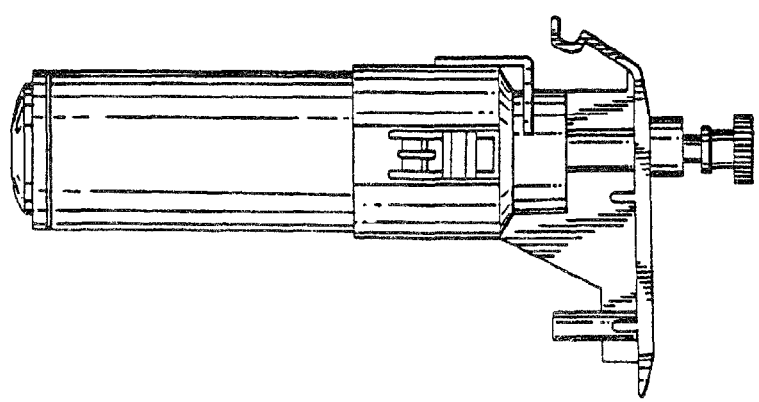

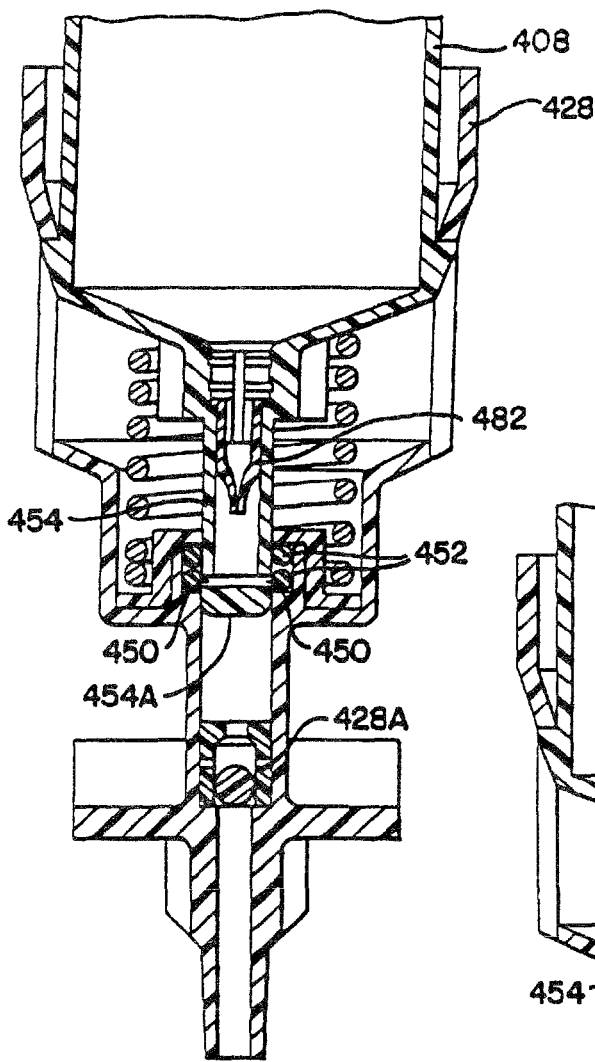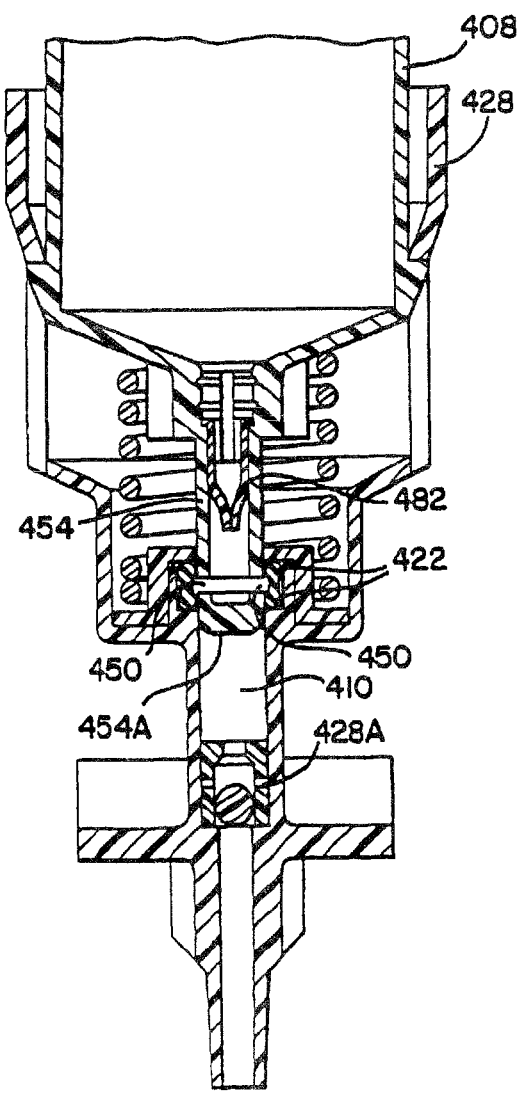

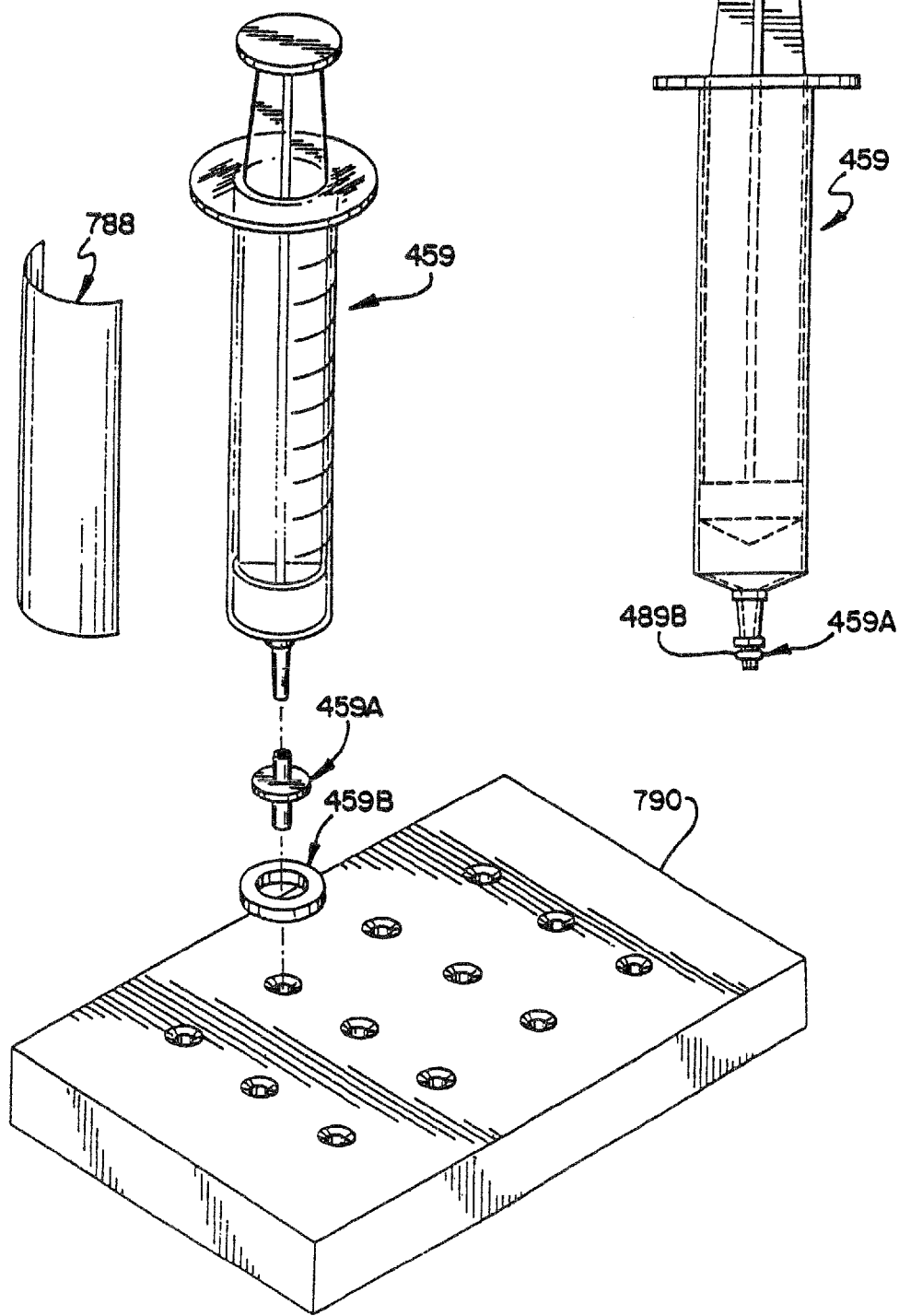

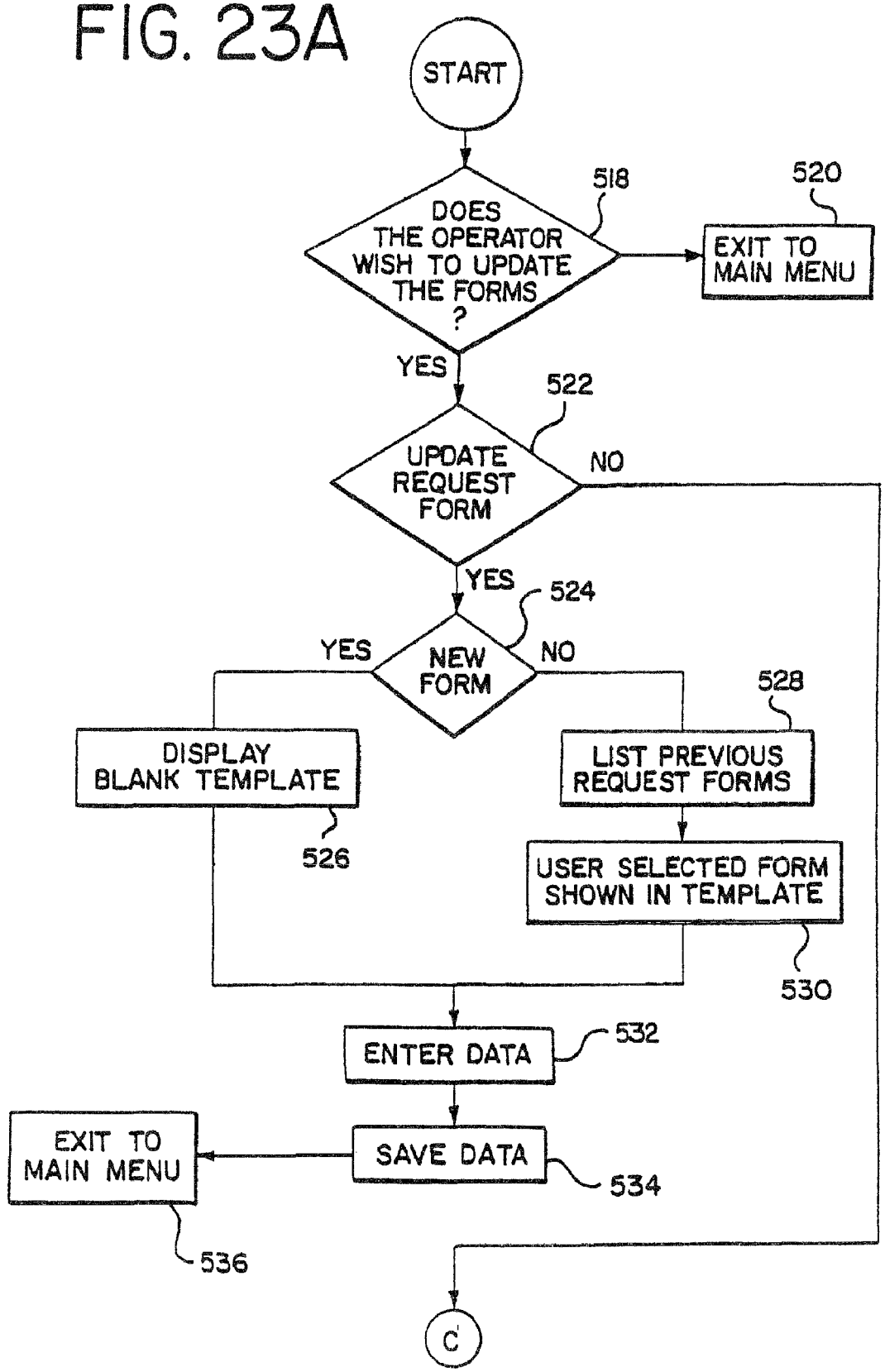

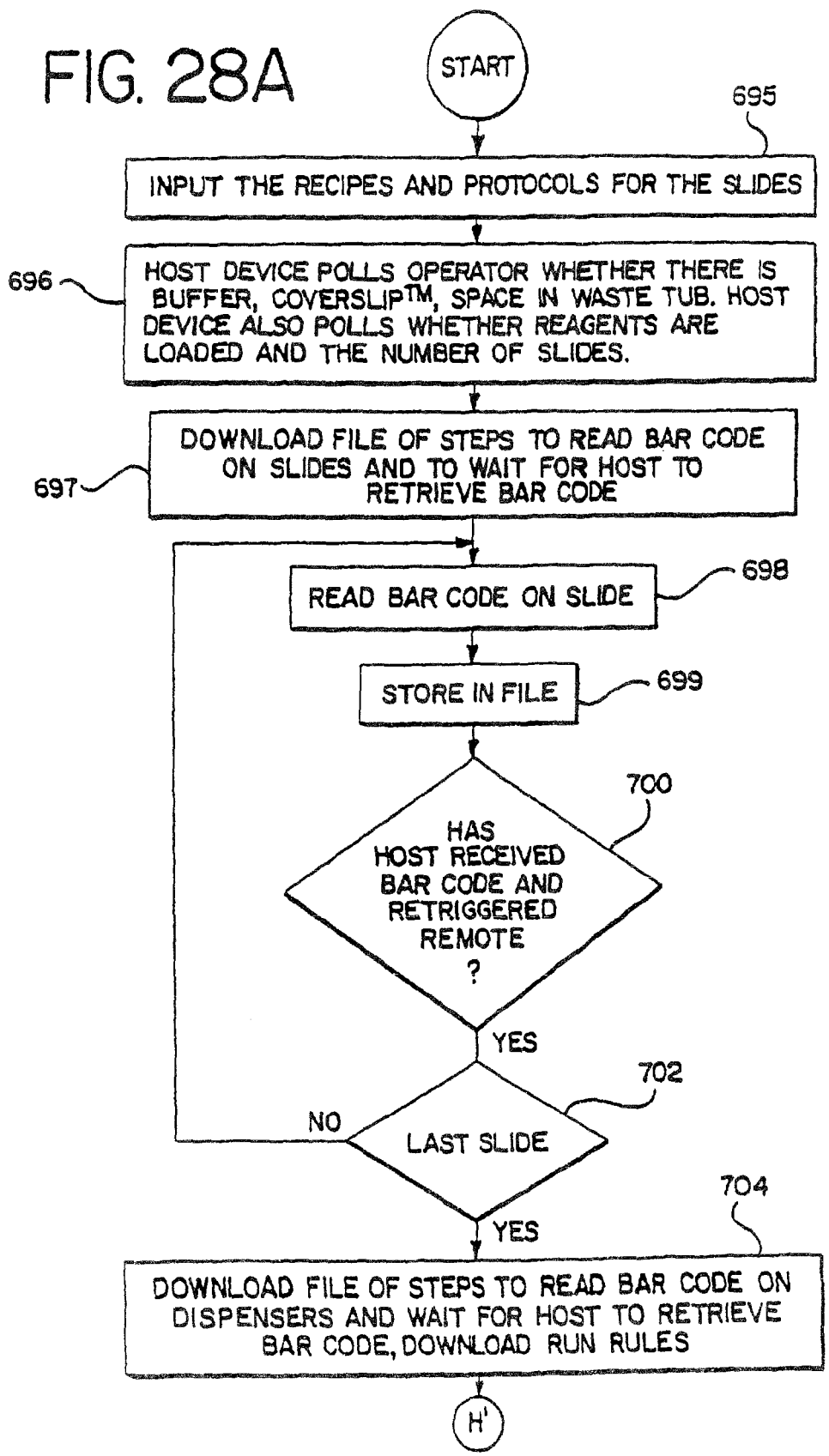

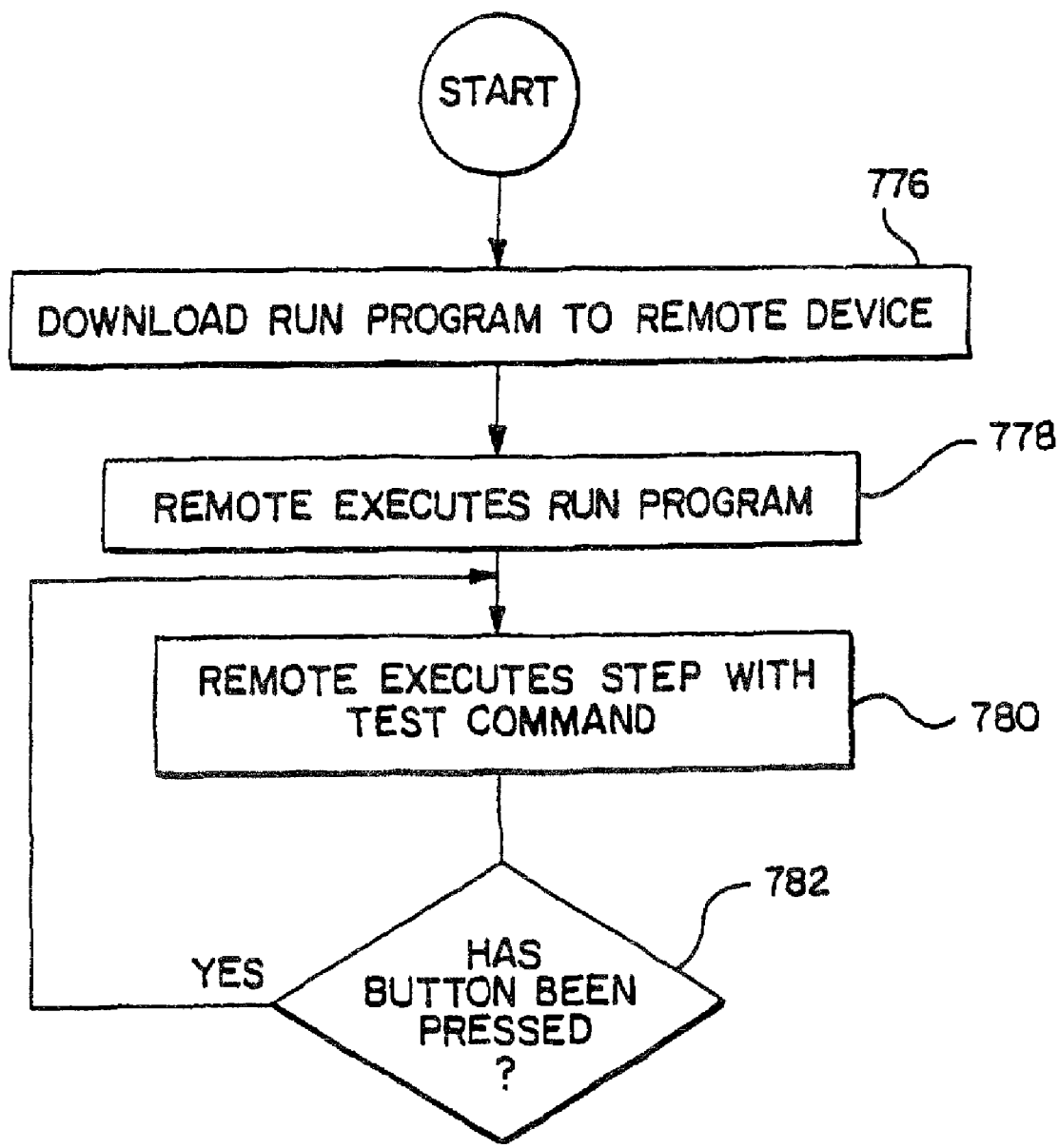

METHOD AND APPARATUS FOR MODIFYING PRESSURE WITHIN A FLUID DISPENSER

CROSS-REFERENCE TO RELATED APPLICATIONS

This application is a continuation of co-pending U.S. patent application Ser. No. 10/913,932, filed Aug. 6, 2004 now abandoned, which is a continuation-in-part of U.S. patent application Ser. No. 10/060,602, filed Jan. 30, 2002, now abandoned, which is a continuation-in-part of U.S patent application Ser. No. 09/896,649, filed on Jun. 29, 2001, now U.S. Pat. No. 6,945,128, which is a continuation of U.S. patent application Ser. No., 09/483,218 filed on Jan. 14, 2000, now U.S. Pat. No. 6,416,713, which is a divisional of U.S. patent application Ser. No. 08/995,052 filed on Dec. 19, 1997, now U.S. Pat. No. 6,045,759, which is a continuation-in-part of U.S. patent application Ser. No. 08/909,335 filed on Aug. 11, 1997, now U.S. Pat. No. 6,093,574. This application incorporates by reference all of the U.S. patent applications listed above in their entirety. This application also incorporates by reference U.S. Pat. Nos. 6,416,713, 6,045,759, 6,093,574 and 6,945,128 in their entirety.

NOTICE REGARDING COPYRIGHT

A portion of the disclosure of this patent document contains matter subject to copyright protection. The copyright owner has no objection to the facsimile reproduction by anyone of the patent disclosure document as it appears in the Patent and Trademark Office files and records but otherwise retains all copyrights whatsoever.

BACKGROUND OF THE INVENTION

A. Field of the Invention

This invention relates to biological reaction systems, and more particularly relates to a method and apparatus for an automated biological reaction system.

B. Description of Related Art

Immunostaining and in situ DNA analysis are useful tools in histological diagnosis and the study of tissue morphology. Immunostaining relies on the specific binding affinity of antibodies with epitopes in tissue samples, and the increasing availability of antibodies which bind specifically with unique epitopes present only in certain types of diseased cellular tissue. Immunostaining requires a series of treatment steps conducted on a tissue section mounted on a glass slide to highlight by selective staining certain morphological indicators of disease states. Typical steps include pretreatment of the tissue section to reduce non-specific binding, antibody treatment and incubation, enzyme labeled secondary antibody treatment and incubation, substrate reaction with the enzyme to produce a fluorophore or chromophore highlighting areas of the tissue section having epitopes binding with the antibody, counterstaining, and the like. Each of these steps is separated by multiple rinse steps to remove unreacted residual reagent from the prior step. Incubations are conducted at elevated temperatures, usually around 40° C., and the tissue must be continuously protected from dehydration. In situ DNA analysis relies upon the specific binding affinity of probes with unique nucleotide sequences in cell or tissue samples and similarly involves a series of process steps, with a variety of reagents and process temperature requirements.

Automated biological reaction systems include the biological reaction apparatus and the dispensers for the reagents and other fluids used in the biological reaction apparatus. As disclosed in U.S. Pat. No. 5,595,707, inventors Copeland et al., entitled Automated Biological Reaction Apparatus, assigned to Ventana Medical Systems, Inc. which is incorporated herein by reference, the biological reaction apparatus may be computer controlled. However, the computer control is limited in that it is dedicated to and resident on the biological reaction apparatus. Moreover, the memory, which is used in conjunction with the computer control, contains data relating to the reagents including serial number, product code (reagent type), package size (250 test), and the like.

One of the requirements in a biological reaction system is consistency in testing. In particular, the biological reaction system should apply a predetermined amount of fluid upon the slide in order to consistently test each slide in the automated biological reaction apparatus. Therefore, an important focus of a biological reaction system is to consistently and efficiently apply a predetermined amount of fluid on the slide.

Further, as disclosed in U.S. Pat. No. 5,232,664 entitled Liquid Dispenser by inventors Krawzak et al. and assigned to Ventana Medical Systems, Inc., which is incorporated herein by reference, reagents must be dispensed on the slide in precise amounts using a fluid dispenser. The fluid dispenser, which is used in conjunction with the biological reaction apparatus, should be easy to manufacture, reliable and compact in size.

SUMMARY OF THE INVENTION

In accordance with a first aspect of the invention, a fluid dispenser for an automated biological reaction system is provided. The fluid dispenser has a reservoir chamber, a dispense chamber which is substantially in line with the reservoir chamber, and a means for transferring fluid between the dispense chamber and the reservoir chamber based on pressure differential between the dispense chamber and the reservoir chamber.

In accordance with a second aspect of the invention, a fluid dispenser for an automated biological reaction system is provided. The fluid dispenser has a barrel which has a reservoir chamber and an upper portion, a cap connected to the upper portion of the barrel, a valve adjacent to the reservoir chamber, and a coupler having a dispense chamber and the coupler being coaxial with the barrel.

In accordance with a third aspect of the invention, a fluid dispenser for an automated biological reaction system is provided. The fluid dispenser has a barrel which has a reservoir chamber and an upper portion, a cap connected to the reservoir chamber, a valve adjacent to the reservoir chamber, a coupler having a dispense chamber, and a vent adjacent to the cap. The vent includes a first means to maintain constant pressure in the reservoir chamber, a second means to maintain constant pressure in the reservoir chamber, and a space, the space being between the first and second means to maintain constant pressure in the reservoir chamber.

In accordance with a fourth aspect of the invention, a fluid dispenser for an automated biological reaction system is provided. The fluid dispenser has a barrel which has a reservoir chamber and a piston at a lower portion of the barrel, a cap connected to the reservoir chamber, a valve adjacent to the reservoir chamber, and a coupler. The coupler has a dispense chamber whereby the piston moves in the dispense chamber.

In accordance with a fifth aspect of the invention, a method of assembly of a fluid dispenser for an automated biological reaction system is provided. The method includes the step of inserting a valve and a valve insert into the lower portion of a barrel. The method also includes the step of welding the cap to the upper portion of the barrel. The method further includes the step of placing the ball in the check valve ball seat. Further, the method includes the step of snapping the check valve ball seat into the coupler. In addition, the method includes the step of snapping the coupler and barrel together.

In accordance with a sixth aspect of the invention, a method of filling and priming a fluid dispenser for an automated biological reaction system is provided. The method includes the step of providing the fluid dispenser with a cap, a barrel having a reservoir chamber, the barrel being adjacent to the cap, a dispense chamber adjacent to the reservoir chamber, and a nozzle adjacent to the dispense chamber. The method also includes the step of providing a syringe with a tip and a syringe plunger. The method further includes the step of opening the cap on the fluid dispenser. The method also includes the step of filling the reservoir chamber within the fluid dispenser with fluid. In addition, the method also includes the step of closing the cap on the fluid dispenser. Further, the method also includes the step of placing the tip of the syringe inside the nozzle of the fluid dispenser without requiring the fluid dispenser be turned upside down. And, the method also includes the step of expanding the plunger of the syringe in order to draw fluid from the reservoir chamber and the dispense chamber into the syringe.

In accordance with a seventh aspect of the invention, an automated biological reaction system is provided. The automated biological reaction system has a slide support carousel, drive means engaging the slide support carousel for moving the slide support carousel, a consistency pulse application station comprising at least one nozzle for directing a stream of fluid onto a slide which is less than 35 degrees from the horizontal, and a volume adjust application station positioned above the slide for applying a predetermined amount of fluid on the slide by dropping the fluid onto the slide.

In accordance with a eighth aspect of the invention, a method of placing a consistent amount of fluid on a slide in an automated biological reaction apparatus is provided. The automated biological reaction apparatus has at least one rinse station, the rinse station comprising a rinse station nozzle positioned for directing a stream of fluid onto the slide and connected to tubing which is connected to at least one valve. The valve is connected to a bottle containing fluid, wherein the valve controls the flow of fluid from the bottle to the nozzle. The method includes the step of turning on the valve for supplying fluid to the nozzle and directing a stream of fluid onto the slide. The method also includes the step of waiting until the pressure is substantially equal in the tubing. And, the method includes the step of turning off the valve for supplying fluid to the nozzle.

In accordance with a ninth aspect of the invention, a method of washing a slide in an automated biological reaction apparatus is provided. The method includes the step of providing a rinse station comprising a first rinse station nozzle and a second rinse station nozzle, the first and second rinse station nozzles positioned to direct a stream of fluid onto the slide. The method also includes the step of directing a stream of fluid onto the slide from the first rinse station nozzle with a first momentum for a first predetermined amount of time. In addition, the method includes the step of directing a stream of fluid onto the slide from the second rinse station nozzle for a second predetermined amount of time with a second momentum. And, the method includes the step of directing a stream of fluid onto the slide from the second rinse station nozzle for a third predetermined amount of time with a third momentum, the third momentum being greater than first or second momentum, the third predetermined amount of time being greater than the first or second predetermined amount of time.

In accordance with a tenth aspect of the invention, an automated biological reaction apparatus is provided. The automated biological reaction apparatus includes a slide support carousel, drive means engaging the slide support carousel for moving the slide support carousel, a reagent delivery system for applying a predetermined quantity of reagent to one of the slides by movement of the slide support carousel in a reagent delivery zone, a heat zone for heating samples on the slide support carousel, and a rinse station. The rinse station comprises a first nozzle, a first valve connected to the first nozzle through tubing, the first valve connected to a bottle containing fluid. The rinse station further comprises a controller, the controller controlling the flow of fluid from the bottle to the first nozzle via the operation of the first valve, the controller opening the first valve until the pressure is substantially equal in the tubing.

In accordance with a eleventh aspect of the invention, an automated biological reaction system is provided. The automated biological reaction system includes a host device, the host device comprising a processor, a memory device connected to the processor, the memory device including a look-up table which contains steps for staining a slide, the processor creating a sequence of steps from the look-up table. The automated biological reaction system further includes a remote device, the remote device being physically separate from the host device, the remote device being in electrical communication with the host device. The remote device comprises a processor, a memory device connected to the processor, a slide support carousel connected to the processor, drive means engaging the slide support carousel for moving the slide support carousel, the drive means connected to the processor, a reagent delivery system for applying a predetermined quantity of reagent to one of the slides by movement of the slide support carousel in a reagent delivery zone, the reagent delivery system connected to the processor, a heat zone for heating samples on the slide support carousel, the heat zone connected to the processor, and a rinse station for rinsing slides on the slide support carousel, the rinse station connected to the processor, the remote device receiving the sequence of steps from the host device, the remote device executing, through the processor, the sequence of steps in the processor to control the slide support carousel, the reagent delivery system, the heat zone and the rinse station.

In accordance with a twelfth aspect of the invention, a method for generating a run program in an automated biological reaction system is provide. The method includes the step of providing a host device and a remote device, the remote device being physically separate from the host device, the remote device being in communication with the host device. The method also includes the step of reading by the remote device of a barcode on a slide in a carousel on the remote device. The method further includes the step of reading by the remote device of a barcode on a dispenser in the remote device. In addition, the method includes the step of sending of the slide barcode and dispenser barcode from the remote device to the host device. Also, the method includes the step of generating of a sequence of steps for a run based on the slide barcode and dispenser barcode. Moreover, the method includes the step of determining by the host device whether the remote device is capable of executing the sequence of steps. And, the method includes the step of sending by the host device of the sequence of steps to the remote device.

In accordance with a thirteen aspect of the invention, a memory management system for an automated biological reaction apparatus is provided. The memory management system includes a memory device, the memory device including a table containing data for a dispenser used in the automated biological reaction apparatus. The memory management system also including a means to transfer the data in the memory device to a host device. The host device comprises a processor, a host memory device connected to the processor. The host memory device includes a look-up table. The processor is connected, via the means to transfer the data in the memory device to a host device, to the memory device, and the processor updates the look-up table in the host memory device based on comparisons to the table in the memory device.

In accordance with a fourteenth aspect of the invention, a method for updating dispenser information in an automated biological reaction system is provided. The method includes the steps of providing a host device and a memory device, the host device comprising a processor, a host memory device connected to the processor, the host memory device including a look-up table, the memory device including barcode and expiration date information for the dispenser used in the automated biological reaction apparatus. The method also includes the step of reading by the host device of the barcode and expiration date information in the memory device. In addition, the method includes the step of updating the look-up table in the host device based on the barcode and expiration date information in the memory device. And, the method includes the step of writing in the memory device that the barcode and expiration date information has previously been read.

In accordance with a fifteenth aspect of the invention, a method for programming a memory device for an automated biological reaction system is provided. The method includes the step of selecting a form which includes information on numbers and types of dispensers in a kit for the automated biological reaction system. The method also includes the step of scanning in barcodes for a set of dispensers. Moreover, the method includes the step of determining the type of dispenser for each of the dispensers scanned in. Further, the method includes the step of comparing whether the numbers types of dispensers scanned in correspond to the numbers and types of dispenser in the kit form. And, the method includes the step of programming the memory device if the numbers types of dispensers scanned in equal the numbers and types of dispenser in the kit form.

In accordance with a sixteenth aspect of the invention, a fluid dispenser for an automated biological reaction system is provided. The fluid dispenser has a barrel, the barrel having a reservoir chamber and an upper portion. The fluid dispenser also has a cap connected to the upper portion of the barrel. The fluid dispenser also has a cup check valve, the cup check valve having a first end and a second end, the cup check valve adjacent to the reservoir chamber at the first end, the cup check valve having a cup piece at the second end. The fluid dispenser further has a dispense chamber adjacent to the second end of the cup check valve.

In accordance with a seventeenth aspect of the invention, a valve is provided. The valve passes fluid from one side of the valve to the other side based on a pressure differential between the one side and the other side, whereby the valve is placed in a housing. The valve includes an attachment, the attachment piece being attached to the housing, a connecting piece being connected to the attachment piece, and a cup piece. The cup piece is connected to the connecting piece. The cup piece abuts against the housing when the pressure on the one side of the valve is equal to the pressure on the other side of the valve. The cup piece does not abut against the housing when the pressure on the one side of the valve is unequal to the pressure on the other side of the valve.

In accordance with a eighteenth aspect of the invention, a method of equilibrating pressure within a fluid dispenser is provided. The method includes the step of providing a fluid dispenser with a barrel having a cap. The cap includes a surface with at least one hole and a valve having a biasing member and a hole sealer. The biasing member includes at least two positions. The also includes the step of placing the biasing member in one of the two positions by applying a force to the valve wherein in a first position of the biasing member, the hole sealer seals the hole and wherein in a second position, the hole sealer does not seal the hole.

In accordance with a nineteenth aspect of the invention, a method of mechanically operating a valve for a fluid dispenser is provided. The valve of the fluid dispenser includes a head and a bulge. The method includes the step of abutting the bulge against a hole in the fluid dispenser to create a seal. The method also includes the step of applying a mechanical force to move the head so that the bulge does not abut the hole. Further, the method includes the step of reducing the mechanical force so that the bulge abuts the hole.

In accordance with a twentieth aspect of the invention, a method for passing liquid through a housing based on a pressure differential is provided. The method includes the step of providing a valve having an attachment piece, a connecting piece being connected to the attachment piece, and a cup piece, the cup piece being connected to the connecting piece. The method also including the step of abutting the cup piece against the housing when the pressure on the one side of the valve is equal to the pressure on the other side of the valve. And, the method includes the step of flexing the cup piece inward so that the cup piece is not abutting against the housing when the pressure on the one side of the valve is unequal to the pressure on the other side of the valve.

In accordance with a twenty-first aspect of the invention, a fluid dispenser for an automated biological reaction system is provided. The fluid dispenser has a barrel having a reservoir chamber and a piston, the piston being adjacent to the reservoir chamber. The fluid dispenser also has an extension piece connected to the piston. And, the fluid dispenser has a coupler, wherein the coupler has a dispense chamber. The dispense chamber is adjacent to the reservoir chamber. Further, the extension piece moves inside the coupler.

Accordingly, a primary object of the invention is to provide an automated biological reaction system which is modular in design.

Another object of the invention is to provide an automated biological reaction system which provides for a means of automatically downloading data relating to the reagents including serial numbers, reagent types, lot numbers, expiration dates, dispenser type, and the like in an efficient and reliable manner.

Another object of the invention is to provide an automated biological reaction system which consistently and efficiently applies a predetermined amount of buffer upon the slide to which a precise volume of reagent can be added upon the slide.

A further object of the invention is to provide a fluid dispenser, which is used in conjunction with the biological reaction apparatus, which, is reliable.

Yet a further object of the invention is to provide a fluid dispenser, which is used with a wider array of chemistries in conjunction with the biological reaction apparatus, which is easy to manufacture.

Still another object of the invention is to provide a fluid dispenser, which is used in conjunction with the biological reaction apparatus, which is compact in size.

Still yet another object of the invention is to provide a fluid dispenser which is easy to prime.

These and other objects, features, and advantages of the present invention are discussed or apparent in the following detailed description.

BRIEF DESCRIPTION OF THE DRAWINGS

A presently preferred embodiment of the present invention is described herein with reference to the drawings wherein:

FIG. 5B is a format of the addressing for the host devices and remote devices described in FIG. 5A;

FIG. 7A is a block diagram of the dual rinse and volume adjust components of the remote device in FIG. 6A;

FIG. 12A is an elevational cutaway view of a prefilled fluid dispenser in the extended position;

FIG. 12B is an elevational cutaway view of a user fillable fluid dispenser in the extended position;

FIG. 12C is an elevational cutaway view of a prefilled fluid dispenser in the compressed position;

FIG. 14A is an exploded view of an elevational cutaway of a prefilled fluid dispenser;

FIG. 14B is an exploded view of an elevational cutaway of a user fillable fluid dispenser;

FIG. 15A is a side view of a prefilled fluid dispenser;

FIG. 15B is a side view of a customer fillable fluid dispenser with flip top;

FIG. 15C is an exploded view of a prefilled fluid dispenser with an evaporation ring adjacent the cap;

FIG. 18A is an alternative embodiment of a cutaway view of the lower portion of the fluid dispenser;

FIG. 18B is an alternative embodiment of a cutaway view of the lower portion of the fluid dispenser;

FIG. 19A is a cutaway view of a syringe with a restrictor for use in the nozzle of the coupler;

FIG. 19B is an exploded view of a syringe with a restrictor and an O-ring for use in the nozzle of the coupler;

FIGS. 28A-28G are flow charts of a preparation for a run using the dispense table; and FIG. 29 is a flow chart of the testing run for the remote device.

DETAILED DESCRIPTION OF THE PREFERRED AND ALTERNATIVE EMBODIMENTS OF THE INVENTION

The automated immunostaining system of this invention performs all steps of immunohistochemical irrespective of complexity or their order, at the time and temperature, and in the environment needed. Specially prepared slides containing a bar code identifier and a mounted tissue section are placed in special supports on a carousel, subjected to a preprogrammed sequence of reactions, and are removed from the carousel, ready for examination. For purposes of clarity of the following description of the apparatus of this invention and not by way of limitation, the apparatus will be described in terms of immunohistochemical processes.

Figure 1:
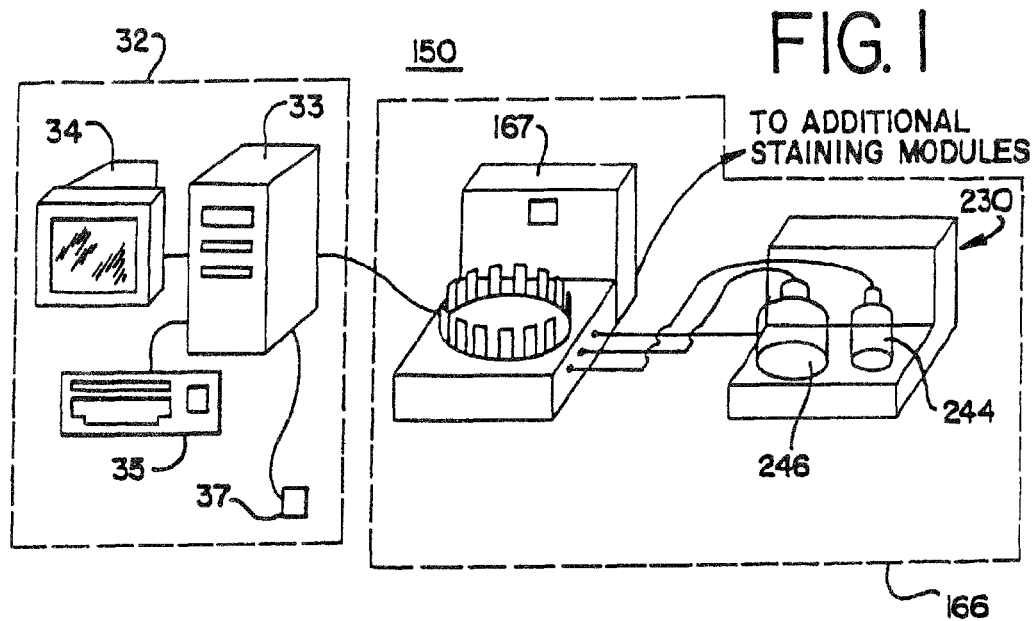
FIG. 1 is a left front, isometric view of the automated biological reaction system according to a first embodiment of this invention.
Figure 2:
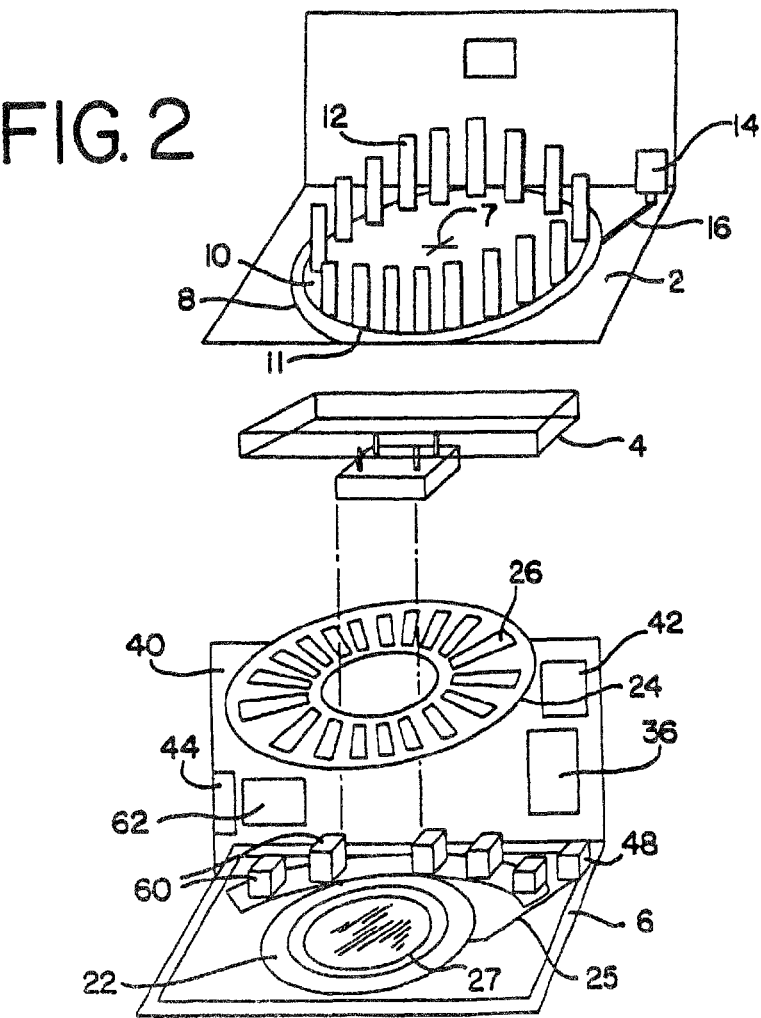
FIG. 2 is an exploded right front isometric view of the system shown in FIG. 1.

FIG. 1 is front right isometric view of the automated biological reaction system with a host device 32 and one remote device 166. The remote device 166 includes a staining module 167, bulk fluid module 230 and the host device 32 includes a host computer 33, a monitor 34, a keyboard 35 and a mouse 37. FIG. 2 is a front right isometric view of the staining module which is part of the automated biological reaction system. Liquid and air supply tubing and electrical wiring connecting the respective components are conventional, well known in the art, and are omitted from the drawings for purposes of clarity.

The apparatus has an upper section 2, intermediate section 4 and lower section 6. In the upper section 2, reagent tray 10 which supports the reagent fluid dispensers 12 is mounted for rotation about its central axis 7 on reagent carousel 8. The reagent carousel 8 and slide carousel 24 are circular in the preferred embodiment, but can be any shape which allows integration with other components in the system. Reagent fluid dispensers 12, described herein with respect to FIGS. 10-21, required for the immunohistochemical reactions to be conducted during slide treatment cycle, are supported by the reagent tray 10 and mounted in reagent fluid dispenser receptors 11. These receptors 11 are configured to receive reagent fluid dispensers 12. The receptors 11 are preferably equally spaced in a circular pattern axially concentric with the carousel axis 7. The number of receptors 11 provided should be sufficient to accommodate the number of different reagent fluid dispensers 12 required for a cycle or series of cycles. Twenty-five fluid dispenser receptors 11 are shown, but the number can be smaller or greater, and the diameter of the reagent tray 10 can be increased to accept a larger number of reagent fluid dispensers 12. The reagent carousel 8 is rotated by the stepper motor 14 drive belt 16 to a position placing a selected reagent fluid dispenser 12 in the reagent deliver position under the air cylinder reagent delivery actuator over a slide to be treated with reagent.

Figure 3:
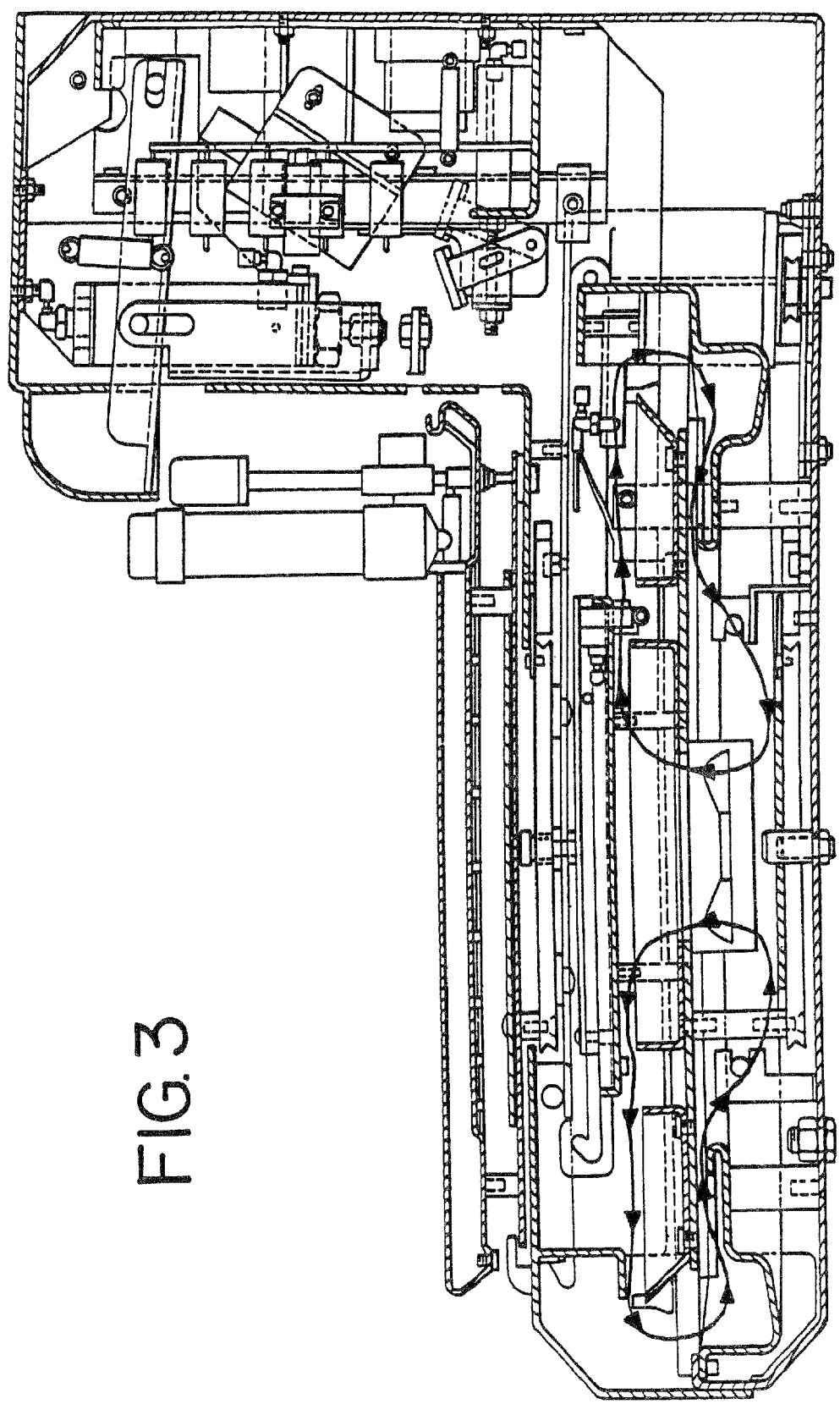
FIG. 3 is a partial exploded left front isometric view of the system shown in FIG. 1.

The intermediate section 4 comprises a vortex mixing plate to which the 4 of the 6 mix blocks are attached, the remaining two mix blocks being mounted on the lower section. The lower section 6 comprises support plate 22 upon which the slide carousel 24 is rotatably mounted. The slide carousel 24 supports slide supports 26. Heated air is supplied to the apparatus via a resistive heating element and a blower. The heated air recirculates within the apparatus as shown in FIG. 3. The support plate 22 also supports a remote device microcontroller 36 on the automated biological reaction apparatus, power supply 24 and fluid and pneumatic valves 62. The remote device microcontroller printed circuit board 36, as described subsequently, is generally a processor and can be replaced by a standard computer. The remote device microcontroller printed circuit board 36 interfaces, via an RS-485 line, with a host device 32, as described subsequently in FIGS. 5A-5C. The lower section 6 includes support plate 40 upon which are supported accessories such as power supply 42 and buffer heater 44.

In the lower section 6, the stepper motor 48 rotates the slide carousel 24, engaging drive belt 25 engaging the drive sprocket of the slide carousel 24. The annular waste liquid sump surrounds the shroud and is supported on the bottom of plate 22. The waste reagent and rinse fluids are collected in the sump and passed to a drain through an outlet tube in the sump bottom (not shown).

Figure 4:
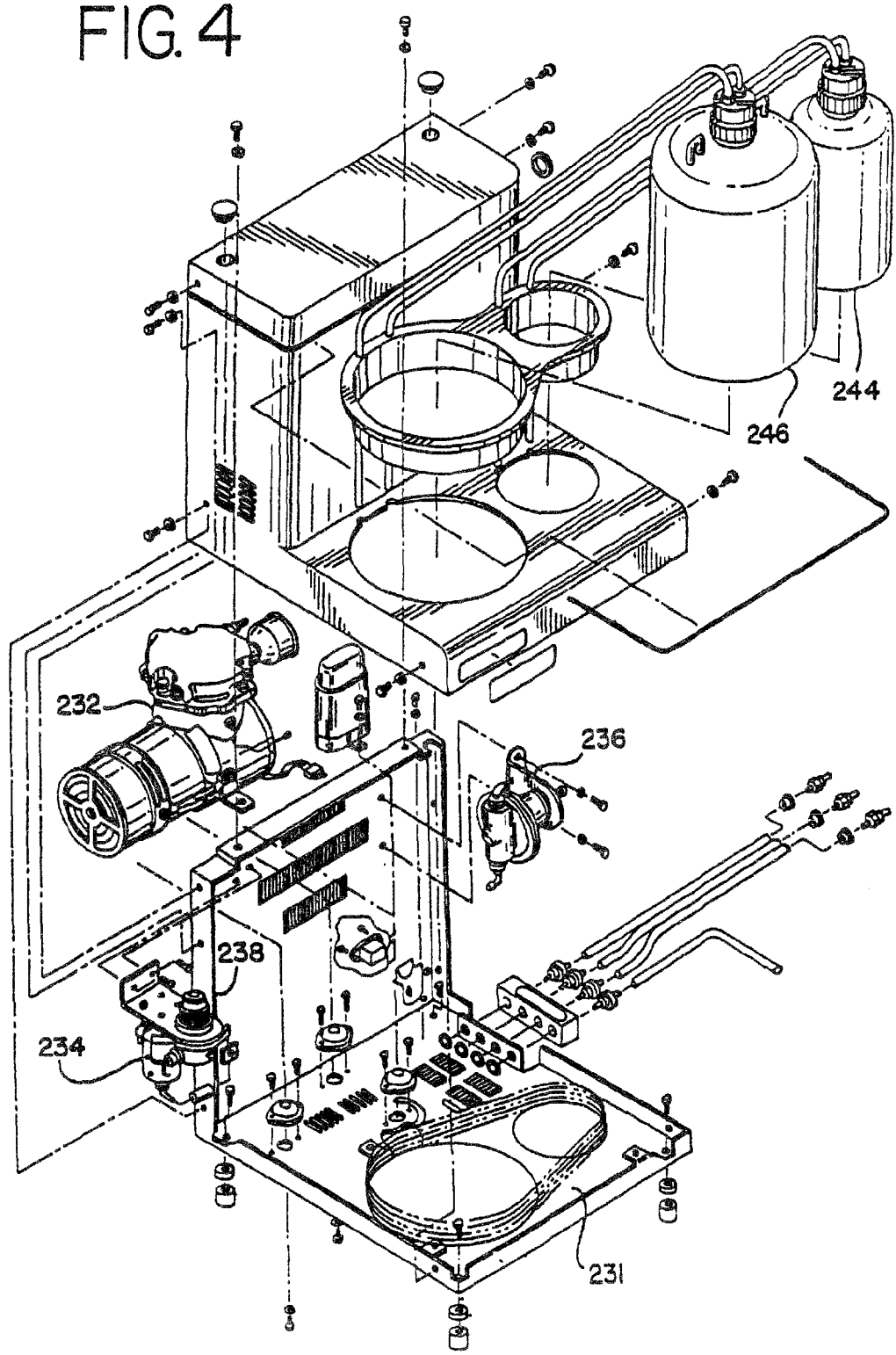
FIG. 4 is a partial exploded right rear isometric view of the apparatus shown in FIG. 1.

Rinse and Liquid Coverslip™ (which is light oil substance used to prevent evaporation of the aqueous solutions on the slide) spray blocks 60 are supplied with fluid through conventional solenoid valves 62 (see also FIG. 6A, 248F-J). Buffer heater temperature sensor 66, mounted on buffer heater 44, controls the heat energy supplied to the buffer heater 44. Slide temperature monitoring sensor 68, mounted on support plate 22, controls the temperature of the air in the apparatus by controlling energy supplied to annular heater elements 27. Power supply 42 provides power to the stepper motors 14, 48 and control systems. FIG. 4 is a left front isometric view of the bulk fluid module system 230 which is included in the automated biological reaction system 150. The bulk fluid module 230 includes an air compressor 232, a pressure relief valve (prv) 238, cooling tubing 231, a water condenser and filter 234, an air pressure regulator 236, a bottle containing wash buffer 246, and a bottle containing Liquid Coverslip™ 244. The air compressor 232 provides compressed air which is regulated by the pressure relief valve (prv) 238 to 25 psi. The air passes from the compressor 232 through the cooling tubing and enters the condenser and filter 234. From the condenser and filter 234, the air passes to the pressure regulator 236. The pressure regulator 236 regulates the pressure to 13 psi. The air, maintained at 13 psi, is supplied to the wash buffer bottle 246 and the Liquid Coverslip™ bottle 244 and the staining module 167 (see FIG. 2). Water condensing out of the compressed air passes out of the condenser and filter through the pressure relief valve and exits the bulk module. Wash buffer and Liquid Coverslip™ are supplied to the staining module.

Figure 5A:
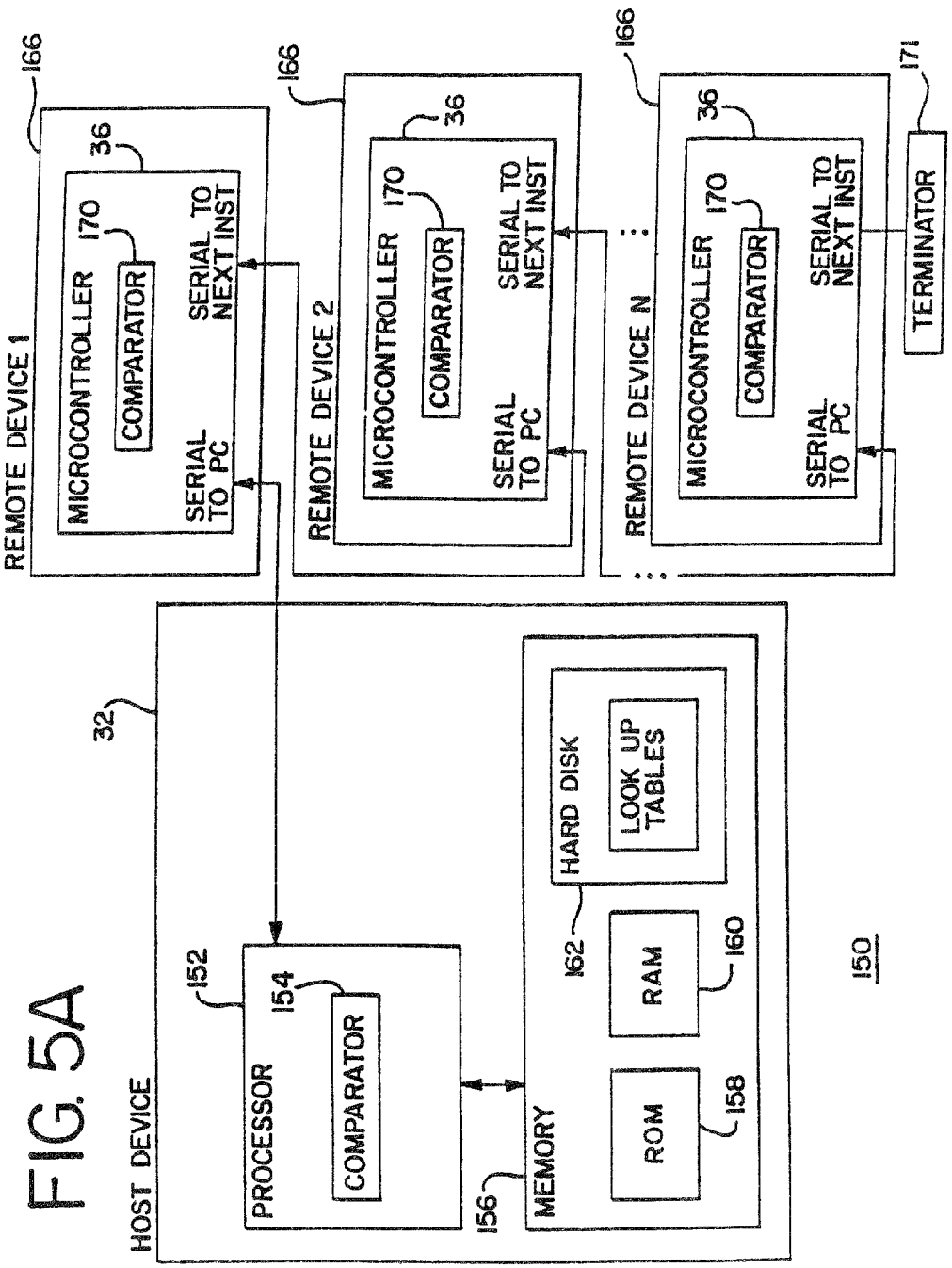
FIG. 5A is a block diagram of the modularity of the host and remote devices of the automated biological reaction system.

Referring to FIG. 5A, there is shown a block diagram of the automated biological reaction system 150. The automated biological reaction system 150 is segmented into a host device 32, which includes a typical personal computer, and at least one remote device 166, which includes the automated biological reaction device in FIGS. 2 and 6A. In the preferred embodiment, there are up to eight remote devices 166 which communicate with the host device 32. Each remote device 166 on the network has a unique address so that each remote device 166 may be identified and individually controlled by the host device 32. As described subsequently in FIG. 5B, the automated biological reaction system 150 can support up to eight remote devices 166 due to the 3 bits (values 0-7) dedicated to the addressing of the remote devices 166. A rotary switch is provided on the remote device 166 to allow for the identification and the changing of the 3 bit address for each remote device 166. All host messages include this address in them, as described subsequently in FIG. 5B. However, the number of remote devices 166 can be smaller or larger than eight, depending on the capacity requirements or practical limitations of the laboratory in terms of space. Moreover, the remote devices 166 may be immunohistochemistry staining modules, another type of instrument that performs a different type of staining, or another type of medical testing device.

Communication between the host device 32 and the remote devices 166 is accomplished using a serial RS-485 link, which serves as a network, that supports one host and up to 32 remotes at one time. In the preferred embodiment, addressing of the remote devices 166 allows up to 8 remote devices to communicate with the host at one time. The RS-485 link has at least two pairs of lines for communication, one pair for transmitting and one pair for receiving. The remote devices 166 which are connected to the network "hear" the host messages but do not "hear" other remote messages. In the preferred embodiment, all communications begin with a host message, followed a short time later by a response by a remote device 166 if present. If the host device 32 sends a message and there is no remote device 166 to respond to it, the host device 32 times out. In this manner, the communication provides a simple, collision-free link between the host device 32 and the remote devices 166. In an alternative embodiment, the remote devices 166, in addition to communicating with the host device 32, address each other. For example, the remote devices 166 address each other using the unique 3 bit address, sending information about staining runs, which are described subsequently.

As shown in FIG. 5A, the host device 32 is a typical personal computer with a processor 152 which includes a comparator 154 for comparing values in the processor. The processor 152 is also in communication with memory devices 156, including non-volatile memory devices such as a ROM 158, volatile memory devices such as a RAM 160, and a hard disk 162. Any of the memory devices may contain databases or look-up tables; however, in the preferred embodiment, the hard disk 162 contains the databases or look-up tables 164. The remote device 166 includes a processor, such as a microcontroller 36 wherein the microcontroller 36 has a comparator 170 for comparing values in the microcontroller 36. In an alternative embodiment, the microcontroller 36 in the remote device 166 is replaced by a personal computer. The microcontroller 36 is manufactured by Dallas Semiconductor, model number DS2251T 128K Soft microcontroller module. The microcontroller 36 has two lines (serial to PC, serial to next inst) to facilitate communication between the host and the remote devices. As shown in FIG. 5A, the host device 32, through the processor 152, is connected to the serial to PC pin of the microcontroller 36 of remote device 1 (166). The serial to next inst line of the microcontroller 36 of remote device 1 is connected to the serial to PC pin of remote device 2 (166). The connections follow similarly through remote device N (166). In the preferred embodiment, there are up to 8 remote devices on the network. In order to terminate the network with the correct impedance in order to avoid any pulse reflections on the network, the serial to next instrument line is connected to a terminator 171. The terminator 171 can thereby match the impedance of the network. In the event that one of the remote devices on the network must be removed from the network, the serial to PC line and the serial to next remote device line need only be connected to each other for the remote device 166 to be removed from the network. Thereby, the network does not "see" that remote device 166 and is effectively removed from the network.

Referring to FIG. 5B, there is shown a format of the addressing for the host and remote devices 166 described in FIG. 5A. Both the host device 32 and the remote devices 166 have the same format and are distinguishable from one another only by the messages in their fields. Both the host device command and the remote device response for a given message transaction contains the same message. The first character is the start of message character. The $8^{th}$ bit is always set to 1, the lower 3 bits contain the address of the remote and bits 3-6 are unused. The host device 32 addresses the remote device 166 in this manner. The addressed remote responds in kind with its own address here.

The message length is 2 characters in length. This number indicates the number of characters in the entire message. This includes the start of message character and the message checksum character. This is the actual number of characters transmitted as seen through the host/remote serial ports. The message ID is one character in length. It tags a message with a number (0-255) that identifies it from other messages. The message ID provides identification for message acknowledges from the remote and provides safe message retry processing in the remote. The message ID is implemented by incrementing a number until it reaches 255, and thereafter returning to 0. Each successful message transmission causes the message ID to increment by 1. Retransmitted messages from the host, due to unsuccessful acknowledgments from the remote, are repeated with the same message ID as the original message. The message command is 1 character in length. For host messages, the message command indicates to the remote the type of command the message command data pertains to. For remote messages, this field is used to tell the host device 32 how the request was received. The message command data is of variable length. It contains additional message data, depending on the particular host command. The size of the message command data is dictated by the message length, described previously. After removing the other fields from around this field, the remainder is the message information. Since message commands may not require message command data, this field may not always be used. The message checksum is 1 character in length. It contains the computed checksum of all characters in the message, starting with the start of message character and including all message characters up to, but not including, this checksum field. No message is processed if the message checksum does not match the actual computed checksum of the received message.

Figure 5C:
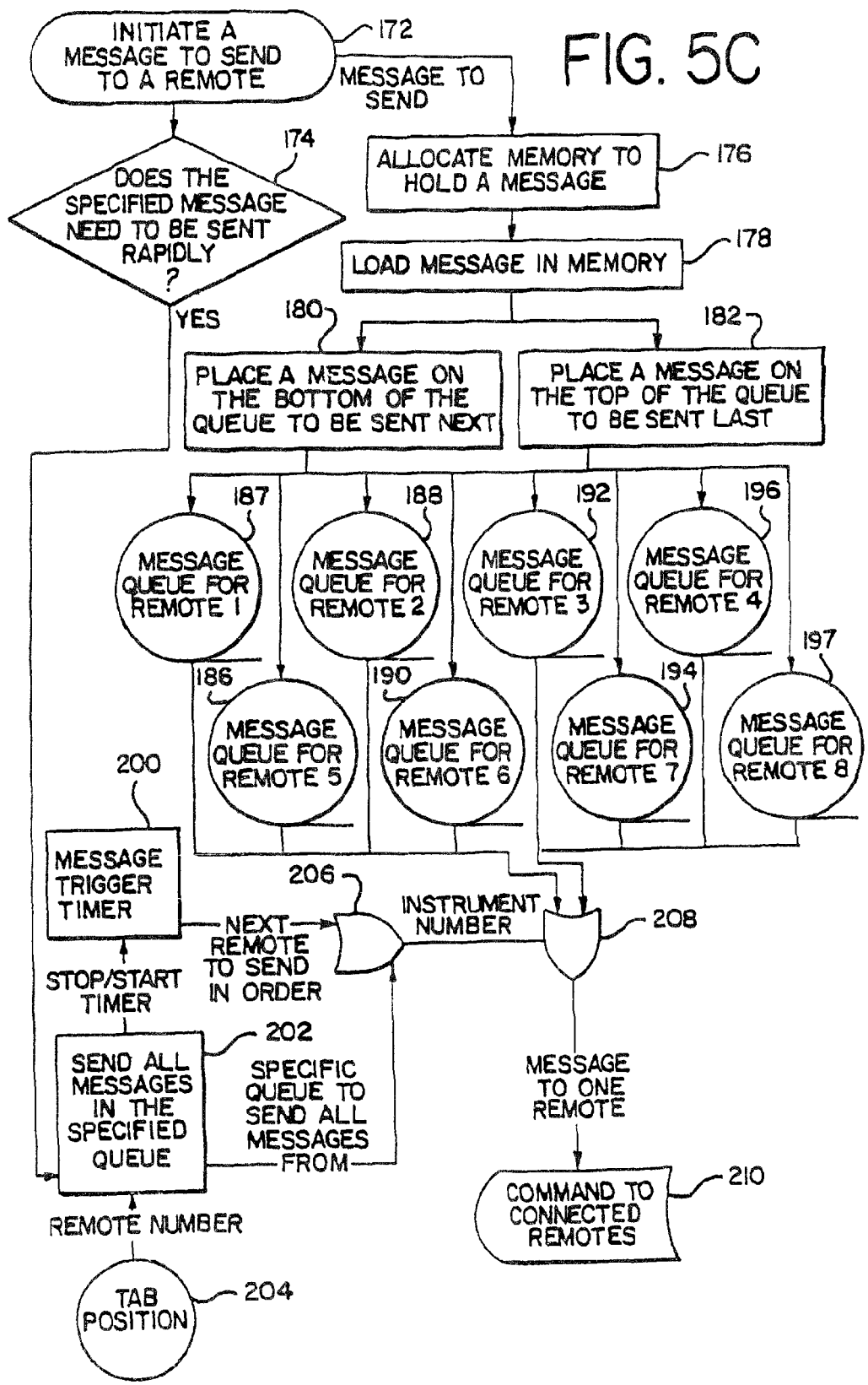
FIG. 5C is a communication transmission protocol between the host device and remote devices described in FIG. 5A.

Referring to FIG. 5C, there is shown a communication transmission protocol between the host device 32 and remote devices 166 described in FIG. 5A. Messages are downloaded from the host device 32 to the remote devices 166. The host device initiates a message to send to a remote device (172). The host device allocates memory to hold a message 176 and loads the message into memory 178. The host device 32 then places the message at the top or at the bottom of the queue 180, 182, depending on the priority of the message. Since the queue is first-in-first-out, the messages at the bottom of the queue go out first. Therefore, if a message must be sent out immediately, it is placed at the bottom of the queue 180. Otherwise, if it is a routine status message, the message is placed at the top of the queue 182. Thereafter, the messages are sent to the message queues for each of the up to eight remote devices 184, 186, 188, 190, 192, 194, 196, 198.

Ordinarily, when a message is sent from the host device 32 to a remote device 166, messages are sent periodically through the use of a timer. When the host device 32 determines that a message needs to be sent rapidly 174, the timer is turned off 200 and all of the messages from the specific queue as indicated by the host are sent 202. If the host device 32 determines that the message does not need to be rapidly sent, the message is sent in the predetermined sequence based on the timer by sending it in the predetermined sequence 206. The host uses the tab position 204, which indicates which remote to send the message to.

Figure 6A:
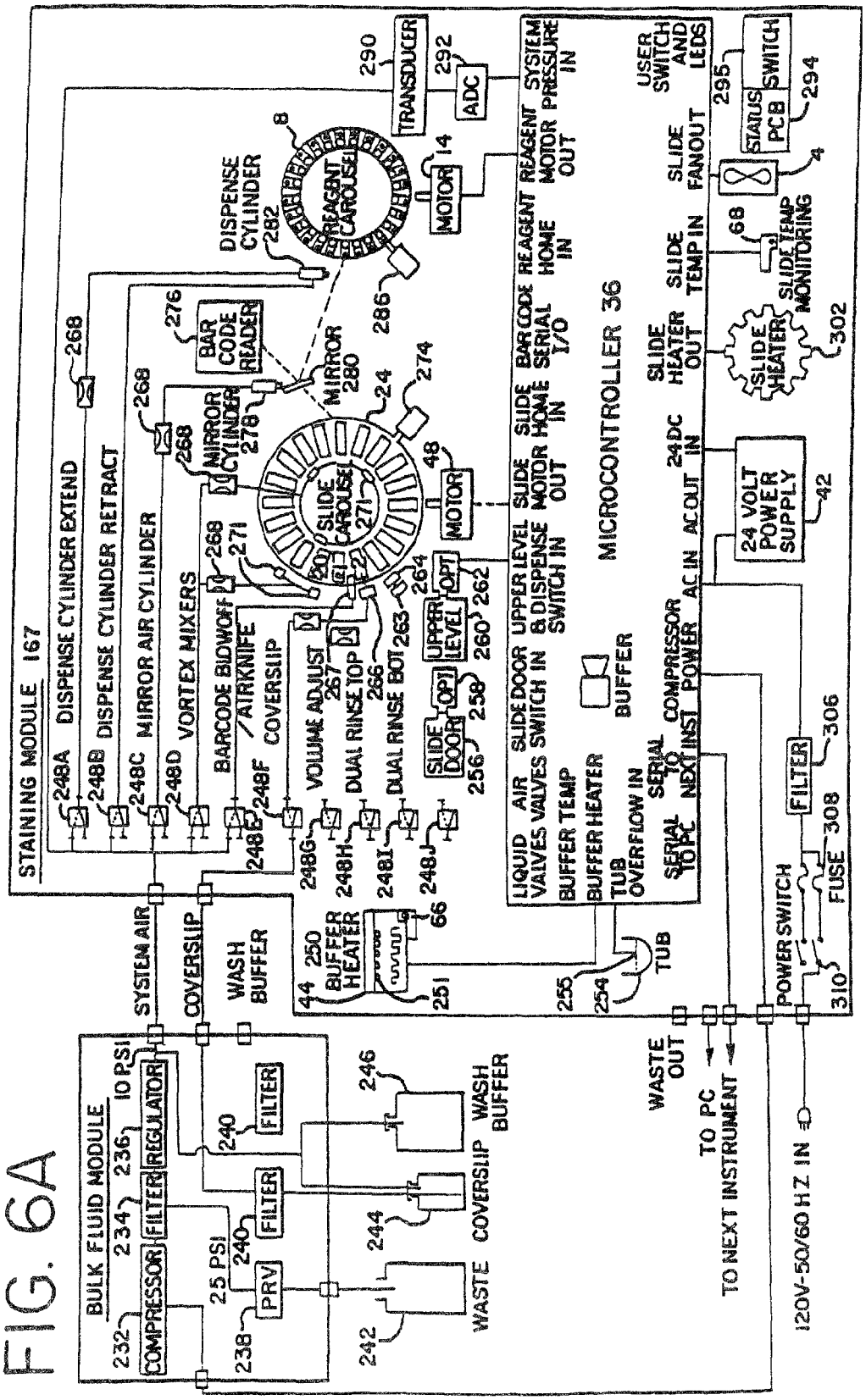
FIG. 6A is an expanded block diagram of the remote device in FIG. 5A.

Referring to FIG. 6A, there is shown an expanded block diagram of the remote device 166. As discussed previously, the remote device 166 includes a microcontroller 36. The microcontroller 36 has a user switch and LEDs line which connects to the status PCB (printed circuit board) 294. The status PCB 294 is the interface to the user for the remote device 166 and includes three LEDs (light emitting diodes) for power determination, error notification and notification of a run in progress. The status PCB 294 also includes a switch 295, such as a push-button switch, which is used for testing of various functions. When the push-button switch 295 is depressed, the microcontroller 36 executes the last set of instructions (described later as macro 0) that was entered in the microcontroller 36. Macro 0, as described subsequently, is a list of instructions which are used to execute a staining run in the remote device 166. For testing purposes, operators may wish to review the last staining run. In order to do this without requiring the operator to download the program from the host device 32 to the remote device 166 (which may be in a different location), the operator may depress the pushbutton switch 295. In this manner, the operator may repeatedly execute the last run at the touch of a button.

The microcontroller 36 also has a slide fan out connection which is used to control the blower fan 4. The blower fan 4 recirculates air to heat the slides on the slide carousel 24 of the remote device 166 by forcing air over the heater 302 and then over the slides. The slide temp in connection on microcontroller 36 is connected to the slide temperature monitoring sensor 68 which senses the temperature of the air. The slide temperature monitoring sensor 68 is positioned in the path of the heated air and thereby sends information to the microcontroller 36 when to turn the slide heater 302 on and off. The slide heater out connection is connected to the slide heater 302 which, as discussed previously, heats the air in order to elevate the temperature of the slides. As discussed subsequently, the host device 32 downloads to the remote device 166 both the sequence of steps in a run program, and the sensor monitoring and control logic called the run rules. One of the environmental parameters is the upper and lower limit of the air temperature of the slides (used for heating the slides). If, during a run, the environmental temperature is below the lower limit, as indicated by slide temperature monitoring sensor 68, the slide heater 302 is turned on. Likewise, if the environmental temperature is above the upper limit, as indicated by slide temperature monitoring sensor 68, the slide heater 302 is turned off. The power supply 24 supplies both 24 VDC and 5 VDC to the applicable 24 VDC and 5 VDC connections. The 24 Volt power supply 24 is used to power the motors 14, 48 which move the slide carousel 24 and the reagent carousel 8, and the valves 248A-J, which are described subsequently. The 120 VAC input is sent through a power switch 310, a fuse 308 and a filter 306 to the AC In connection of the power supply 24. The 120 VAC input is also used to power the slide heater 302, buffer heater 44 and compressor 232 of the bulk fluid module, which are described subsequently. The serial to PC line and the serial to next remote device line are described with reference to FIG. 5A. The tub overflow in line receives input from a conductivity sensor 255 which senses the level of the waste in the tub 254. When the conductivity sensor 255 senses that the waste line is above a predetermined level, the conductivity sensor 255 notifies the microcontroller 36, which in turn sends a status message to the host device 32. The operator is first given an opportunity to clear the waste from the tub 254. If the tub 254 is still above the predetermined level, the run is stopped.

The buffer heater 44 is used to heat the wash buffer before it is placed on the slides since it has been determined that better results are achieved by heating the wash buffer to the temperature of the tissue on the slide. The buffer heater 44 consists of a cast aluminum block 250 with a spiral tubing 251 inside the block. When the wash buffer flows through the tubing 251 through the block 250, the temperature of the wash buffer will be the temperature of the aluminum block 250 upon exit from the tubing 251. In order to control the temperature of the block, a buffer heater temperature sensor 66 is used which is physically placed on the aluminum block 250. The microcontroller 36 receives the buffer temperature sensor input via the buffer temp line and can thereby control the temperature of the buffer heater 44 by turning on and off the buffer heater 44 via the buffer heater line on the PCB microcontroller 36.

The fluid valves 248A-J for the Liquid Coverslip™ and the wash buffer are controlled by the fluid valve connections. There is a separate pair of wires (power and ground) for each valve 248A-J shown in FIG. 6A which are omitted for ease of display. Each valve 248A-J is a relay which is activated by the microcontroller 36. The volume adjust 266, dual rinse top 263, and two dual rinse bottom 264 devices will be described subsequently in FIGS. 7-9. Further, there is a slide door optical sensor 258 which is input to the slide door switch in line connection and which is used to determine if the front door 256 of the remote device 166 is open. This sensor 258 is used for safety reasons so that, if the front door is open and remains open for five minutes, the slide carousel 24 does not move. Moreover, there is a second optical sensor, the upper level optical sensor 262, which is used to determine if the upper chassis on the remote device 166 has been opened.

Further, as shown in FIG. 6A, the dispense cylinder 282 uses the dispense cylinder extend and the dispense cylinder retract so that the dispense plunger extends and retracts the fluid dispensers. Using air via the system air line, the dispense cylinder 282 is pushed out by using the dispense cylinder extend line. The microcontroller 36 controls the air valves 248A, 248B so that the relay corresponding to the dispense cylinder extend line is activated. In this manner, the dispense cylinder 282 pushes the fluid dispenser down, as described subsequently in FIGS. 12A-12C, thereby dispensing reagent. In order to retract the dispense cylinder 282, the dispense cylinder retract valve 248B is activated using the system air line so that the fluid dispenser is pushed to retraction. Additionally, an extension spring is used to help speed the retraction process, as described subsequently. An optical sensor is used to determine if the dispense is extended, and thereby activated. When the dispense cylinder 282 is extended, the optical sensor is tripped validating that the dispense operation has occurred. Motors 14, 48 move the slide carousel 24 and the reagent carousel 8, and are connected to the slide motor out connection and the reagent motor out connection, respectively. The motors 14, 48 are typically stepper motors.

Sensors 274, 286 are placed in proximity to the slide carousel 24 and the reagent carousel 8 in order to determine the "home" position of each. In the case of the slide carousel 24, the slide carousel home sensor 274 is inductive-type and senses a piece of metal placed underneath the slide designated as the "home" position. When the "home" position is found, the sensor 274 sends a signal to the slide home in line of the microcontroller 36. In the case of the reagent tray 10, the sensor 286 also is an inductive-type of sensor. The reagent tray 10 has a large flat metal ring around the entire tray except for the home position. In this manner, when the sensor 286 senses an absence of metal, this is determined to be the home position thereby indicating to the microcontroller 36, via the reagent home in connection, that the home position is found. The sensor 286 senses the reagent tray 10, rather than the reagent carousel 8, since the user may remove the reagent tray 10. Additionally, since the sensor 286 looks for the absence of metal for the home position, the absence of the reagent tray 10 may be tested by looking for the absence of metal in two consecutive positions.

System pressure is determined via the system air line which directly feeds into a transducer 290. The transducer 290 generates an analog voltage which is proportional to the pressure. The output of the transducer 290 is then sent to an analog to digital converter (ADC) 292 whose output is sent to the microcontroller 36 via the system pressure in connection. Contrary to previous pressure switches which only indicated whether the pressure was below a minimum value, the transducer 290 and ADC 292 combination indicates to the microcontroller 36 the exact pressure. Therefore, the microcontroller 36 can determine both whether the pressure is too low and too high. In either instance, the microcontroller 36 sends an error message and shuts down the run.

As shown in FIG. 6A, the bulk fluid module 230 includes the compressor 232 which pressurizes the air to up to 90 psi. The compressed air is sent to a filter 234 in order to filter out water and other contaminants. Pressure is regulated in a two-step fashion. First, the pressure is regulated at the compressor to approximately 25 psi (±1 psi) via a spring diaphram (prv) 238. The prv 238 is manufactured by Norgren in Littleton, Colo., part number NIP-702 with a plastic bonnet. Second, the pressure is fine-tuned to 13 psi using an air pressure regulator 236. The pressure regulator 236 is very accurate in terms of precise pressure regulation over long periods of time. In this manner, the compressor 232 need not overwork itself since the prv 238 maintains the pressure at the output of the compressor to 25 psi by opening and letting out excess pressure when the pressure exceeds 25 psi. Water and particulates, which are filtered out of the air via the filter 234, are sent to a waste receptacle. The compressed air pressurizes the Liquid Coverslip™ and wash buffer bottles 244, 246 so that when the valves 248F-J are opened corresponding to the Liquid Coverslip™, volume adjust, dual rinse top, dual rinse bottom lines, the pressure is already on the line and the fluid may flow. In addition, the compressed air is used for the dispense cylinder extend line, the dispense cylinder retract line, the mirror air cylinder line, the vortex mixers line, and the bar code blowoff/airknife line. Filters 240 are used at the outputs of the Liquid Coverslip™ and wash buffer bottles 244, 246 in order to remove particulates which may get caught in the valves 248.

The mirror air cylinder line is used to turn the mirror cylinder 278 so that the bar code reader 276 either reads bar codes on the slides of the slide carousel 24 or bar codes on the fluid dispensers on the reagent carousel 8. The output from the bar code reader 276 is input to the microcontroller 36 via the bar code serial I/O connection. In between the valve 248C for the mirror air cylinder line and the mirror cylinder is a flow restrictor 268. The flow restrictor 268 slows the flow of air in the line while still maintaining the 13 psi pressure on the line. In this manner, this moves the mirror slower than would otherwise be done without the restrictor 268.

The vortex mixers 271 likewise operate off of the 13 psi system air line to mix the contents on the slide. The vortex mixers 271 may be used in a single stream or in a dual stream mode. In particular, a single stream of air or a dual stream of air may be used to mix the contents on the slide. Further, restrictors 268 are used in the vortex mixers lines in order to reduce the flow of air. In this manner, when the vortex mixers 271 are used to mix the contents on the slide, the fluid does not blow off the slide and the mixers do not dry any particular spot on the slide.

The bar code blowoff/airknife 267 is used to blow air on the portion of the slide which contains the bar code. In this manner, the bar code is easier to read. Further, fluid can be kept on the slide better due to surface tension if fluid near the edge of the slide is removed.

Figure 6B:
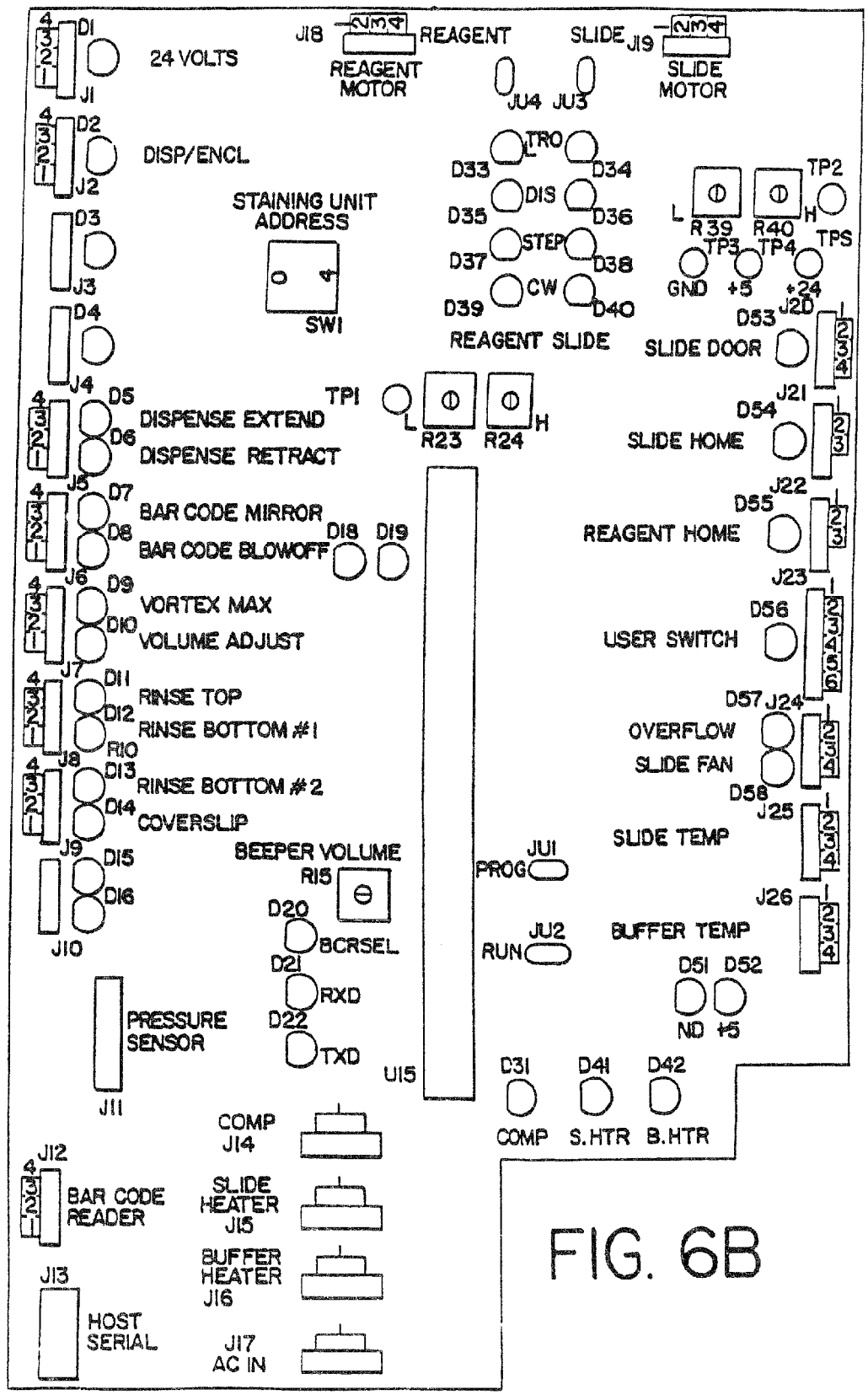
FIG. 6B is a circuit board connection diagram for the microcontroller.

Referring to FIG. 6B, there is shown a circuit board connection diagram for the microcontroller. The sensors and motors for the remote device 166 plug into this board which in turn is in communication with the microcontroller.

Referring to FIG. 7A, there is shown a block diagram of the dual rinse and volume adjust components 263, 264, 266 of the remote device 166 in FIG. 6A. A run is generally executed in a series of steps including the following: reagent is applied to the slide, Liquid Coverslip™ is applied to the slide, the reagent reacts with the tissue on the slide, a different reagent is applied to the slide, Liquid Coverslip™ is applied to the slide, the different reagent reacts with the slide, etc. After the reagent reacts with the slide, but before the next reagent is applied to the slide, the excess reagent which did not react with the sample should be removed from the slide. Otherwise, there is the possibility of having non-specific staining, or background staining, on the slide. This non-specific staining may interfere with the visual analysis of the slide at the end of the run. In order to minimize the non-specific staining, the residual reagent from the previous step is washed from the sample using a wash buffer. Washing may be achieved using a dual rinse device which executes a dual rinse step using a dual rinse top valve 248H and a dual rinse bottom valve 248I, as shown in FIG. 7A. The microcontroller 36 controls the valves so that the wash buffer pulses the slide with the dual rinse top valve 248H and one of the dual rinse bottom valves 248I or 248J consecutively. In particular, during the dual rinse step, the microcontroller 36 turns on the dual rinse top valve 248H, then one of the dual rinse bottom valves 248I or 248J, and so on. As described subsequently, there are two dual rinse bottom valves 248I or 248J in order to achieve the consistency pulse.

Figure 7B:
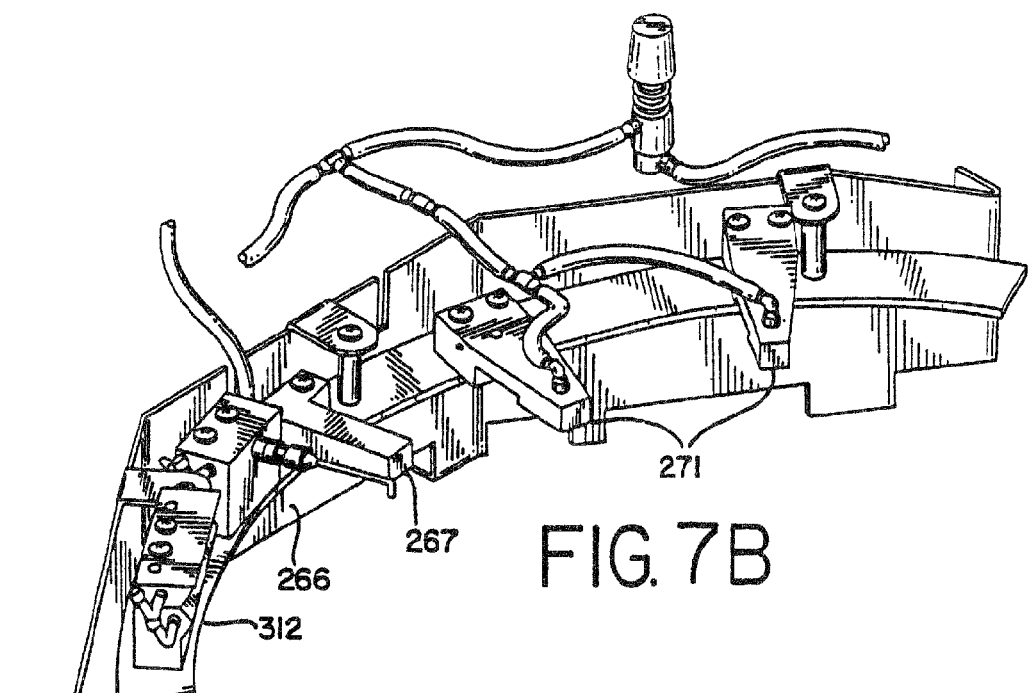
FIG. 7B is a perspective view of the dual rinse top and dual rinse bottom, volume adjust/coverslip, airknife/barcode blowoff and vortex mixers.

Referring to FIG. 7B, there is shown a perspective view of the dual rinse top and dual rinse bottom, volume adjust/coverslip, airknife/barcode blowoff and vortex mixers. The configuration is in the form of a boomerang whereby the boomerang follows the curved portion of the slide carousel 24.

Figure 8A:
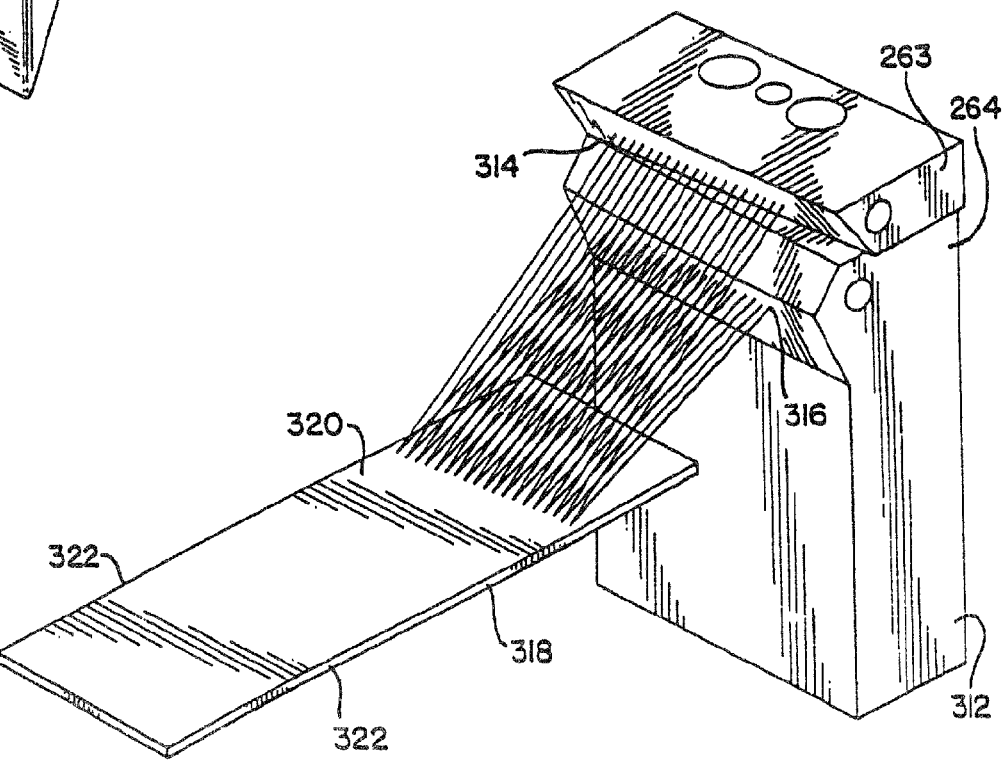
FIG. 8A is a side isometric view of one embodiment of the dual rinse top nozzle and dual rinse bottom nozzle as shown in FIG. 7A.

Referring to FIG. 8A, there is shown a side isometric view of one embodiment of the wash block 312 which employs the dual rinse top nozzle 263 and dual rinse bottom nozzle 264 as shown in FIG. 7A. The wash block 312 comprises a lower set of nozzle outlet openings 316 corresponding to the dual rinse bottom nozzle 264 and an upper set of nozzle outlet openings 314 corresponding to the dual rinse top nozzle 263. In the preferred embodiment, the dual rinse bottom nozzle 264 and dual rinse top nozzle 263 each comprise a plurality of openings. In an alternate embodiment, the dual rinse bottom nozzle 264 and dual rinse top nozzle 263 each comprise a single opening. During the dual rinse step, these openings 314, 316 direct streams of pulsed rinsed fluid towards one or the other of the longitudinal edges 322 of the slide 318. The streams of the pulsed rinsing fluid, from each of the lower and upper sets of nozzle outlet openings 314, 316 preferably impact the slide 318 at the rinse fluid impact zone 320 which is upstream on the slide 318 from the tissue sample (not shown) positioned thereon. Positioning of the wash block 312 is important due to the fragile nature of the tissue sample positioned on the slide. By directing streams of pulsed rinsing fluid at the impact zone 320 of the slide, the rinse fluid is provided with laminar flow by the time the rinse fluid reaches the tissue sample. As a result, undue damage to the fragile tissue sample is prevented.

The upper set of nozzle outlet openings 314 is constructed so that the associated streams of rinse fluid are off-set at an angle from the longitudinal center line of the slide so that the pulsed streams of rinse fluid are directed toward one of the longitudinal edges of the slide 318. The lower set of nozzle openings 316 is constructed so that the associated streams of rinsing fluid are also off-set at an angle from the longitudinal center line of the slide so that the pulsed streams of rinse fluid are directed toward the other one of the longitudinal edges of the slide 318. As a result of this arrangement, pulsed streams of rinse fluid are alternatively and repeatedly directed to one and then the other of the longitudinal edges of the slide.

As shown in FIG. 7A, separate plumbing and valving are provided for each of the lower and upper sets of nozzle outlet openings 314, 316 of the dual rinse top nozzle and dual rinse bottom nozzle 263, 264 to permit independent operation thereof. In operation of the dual rinse step, the wash block 312 directs streams of pulsed rinsing fluid, for example from the lower set of nozzle openings 316 toward a single longitudinal edge of the slide and after completion then directs streams of pulsed rinse fluid, for example from the upper set of nozzle openings 314, to the other longitudinal edge of the slide. This procedure is repeated, via control of the valves 248H-J using the microcontroller 36, and has the effect of rinsing the previous layer of rinse fluid and chemicals off of the slide. The wash block nozzle axis of each of the dual rinse top nozzle and dual rinse bottom nozzle 263, 264 forms an angle with the horizontal of between 15 and 35 degrees, preferably substantially 35 degrees for the dual rinse top nozzle 263 and substantially 25 degrees for the dual rinse bottom nozzle 264, as described in FIGS. 8B and 8C. Moreover, the angle of the slide is substantially horizontal (0.5 degrees to 1.25 degrees) so that the wash buffer both washes the excess reagents off of the slide and also flows off of the slide.

After cleaning the excess reagent off of the slide, a precise amount of wash buffer should be applied to the slide. Ordinarily, 270 μL is the optimal amount of buffer which should be placed on the slide for the next step. In executing the dual rinse step, there is residual wash buffer on the slide; however, the amount of wash buffer left on the slide varies considerably. In order to consistently leave a specific amount of fluid on the slide, the microcontroller 36 executes a consistency pulse.

The consistency pulse consistently leaves an amount of fluid on the slide with variation in amount lower than a shorter pulse, and the consistency pulse cleans the slide of excess reagents.

The consistency pulse is a pulse of wash buffer which is executed for a longer period of time than the individual pulses of the dual rinse step. To send wash buffer onto the slide, the tubing containing the wash buffer is pressurized. Because of this pressure and because of the turning on and off of the wash buffer valves 248H-J, there is a pressure wave effect generated in the wash buffer tubing (i.e., there are "reflections" with a certain frequency that travel through the tubing based on, among other things, the length and geometry of the tubing). Therefore, one cannot consistently determine where one is on the wave. Because of this wave effect, the amount of pressure that the pulse has varies so that the amount of buffer left on the slide varies as well. In order to minimize the wave effect, the consistency pulse turns the valve on for a period of sufficient time and/or for a sufficient strength in order to let the wave effect minimize within the tubing. This sufficient amount of time amounts to a few periods of the frequency of the reflected wave. Since the reflected wave is a decaying sinusoid, after a few periods, the wave is no longer a factor in the consistency pulse. The consistency pulse is therefore an extended burst of either the dual rinse top nozzle 263 or the dual rinse bottom nozzle 264 for a period longer than the dual rinse step. For example, as describe in FIG. 9 in more detail below, the period for a pulse during the dual rinse step is 60 mSec whereas the period for the consistency pulse is 300 mSec.

Moreover, in order for the consistency pulse to leave a consistent amount of fluid on the slide, the momentum of the consistency pulse should be greater than that during the dual rinse step. In the preferred embodiment, the increase in momentum of the pulse is achieved by increasing the volume of wash buffer flow using two dual rinse bottom valves 248I and 248J, as shown in FIG. 7, as opposed to using only one dual rinse valve 248I or 248J during the dual rinse step. In this manner, the stream of wash buffer with an increased momentum is sent across the slide with the result that the residual volume of buffer left on the slide after the consistency pulse is lower and also has a lower variation. If a pulse of lower momentum is used, more solution is left on the slide due to interaction with the surface tension of the slide. In an alternative embodiment, the increase in volume and subsequent increase in momentum for the consistency pulse may be achieved using a valve which has an opening which is larger than the opening of the valves 248H-J used during the dual rinse step. The consistency pulse therefore has a strong flow out of the nozzle, generating a laminar, not turbulent, flow on the slide. The laminar flow then washes off the slide, consistently leaving an amount of fluid on the slide. Moreover, the consistency pulse is consistent, not only from run to run on an individual machine, but also from machine to machine as well. Therefore, machine may be interchanged without the need for recalibrating the system to determine the amount of buffer left on the slide.

Further, when both a consistent and a minimal amount of buffer is desired to be left on the slide, the dual rinse bottom nozzle 264 should be used rather than the dual rinse top nozzle 263. The angle of the dual rinse bottom nozzle 264 is less than the angle for the dual rinse top nozzle 263; therefore, the less steep the angle, the more likely the buffer will flow off of the slide, not interacting with the surface tension of the slide. For example, using a dual rinse top nozzle 263 with a single valve leaves approximately 275±40 μL on the slide whereas using a dual rinse bottom nozzle 264 with a dual valve leaves approximately 180±20 μL on the slide.

With varying the time of the pulse, the angle of the pulse, and the momentum, the consistency pulse may be used in several ways. The first way is for the consistency pulse to leave a minimal amount of wash buffer on the slide with minimal variation from run to run and machine to machine (180±20 μL) for any given instrument. In particular, this variation of ±20 μL is across all machines so that, in the event that one machine must be replaced by a second machine, the variation is small enough so that the amount of fluid left on the slide is within acceptable parameters. Moreover, the variation from run to run within a single machine is approximately ±10 μL; therefore, once the machine is calibrated (and the amount of volume dispensed from the volume adjust, as discussed subsequently, is determined to achieve a total volume of 270 μL), the fluid on the slides for a particular machine does not vary significantly run to run.

The modification of the consistency pulse is done by using a time longer than the individual dual step pulse, the dual rinse bottom nozzle 264, and the two valves 248I and 248J; after the consistency pulse step, the required amount of buffer on the slide (as determined by experiment) may be added using the volume adjust 266, which is described subsequently, with extreme precision.

Apart from using the consistency pulse to leave a minimal amount of buffer on the slide, the consistency pulse may be used to leave an amount greater than a minimal amount, while still having a low variation in the amount left on the slide. For example, the operator may adjust the amount of momentum of the pulse, the duration of the pulse, the angle of the outlet nozzle with respect to the slide, and the angle of slide with respect to horizontal. As one example, the outlet of the nozzle may be designed with an angle which is less than the angle of the dual rinse bottom nozzle. In this manner, the operator may tailor the amount left on the slide depending on the amount and variance of the buffer necessary for the experiment.

After the consistency pulse, if additional buffer is necessary to be placed on the slide to run the experiment, the volume adjust is used, as shown in FIGS. 7A and 7B. The microcontroller 36 turns on the valve 248G for the volume adjust line to place buffer on the slide. As described previously, the volume adjust line has a restrictor 268 which reduces the volume flow of the wash buffer through the line. This is done so that the buffer does not disturb the tissue on the slide since the needle of the volume adjust nozzle 388 is directly above the slide and the wash buffer is dropped onto the slide. A precise amount of buffer is able to be placed on the slide. This is based on the amount of pressure in the wash buffer bottle, the amount of time the valve 248G for the volume adjust line is open, and the amount of flow through the restrictor 268. Based on these parameters, the amount of volume placed on the slide may be adjusted by changing the dial nozzle which controls the amount of time the valve for the volume adjust line is open. In the alternative, the amount of time the valve is open may be adjusted using a potentiometer.

In operation, the volume adjust 266 is more accurate when it is turned on for more than 60 mSec. Operating the volume adjust 266 less than 60 mSec makes the dispensing of the buffer less accurate. This is due to the fact that the turning on and off of the valves, which is controlled by the microcontroller, is interrupt driven. There is a window of accuracy of approximately 10 mSec when turning on/off the valves (e.g., if the volume adjust 266 is to be turned on for 50 mSec, the actual time in which the valve for the volume adjust is turned on is between 40 mSec and 50 mSec). Therefore, when designing a system which combines both the consistency pulse with the volume adjust, the consistency pulse should leave a volume of fluid on the slide low enough so that the volume adjust may be turned on for more than 60 mSec (which is determined to be the minimal amount of time in which the accuracy of the volume adjust is acceptable). In order to accomplish this, the consistency pulse is designed to leave a minimal amount of fluid on the slide by using the dual rinse bottom nozzle 264 and the two valves 248I and 248J. In practice, after the consistency pulse using the dual rinse bottom nozzle 264 and the two valves 248I and 248J, there is 180±20 µL. By turning on the volume adjust for approximately 100 mSec, the volume on the slide is increased to approximately 270 µL.

Figure 8D:
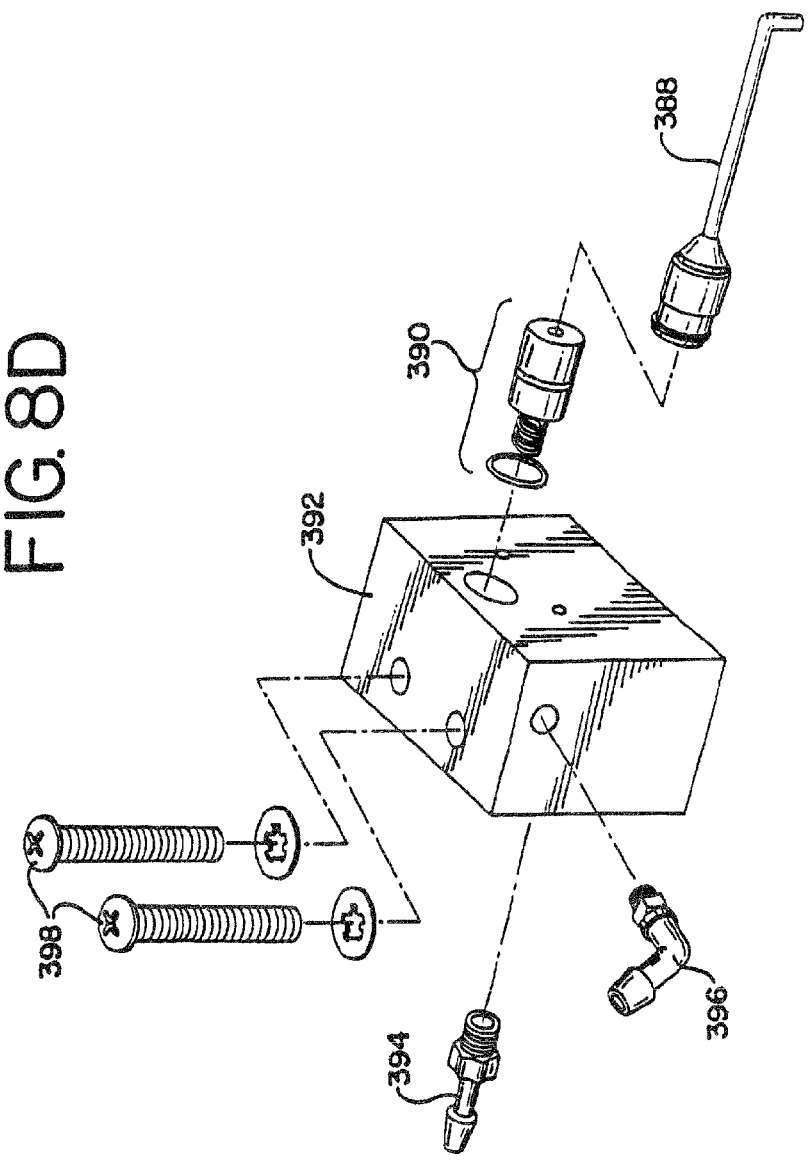
FIG. 8D is a side view of one embodiment of the volume adjust as shown in FIG. 7A.
Figure 8B:
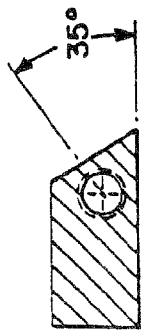
FIG. 8B is a side view of the angle of the dual rinse top nozzle as shown in FIG. 8A.
Figure 8C:
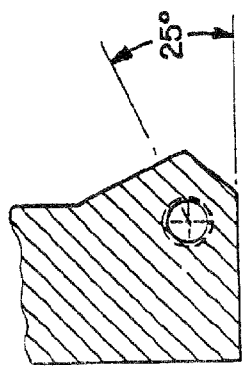
FIG. 8C is a side view of the angle of the dual rinse bottom nozzle as shown in FIG. 8A.

Referring to FIGS. 8B and 8C, there are shown side views of the angles of the dual rinse top nozzle 263 and dual rinse bottom nozzle 264, respectively, as shown in FIG. 8A. Note that both FIGS. 8B and 8C are positioned upside down for ease of reference of the angles of the nozzle openings. The angle, as described previously, is 35 degrees from the horizontal for the outlet of the dual rinse top nozzle (263) is 25 horizontal for the outlet of the dual rinse bottom nozzle (264). These angles may be varied in order to modify the amount and/or variation of fluid left on the slide after the consistency pulse.

Referring to FIG. 8D, there is shown a side view of one embodiment of the volume adjust as shown in FIG. 7A. The needle 388 of the volume adjust is composed of a stainless steel with a 90 degree needle. Fluid therefore goes at a downward angle and drops onto the slide, thereby allowing for greater control of the placement of the fluid. The connector pieces which connect the needle 388 to the acrylic block 392 of the volume adjust are also composed of stainless steel. The stainless steel is used since it does not react with the wash buffer. At the back of the acrylic block 392 is a connector 394 which connects to the volume adjust line of FIG. 6A. At the side of the acrylic block is a connector 396 which connects to the Liquid Coverslip™ line of FIG. 6A.

Figure 9A:
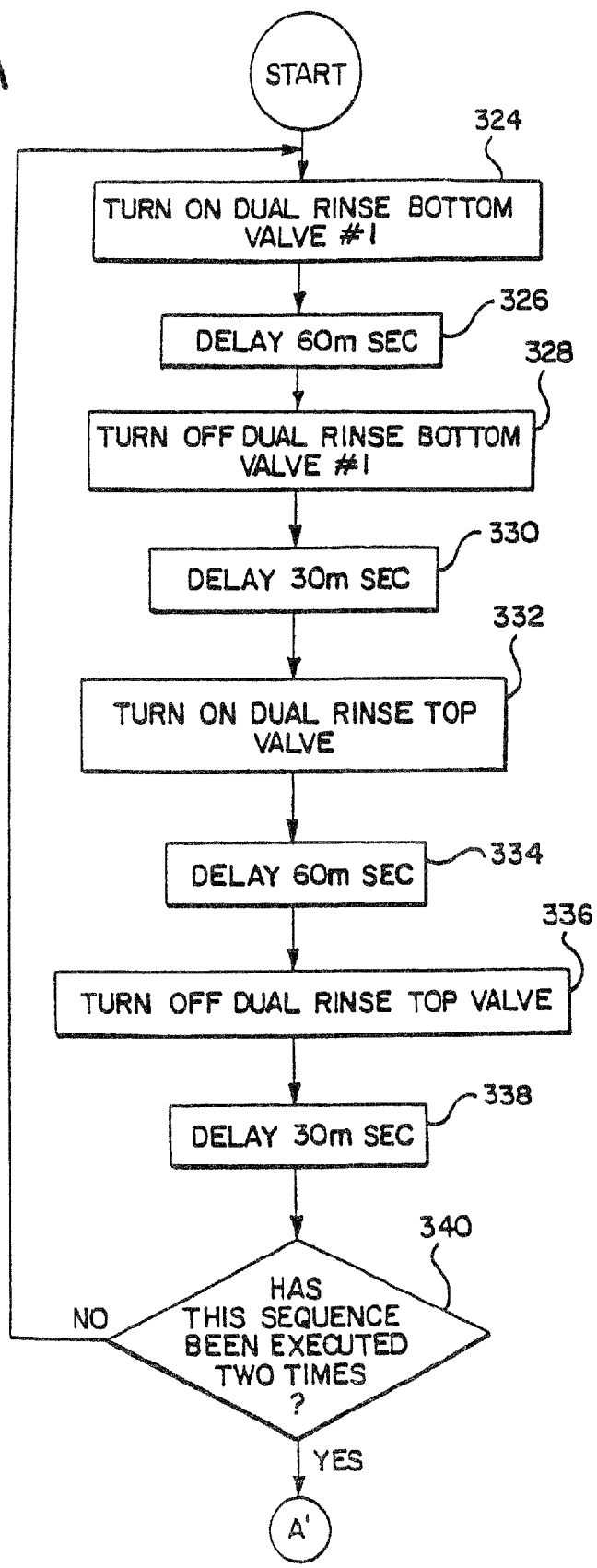
FIGS. 9A, 9B, and 9C are flow charts of the dual rinse, the consistency pulse and the volume adjust steps.
Figure 9B:
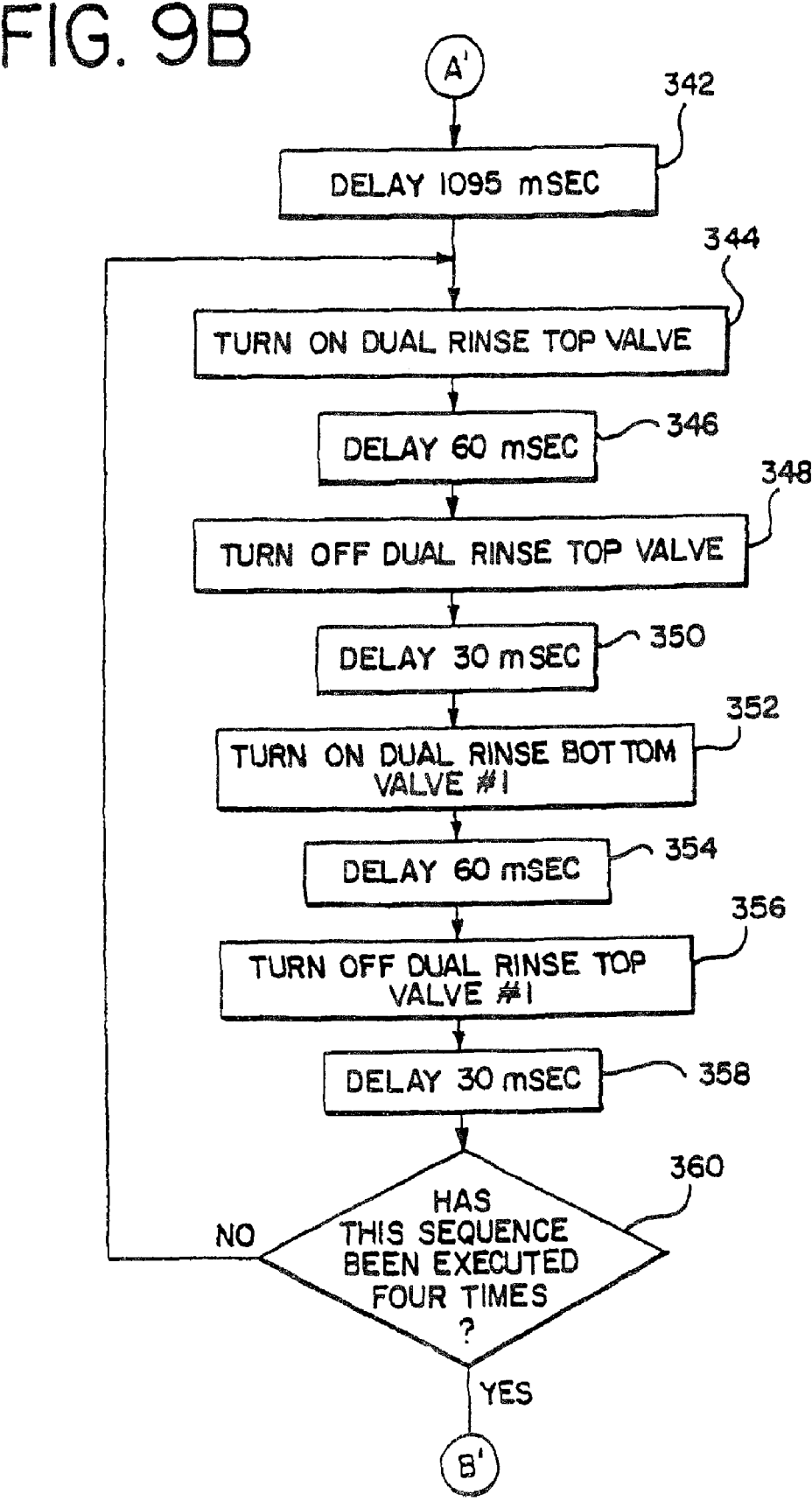
Figure 9C:
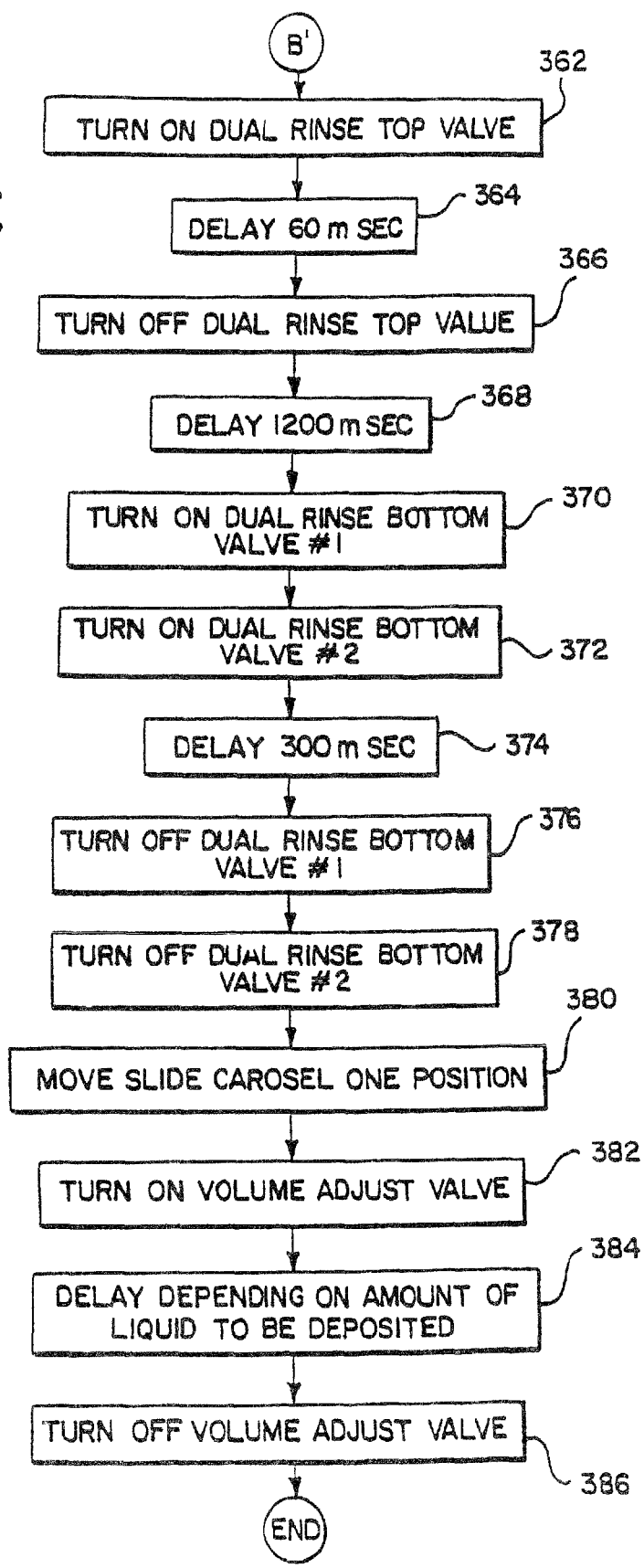

Referring to FIG. 9, there is shown a flow chart of the dual rinse, the consistency pulse and the volume adjust steps. For the dual rinse step, one of the dual rinse bottom valves (248I or 248J) is first turned on 324, the microcontroller 36 waits for 60 mSec 326, and the dual rinse bottom valve (248I or 248J) is turned off 328. The microcontroller 36 then delays for 30 mSec 330. The dual rinse top valve (248H) is then turned on 332, the microcontroller 36 waits for 60 mSec 334, and the dual rinse top valve (248H) is turned off 336. The microcontroller 36 then delays for 30 mSec 338. This sequence is repeated two times 340. Then, the microcontroller 36 waits 1100 mSec 342. Then, the dual rinse top valve (248H) is turned on 344, the microcontroller 36 waits for 60 mSec 346, and the dual rinse top valve (248H) is turned off 348. The microcontroller 36 then delays for 30 mSec 350. One of the dual rinse bottom valves (248I or 248J) is first turned on 352, the microcontroller 36 waits for 60 mSec 354, and the dual rinse bottom valve (248I or 248J) is turned off 356. The microcontroller 36 then delays for 30 mSec 358. This sequence is repeated four times 360. Then the dual rinse top valve (248H) is turned on 362, the microcontroller 36 waits for 60 mSec 364, and the dual rinse top valve (248H) is turned off 366. The microcontroller 36 then waits 1200 mSec 368.

In the preferred embodiment, the dual rinse step begins with a bottom-top, bottom-top rinse cycle, and then a top-bottom, top-bottom, top-bottom, top-bottom rinse cycle. In this manner, the slide is cleaned better. This switching of the dual rinse step, starting with one set of nozzles (in the preferred embodiment, the dual rinse bottom valve), and in the next step, starting with the other set of nozzles (in the preferred embodiment, the dual rinse top valve), allows for quicker cleaning of the slide while using less buffer. Depending on the rinsing needs of the slides, the number of pulses (top-bottom or bottom-top) and the amount of buffer sent in the pulses are varied. Rinsing removes excessive reagent in the slide and the tissue, which in turn will reduce the background staining on the slide and aid in analysis of the slide.

By experimentation, 6.5 to 7.5 mL of buffer should be used in the dual rinse step. More than 7.5 mL in the dual rinse step uses an excessive amount of buffer (i.e., one may run out of buffer during a staining run), and may limit the amount of dual rinse steps performed in one run. Moreover, by experimentation, the dual rinse step should end by using the bottom valve and bottom nozzle. This is so that, the consistency pulse, which also uses the bottom valves, is run more consistently.

For the consistency pulse step, both the dual rinse bottom valves (248I and 248J) are turned on 370, 372, the microcontroller 36 then delays 300 mSec 374, and both the dual rinse bottom valves (248I and 248J) are turned off 376, 378. For the volume adjust step, after the slide carousel 24 is moved one position 380, the valve 248G for the volume adjust line is turned on 382. The microcontroller 36 waits, depending on the amount of fluid to be deposited on the slide 384. Then, the valve (248G) for the volume adjust line is turned off 386. Delays in between the dual rinse step, consistency pulse step, and volume adjust step are inserted in the steps above in order to minimize the possibility of having too many valves on in the system at the same time. If this occurs, this drops the pressure and, in turn, reduces the force of fluid of wash buffer and Liquid Coverslip™.

Figure 10:
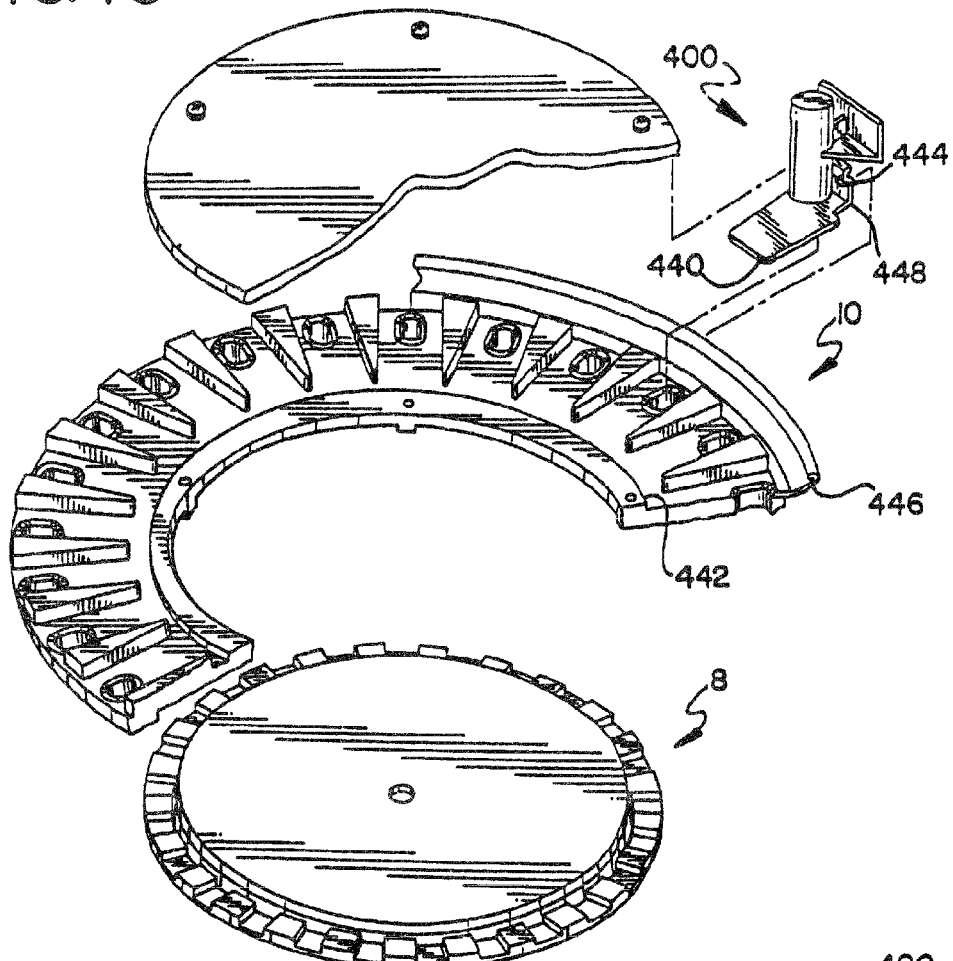
FIGS. 10 and 11 illustrate the mounting of a fluid dispenser on a reagent tray and the manner in which a reagent tray is engaged with a drive carousel.
Figure 11:
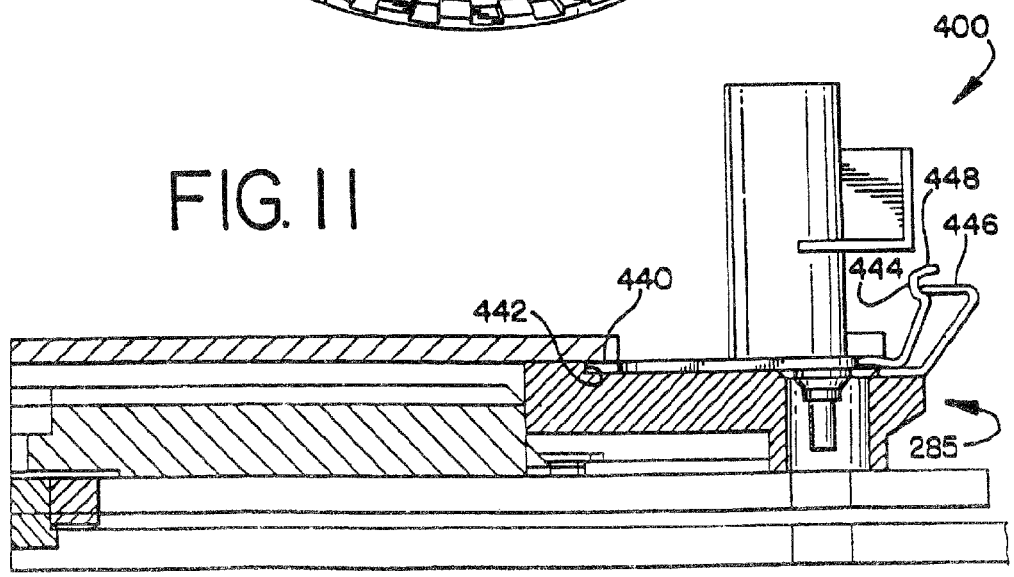

FIGS. 10 and 11 illustrate the manner of mounting a fluid dispenser 400 in a reagent tray which is engaged in the reagent carousel 8. The foot 440 is initially inserted into a circular U-shaped groove 442 formed in the reagent tray 10. In an alternative embodiment, the foot is inserted into a rectangular shaped groove. Groove 444 of spring member 448 engages a circumferential lip 446 of the reagent tray 10. FIG. 11 shows a cross sectional view of the fluid dispenser 400 after it has been mounted on the reagent tray 10 showing in particular the manner in which foot 440 fits into groove 442 and showing the flexing of spring member 448 to hold the fluid dispenser 400 firmly in place. To remove the fluid dispenser 400, spring member 448 is simply bent inward slightly so that the groove 444 clears the lip 446, and the foot 440 is withdrawn from groove 442.

Referring to FIG. 12A, there is shown an elevational cutaway view of a prefilled fluid dispenser 400 in the extended position. FIG. 12B shows an elevational cutaway view of a user fillable fluid dispenser 400 in the extended position. The main difference between the prefilled and customer fillable dispensers is the substitution of a flip cap 402 to replace the snap cap 404. The fluid dispenser 400 has a reservoir chamber 410, which stores the fluid, and a dispense chamber 412, whereby the reservoir chamber 410 is above the dispense chamber 412. The reservoir chamber 410 is substantially in line with the dispense chamber, and in the preferred embodiment, coaxial with the dispense chamber 412.

Previous liquid dispensers had a side by side arrangement whereby the reservoir chamber was to the side of the dispense chamber. In this configuration, the reservoir chamber was smaller and therefore held less fluid. In the present invention the reservoir chamber can be enlarged thereby holding more fluid. For example, in previous dispensers, the reservoir chamber could hold approximately 27.5 mL of fluid whereas, in the present invention, the reservoir chamber can hold approximately 34.0 mL of fluid. Ordinarily, a single dispenser is rated to give 250 shots (i.e., 250 dispenses of fluid). In order to provide the 250 shots in the previous dispensers, different types of couplers, depending on different types of reagents had to be made. This was due, in part, to the limited capacity of the reservoir chamber and to the thickness of the fluids (some fluids dispense different amounts based on the viscosity of the fluid). Because of the increased capacity of the reservoir chamber in the present invention, the dispenser can provide 250 shots, regardless of the viscosity of the fluid, so that different couplers are not necessary.

Moreover, previous fluid dispensers which included a reservoir chamber 410 that was to the side of the dispense chamber 412 required a connecting or horizontal section which connected the reservoir chamber 410 with the dispense chamber 412. In addition to potential problems of clogging of the horizontal section, the previous design was more difficult to manufacture. In particular, the side-by-side design required that the molding process of the horizontal or connecting piece be carefully controlled so that all sides of the connecting piece interact correctly with the reservoir chamber 410, the dispense chamber 412, and the ball chamber 432 and nozzle 430. As described subsequently, the ball chamber 432 includes a ball 426 which seats in the upper part of the ball chamber 432 during a portion of the operation of the fluid dispenser 400. In previous designs, the coupler was formed via a T-shaped chamber, i.e. a horizontal chamber abutting two vertical pieces. At the intersection of the pieces, the ball seat area was formed. In manufacturing this coupler, the consistency of the T-shaped piece varied so that the ball seat area was, at times, difficult to manufacture properly. In the present invention, the fluid dispenser 400 requires no horizontal connecting portion between the reservoir chamber 410 and the dispense chamber 412. The reservoir chamber 410 is on top of dispense chamber 412 and, in the preferred embodiment, the reservoir chamber 410 is coaxial with the dispense chamber 412. Since the flow is substantially in one line or vertical, the T-shaped piece is removed. Moreover, the ball seat area is replaced by a check valve ball insert 424 which is a separate and smaller molded piece, and therefore can be controlled, from a manufacturing standpoint, better than in previous designs.

In the preferred embodiment, the reservoir chamber 410 shape is as shown in FIGS. 12A and 12B. The reservoir shape may also be funnel-like or any other shape which drains the fluid through the connecting means between the reservoir chamber 410 and the dispense chamber 412. The connecting means between the reservoir chamber 410 to the dispense chamber 412 in the preferred embodiment is a valve, such as a duckbill check valve 416 which has a means to sense pressure differentials. The duckbill check valve is manufactured by Vernay Laboratories, Inc. in Yellow Springs, Ohio, part number X6597-E. In alternate embodiments, the connecting means is any device which transfers fluid in one direction (from the reservoir chamber 410 to the dispense chamber 412) and which passes fluid based on a pressure differential. This includes using an umbrella valve or the cup check valve 792 as described in FIGS. 20-21.

Fluid is ejected from the dispense chamber 412 by exerting a downward force on the cap, against the force of the compression spring 418. This forces the barrel 408 downward until it reaches the stop 420 which prevents the barrel 408 from further downward movement, as shown in FIG. 12C. When the fluid dispenser 400 is mounted on a reagent tray 10, as described in FIGS. 10 and 11, the downward force on the cap 404 is applied by the dispense cylinder extend air line, as described in FIG. 6A, or by some other means to push the barrel 408 downward. The downward movement of the barrel 408, including the lower portion of the barrel which acts as a piston, expels fluid from the dispense chamber 412.

Figure 13A:
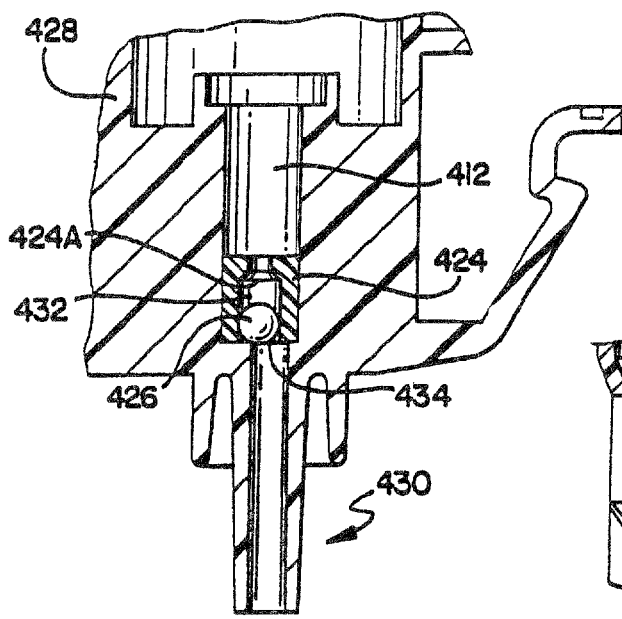
FIG. 13A is a cutaway view of the ball chamber and nozzle.

As the spring 418 expands, the barrel 408 moves upward and the ball 426 moves upward as well. Referring to FIG. 13A, there is shown a detailed view of the ball chamber 432 and nozzle 430. The coupler 428 is formed where a hole in the coupler is offset for ball chamber 432 so that an inner edge of nozzle 430 protrudes into the outlet of ball chamber 432. Ball chamber 432 contains a ball 426 which fits loosely against the cylindrical surface of ball chamber 432 and is free to move between an uppermost position and a lowermost position. In its uppermost position, ball 426 mates with the ball check valve insert 424, thereby preventing fluid flow in the direction from nozzle 430 to dispense chamber 412. At its lowermost position, the ball 426 is restrained by inner edge of nozzle 430 and prevented from falling into nozzle 430. This does not prevent fluid from flowing from ball chamber 432 to nozzle 430, however.

Using the above described structure as a basis, the operation and unique characteristics of fluid dispenser 400 will now be described. At the beginning of a dispense stroke, the fluid dispenser 400 is in the positions shown in FIGS. 12A and 12B. When fluid is to be dispensed, a downward force is applied against cap 402. This overcomes the force of compression spring 418 and forces the barrel 408 downward until it reaches the top of the stop 420, thereby dispensing a predetermined volume of liquid equal to approximately 100 μL. This is equal to the liquid volume of the area that the barrel 408 moves down minus the "suck back" (which is the amount of fluid that travels past the ball on the upstroke of the barrel 408 before the ball 426 shuts off the flow). The fluid flows from dispense chamber 412 into ball chamber 432. The downward flow through ball chamber 432 forces ball 426 to its lowermost position, abutting edge 434, but this does not prevent flow in this direction and the measured amount of fluid is ejected from nozzle 430.

When the barrel 408 has reached its lower extreme position, the downward force on cap 402 is released, by the microcontroller 36 actuating the valve 248B for the dispense cylinder retract air line, as described in FIG. 6A, and compression spring 418 takes over, forcing barrel 408 and cap 402 in an upward direction. Fluid begins to be sucked into dispense chamber 412, which was described previously as the "suck back."

It is here that the interplay of ball check valve insert 424 and ball 426 in the ball chamber 432 is described. The ball 426 moves freely within ball chamber 432, and therefore provides essentially no resistance to fluid flow from nozzle 430 until it reaches its sealing position at the ball check valve insert 424. When the dispenser operation is completed, the fluid flow has forced ball 426 to its lowermost position, abutting edge 434. As the upward movement of the barrel 408 begins to draw fluid back into dispense chamber 412, the upward flow of fluid in ball chamber 432 pulls ball 426 upward until it reaches ball check valve insert 424, where it cuts off any further fluid flow toward dispense chamber 412. Until ball 426 reaches the ball check valve insert 424, however, there is virtually no resistance to fluid flow from nozzle 430, and therefore no pressure differential is created across duck bill check valve 416 sufficient to cause fluid flow from reservoir chamber 410 to dispense chamber 412.

The volume of fluid which flows from nozzle towards dispense chamber 412 ("suck back") while ball 426 is moving from its lowermost to its uppermost position is preselected to be a volume equal to the volume of the hanging drop left at tip at the end of the dispense cycle. Thus, the drip is effectively drawn back into nozzle 430 and an internal meniscus forms at tip.

When ball 426 reaches the ball check valve insert 424, it shuts off further flow from nozzle 430 into dispense chamber 412. This immediately creates a pressure differential across duckbill check valve 416 and causes fluid to flow from reservoir chamber 410 into dispense chamber 412. The suction generated in dispense chamber 412 keeps ball 426 firmly seated against the ball check valve insert 424 and prevents any further flow from nozzle 430. When compression spring 418 has forced barrel 408 upward, as shown in FIGS. 12A and 12B, the fluid dispenser 400 is ready for another dispense cycle. When the pressure differential is at equilibrium, the ball 426, being made of a material slightly more dense than the liquid, falls through ball chamber 432 until it make contact again with edge 434.

Figure 13B:
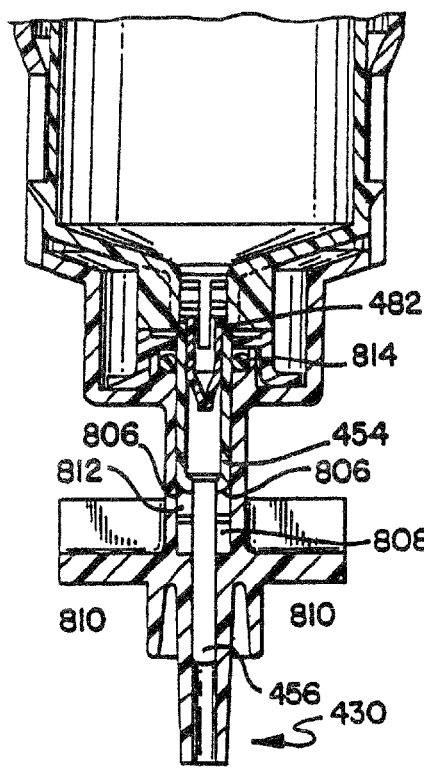
FIGS. 13B and 13C are front and side cutaway views of the lower portion of the barrel with an extension section.
Figure 13C:
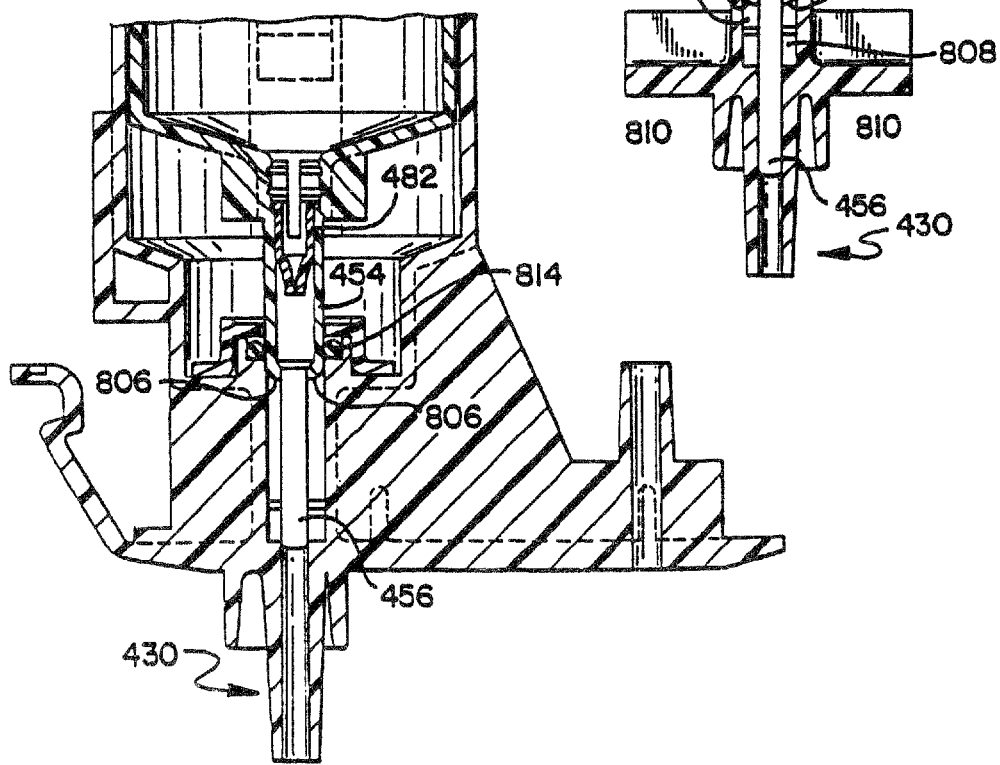

Referring to FIGS. 13B and 13C, there is shown a front and side cutaway of the lower portion of the fluid dispenser 400, respectively, in an alternative embodiment of the invention wherein the ball check valve insert 424 and ball 426 are removed. In order to retract a hanging drop from the edge of the nozzle 430, the piston 454 on the end of the barrel 408 has an extension piece 456 connected to it. In this manner, when the barrel 408 is raised upward, the extension piece 456 moves upward as well, thereby retracting any drops on the edge of the nozzle 430. In particular, FIG. 13B shows the barrel is in the down position.

There are holes 806 where the extension piece is attached to the bottom of the piston 454. In an alternate embodiment, the piston 454 has a single hole 806. When the piston rides down, the O-ring 810 is a tight fit with the extension piece so that the O-ring 810 travels with the extension piece. Because the O-ring 810 is not flush with the chamfer 808 (which is a cone shaped), fluid in the dispense chamber can flow down around the back side of the O-ring 810 and out through the nozzle 430. A second O-ring 814 takes the place of the quad seal 422, as shown in FIGS. 14A-14B.

On the upstroke, the O-ring 810 travels with the extension piece 454, which is attached to the piston 454, until the O-ring 810 seats against the chamfer 808. In this manner, the extension piece 454 acts as a piston extension. The chamfer 808 is housed inside the O-ring insert 812 and is fixed during movement of the piston. The O-ring insert 812 is connected to the coupler 428. When the O-ring 810 seats in the chamfer 808 (closing off any flow), there is a vacuum created in the dispense chamber 412, which creates the pressure differential to dispense fluid into the dispense chamber 412 through the check valve 482. Simultaneously with the upstroke, the fluid travels with the extension piece 454, and the drop at the end of the tip of the dispenser travels with the fluid due to surface tension. Therefore, the hanging drop is pulled back into the nozzle 430. Moreover, with the barrel 408 in the up position, fluid does not travel through the holes 806 due to the O-ring 810 seating inside the chamfer 808. In this embodiment, the ball and ball check valve insert is not necessary.

Referring to FIGS. 14A and 14B, there are shown exploded views of a cutaway of a prefilled and user tillable fluid dispenser 400, respectively. Differences between the prefilled and the user fillable fluid dispensers include: (1) the snap cap 404, as shown in FIGS. 14A and 14B; the barrel 408 being transparent in the user fillable fluid dispenser; and (3) the lack of an evaporation ring 405 in the user fillable fluid dispenser. Fluid can be filled into the reservoir through a fill hole and subsequently closed using a snap cap 404 in order to close the system. For prefilled fluid dispensers, the snap cap 404 is permanently attached over the fill hole after filling. The fill hole and the snap cap 404 are matched using a luer fitting design in order to be a tight seal, as shown in FIG. 16. The user fillable fluid dispenser 400 utilizes a living hinge design and luer slip design between the fill hole and the flip cap 402. The cap 406, as previously described, is sonically welded to the barrel 408. The cap 406 also has a vent 460, which is described subsequently with respect to FIG. 16. The duckbill check valve insert 414 holds the duckbill check valve 416 in place and creates a seal so that fluid cannot drip either from the dispense chamber 412 to the reservoir chamber 410 or from the reservoir chamber 410 to the dispense chamber 412. Further, the duckbill check valve insert 414 has a protrusion, or a nipple, which holds the duckbill to it for ease of assembly, as shown in more detail in FIG. 17B. The duckbill check valve 416, which serves as a check valve, is snapped to the duckbill check valve insert 414. The duckbill check valve 416 is a one way valve with a high cracking pressure of between 0.6 to 3.0 psi. This acts to hold the fluid in the reservoir chamber 410 since the cracking pressure is greater than the head pressure of fluid in the reservoir chamber 410. And, the duckbill passes fluid from the reservoir chamber 410 to the dispense chamber 412 on the upstroke of the barrel 408 while preventing fluid to pass during the downstroke of the barrel 408. The duckbill check valve 416 and duckbill check valve insert 414 are seated in the lower portion of the barrel 408 as shown in FIG. 17A.

Figure 17A:
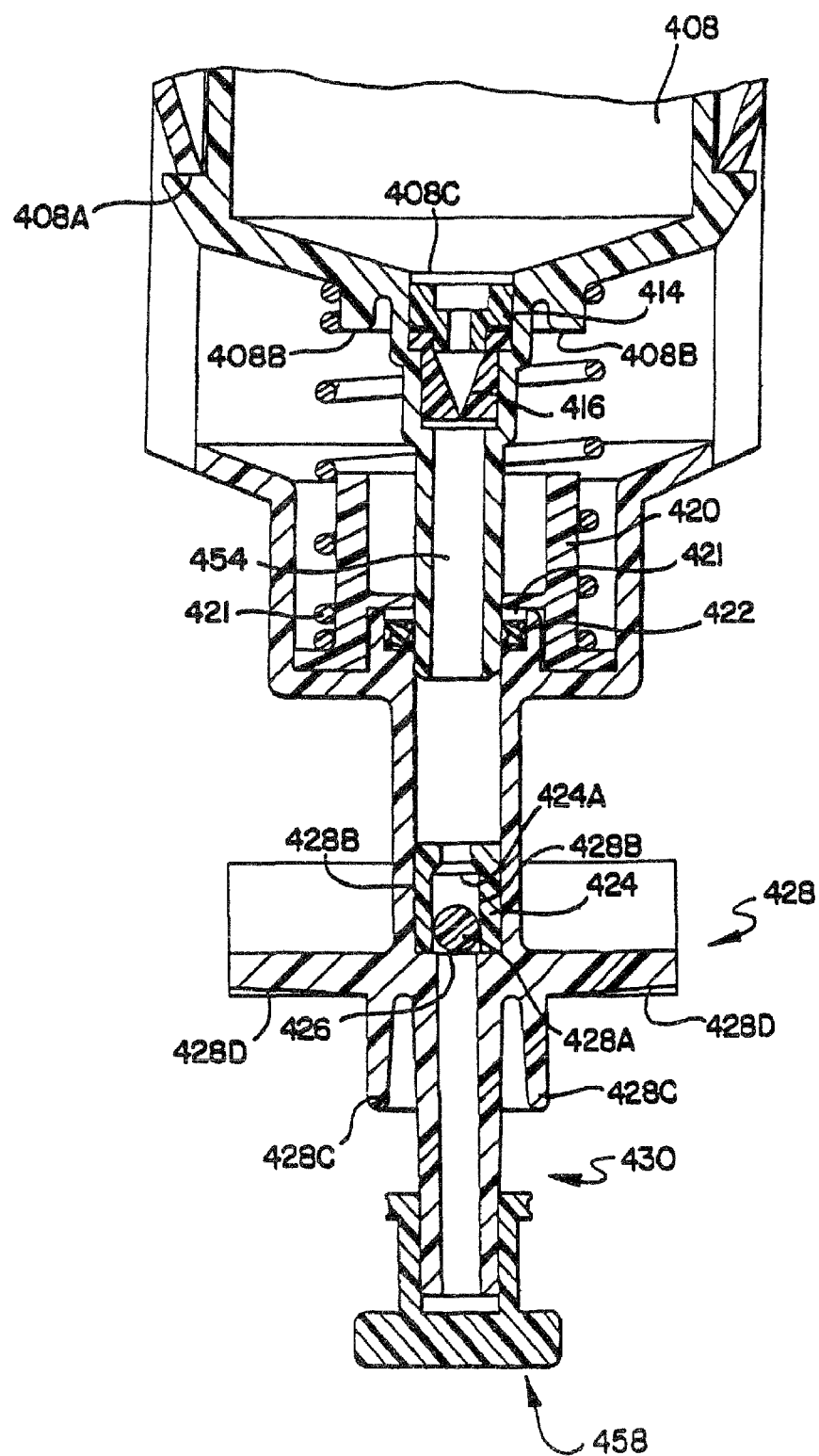
FIG. 17A is a cutaway view of the lower portion of the barrel, duckbill check valve, duckbill check valve insert, quad seal, ball, ball check valve insert and coupler of a fluid dispenser.
Figure 17B:
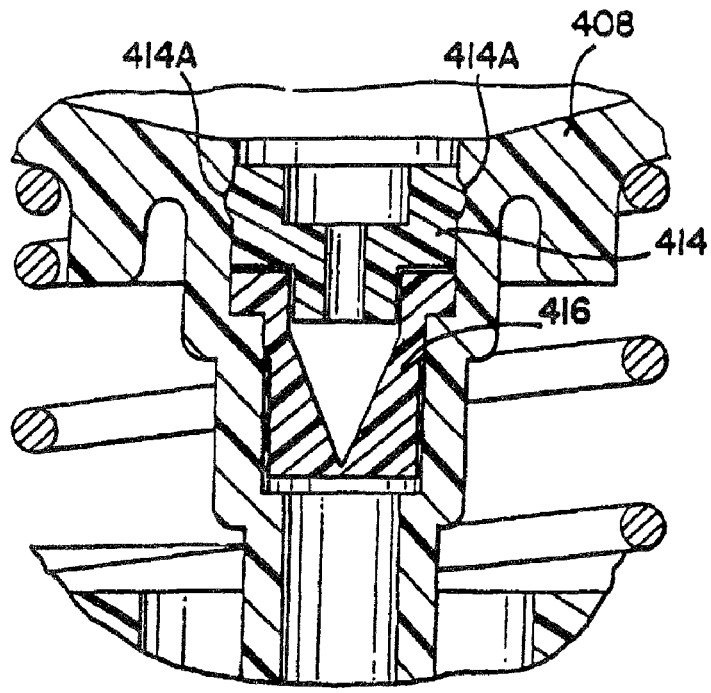
FIG. 17B is a cutaway view of the lower portion of the barrel, duckbill check valve, duckbill check valve insert of a fluid dispenser.
Figure 17C:
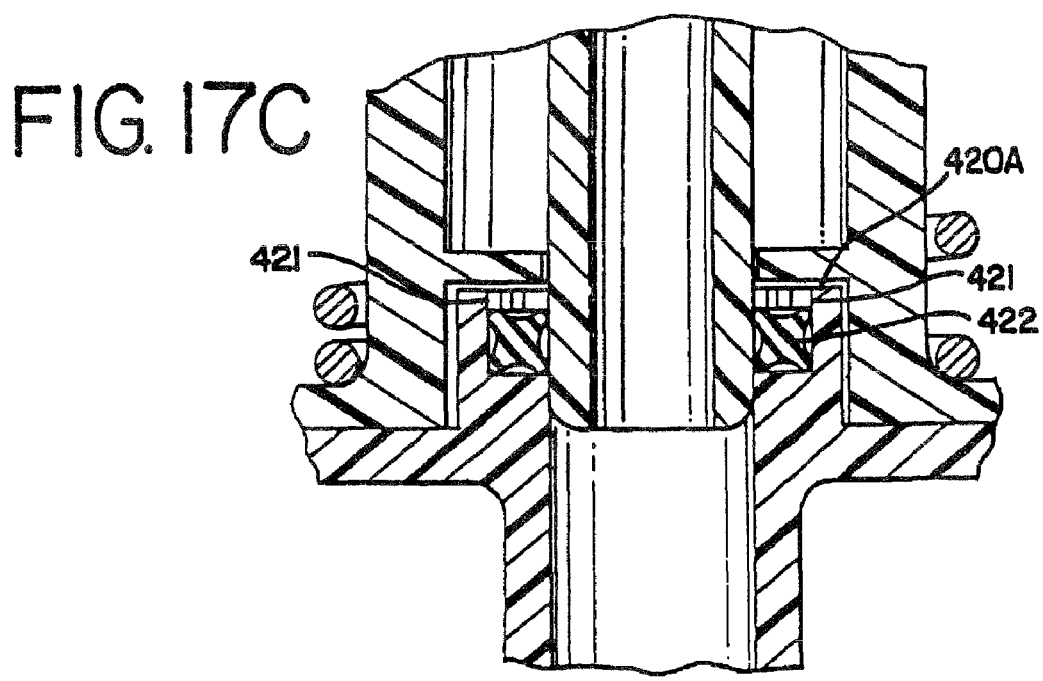
FIG. 17C is a cutaway view of the quad seal of a fluid dispenser.

The spring 418 is a compression spring which expands and contracts based on the movement of the barrel 408. The stop 420, as described previously, stops the downward stroke of the barrel 408. The stop also holds the quad seal 422 in place during movement of the fluid dispenser 400 and composed of polypropylene. The stop 420 is held in place based on the compression spring 418 with the force varies based on the movement of the barrel 408. The stop 420 is held in place, in turn, keeps the quad seal 422 in place via a ledge 420A, as shown in FIG. 17C, on the stop 420. The quad seal 422 ensures that the fluid dispenser 400 is always a closed system thereby keeping the fluid dispenser 400 primed. The quad seal 422 is made of Viton™ rubber that is a fluoroelastomer, and is distributed by Lutz Sales, in Hanover Park, Ill., part number QS-008-2799. The ball check valve insert 424 is a separate part from the coupler 428 and is seated inside the coupler 428, being snapped into place by grooves in the chamber of the coupler 428 and by being seated on a ledge 428A, as shown in FIG. 17A. The ball check valve insert 424 has a ball seat 424A on the inside with which to engage the ball 426 on the upstroke of the barrel 408. Previous fluid dispensers integrated the coupler with the ball check valve insert for the ball. However, manufacturing of the coupler integrating those functions was difficult due to the fact that 3 pins, at the positions of 12:00, 3:00 and 6:00, had to come together and not distort the ball check valve insert. Therefore, processing is simplified by separating the ball check valve insert 424 from the coupler 428. The inner cavity 432 of the ball check valve insert 424, which engages the ball 426, may then be manufactured more easily. The ball 426 is made of borosilicate (which is a type of glass). In an alternative embodiment, a ball 426 composed of rubber may be used. In certain instances, a rubber ball may seat better in the plastic ball check valve insert 424, provided there is no chemical interaction of the rubber ball with the reagents.

Assembly and filling of the fluid dispenser 400 is simple based on the invention. The duckbill check valve 416 and duckbill check valve insert 414 are placed in the lower part of the barrel 408. The cap 406 is welded to the barrel. The ball 426 is placed, the ball check valve insert 424 is snapped and then the quad seal 422 is inserted into the coupler 428. The stop 420 and the spring 418 are inserted into the coupler 428 and the coupler 428 is snapped on to the barrel 408. The barrel 408 is filled with reagent and the fluid dispenser 400 is primed. The cap 404 is placed on the top of the dispenser and the nozzle cap 458 is placed on the output of the nozzle 430 on the coupler 428.

Further, the present invention allows for easier manufacture and filling of the reagents in the fluid dispenser 400. Previous fluid dispensers required gluing of many pieces and sonic welding after filling the dispenser, thus requiring a certain level of skill and training. In contrast, the fluid dispenser of the present invention requires snapping in of pieces and only the sonic welding of the vent 460 to the cap 406 and the cap 406 to the barrel 408. Moreover, the filling of the reagents in the fluid dispenser 400 is easier in the present invention. In previous fluid dispensers, the fluid dispenser is assembled except for the piston, piston guide, cap and nozzle cap. The reservoir chamber is filled with reagent. The piston and piston guide are then placed in the reservoir chamber and any leftover fluid on top of the piston is evacuated. Finally, the cap is sonically welded or screwed onto the top of the barrel 408. In the present invention, since there is no piston in the reservoir chamber 410, there is no need to evacuate the area on top of the piston. Instead, the cap 406 is first sonically welded to the barrel 408, and then the reagents are added to the reservoir chamber 410. In this manner, there are fewer steps in the filling of the dispenser. Moreover, in the present invention, some of the more manufacturing sensitive parts are smaller, thereby making manufacturing easier. In the preferred embodiment, the material used is polypropylene. Under these conditions, smaller parts have a higher level of dimensional stability. Therefore, smaller components, such as the ball check valve insert 424 (which is, in the present invention, a separate component from the coupler 428) are able to be processed more consistently.

Referring to FIGS. 15A and 15B, there are shown side views of a prefilled fluid dispenser 400 and customer fillable fluid dispenser 400, respectively. Both types of dispensers have barcode labels which are read by the barcode reader 276, as described above. In order to allow the customer to fill the fluid dispenser 400 with reagent, the snap cap 404 is replaced by a flip cap 402 which varies in two ways from the snap cap: (1) the flip cap has an attachment to the cap; and (2) the flip cap has a protrusion 402A which acts as a thumbpad to prop open the flip cap 402. In previous fluid dispensers, the fluid dispenser had to be inverted in order to prime the syringe. The customer was required to first fill up a transfer syringe manually, push on an epindorf syringe and fill up this syringe. Then, the customer pressed this syringe into the coupler and forced fluid from the syringe through the connecting section between the reservoir chamber and the dispense chamber. The customer had to then pump the plunger, at least 6 to 8 times, holding the coupler upside-down, until fluid came out of the nozzle which did not have any bubbles. In the present invention, the customer opens the flip cap, fills the reservoir chamber 410, and closes the flip cap. The customer, without turning the fluid dispenser upside down, uses a typical syringe 459, as shown in FIG. 19A, to prime the fluid dispenser 400. The syringe may be manufactured by B-D Corp., in Franklin Lakes, N.J., size 20 cc, part number BC301032. The syringe 459 has a restrictor 459A and an O-ring 459B. The restrictor 459A has an internal diameter of approximately 5 thousandths of an inch. The syringe 459 is placed inside the nozzle 430 of the coupler 428 and the syringe plunger is expanded to draw fluid from the reservoir chamber 410 and the dispense chamber 412. To prime the fluid dispenser 400 more quickly, the barrel 408 is pushed down, and is released simultaneously when the syringe plunger is expanded. In this manner, there is significantly less waste of reagent. In the previous fluid dispensers, the pumping of the plunger 6-8 times wasted reagent. In the present fluid dispenser 400, any reagent is sucked into the syringe 459. Because the syringe 459 is clean, its contents may be placed back into the reservoir chamber 410 through the flip cap 402, without waste of any reagent.

Referring to FIG. 19B, there is shown an exploded view of the syringe 459 (and a syringe label 788) with a restrictor 459A and an O-ring 459B for use in the nozzle of the coupler. The O-ring 459B is placed on the side of the restrictor 459A that does not have the v-notch in it. The restrictor 459A, with the O-ring 459B side down, is placed into a holding fixture 790, as shown in FIG. 19B. The syringe 459 is then pressed onto the restrictor 459A for assembly. The restrictor 459A is made by Airlogic, in Racine, Wis., part number F-2815-050 (color: lime green), with a one inch orifice for the restrictor 459A. The O-ring 459B is manufactured by Parker Co., in Lexington, Ky., part number 2-003. The restrictor 459A fits well in the nozzle of the syringe 459 so that the syringe 459 does not need the O-ring 459B to seat against the coupler. Because of potential differences in mold runs for the coupler 428 of the fluid dispenser 400, the O-ring 459B is used so that the restrictor 459A fits tightly against the coupler 428.

To check for a good prime, the customer may flip the dispenser upside-down, tap the dispenser, dislodging any trapped air then pressing down on the barrel slowly to move the air bubble past the ball seat. The customer may then flip the coupler right-side-up and release the barrel. Good priming occurs with approximately one drop of waste.

Referring to FIG. 15C, there is shown an exploded view of a prefilled fluid dispenser with an evaporation ring 405 adjacent to the cap. The interaction of the vent, the evaporation ring 405 and the cap are discussed subsequently with respect to FIGS. 16A-E. The barcode label 784 is placed on the dispenser in order to be read by the barcode reader 276. The dispenser label 786 is also placed on the dispenser.

Figure 16A:
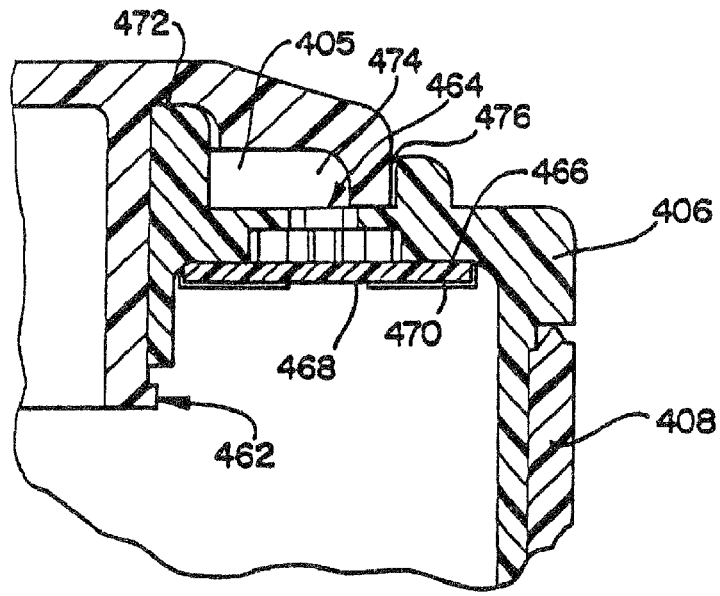
FIG. 16A is a cutaway view of the cap and vent of a prefilled fluid dispenser according to one embodiment.

Referring to FIG. 16A, there is shown a cutaway view of the cap 406 and vent 460 of a fluid dispenser 400. The vent is the component adjacent the top of the cap and includes the vent area 464, vent material 466, and backing 468. The vent 460 is used as a means to allow air to flow both into and out of the reservoir chamber 410 (i.e., so that the reservoir chamber can "breathe"). The vent 460 allows for a constant pressure in the reservoir chamber and equalizes the pressure in the reservoir chamber 410 with the pressure in the atmosphere. There are several ways in which to construct the vent in order to maintain a constant pressure in the reservoir chamber 410 and/or equalize the pressure in the reservoir chamber 410. In the preferred embodiment, as discussed more fully in subsequent figures, the vent area is approximately 70 thousandths of an inch, with a vent material 466 composed of a hydrophobic material. By experimentation, it was determined that due to size of the opening, fluid in the reservoir chamber was evaporating through the vent area. In order to reduce the evaporation (i.e., have the reservoir chamber "breathe" less), an evaporation ring 405, as shown in FIGS. 15C and 16A, was inserted in the air gap formed between the snap cap 404 and the cap 406. This evaporation ring 405 restricts the amount of air flow across the vent area, thereby reducing the amount of evaporation of fluid from the reservoir chamber.

In an alternative embodiment, the vent area is reduced to approximately 10 thousandths of an inch, thereby reducing the amount of evaporation from the reservoir chamber 410. However, processing a fluid dispenser with a reduced vent area is more difficult due to the corresponding reduced area of the vent material. In another alternative embodiment, the vent area 464 may be any area. And, the vent material may be composed of a tighter material, thereby reducing the air flow through the vent material and reducing the amount of evaporation through the vent area 464. In the preferred embodiment, the vent material is 1 µm in the size of the mesh. Reducing the size of the mesh, such as to 0.25 µm, further reduces the amount of evaporation through the vent area 464. In another alternative embodiment, the vent area may be any area and a section of tape is placed across the vent area. The tape contains a pin hole whereby the vent area is effectively reduced thereby reducing the amount of evaporation.

As shown in FIG. 16A, the cap 406 and snap cap 404 (or flip cap 402 for user fillable fluid dispensers) are luer fitting design so that the cap 406 and snap cap 404 portion which engage each other to seal the fill hole is conical. At the lower portion of the conical section of the snap cap 404 is a ring or a lip 462 that is used to snap the snap cap 404 into place. In this manner, the snap cap 404 is pushed down until it locks into the cap 406. The snap cap 404 has a curved section 472 that abuts against a curved section of the cap thereby stopping the snap cap 404 at that point. The snap cap 404 also engages the cap 406 to form an air space 474 that is adjacent to the vent area. This air space 474 forms a ring, so that regardless of the orientation of the snap cap to the cap, a hollow section is adjacent to the vent area 464 (which is approximately 70 thousandths of an inch or less). Further, the outside diameter of the snap cap 404 is slightly smaller than the inner diameter of the cap 406 so that a small air gap 476 is formed adjacent to the air space 474 to the outside of the dispenser. The air space 474 serves as a path from the vent 460 to the outside atmosphere as well as serving as a buffer between the outside of the dispenser and the vent 460. In an alternative embodiment, the air gap 476 may be used in conjunction with a notch in the side of the cap, as shown in FIG. 15C. This notch allows more air into the air gap 476, in the event that the greater air flow is required. Moreover, the notch may replace the air gap 476, so that the sole means of air flow into the air space 474 is through the notch.

The vent 460 is a hydrophobic vent which allows air to flow through the vent while keeping fluid trapped inside the reservoir chamber 410. The vent is composed of a filter material 466 such as a teflon material with a backing to attach the vent to the cap. The vent opening or area 464, as described previously, is approximately 70 thousandths of an inch. The pressure inside the reservoir chamber 410 is constant, even though the level of reagent may be changing inside the reservoir chamber 410 since air is allowed to flow into the reservoir chamber 410. Moreover, some reagents produce a by-product of gas (called outgassing). In the event that a reagent outgasses, the hydrophobic vent 460 allows gas through the vent 460, thereby avoiding any pressure build-up inside the reservoir chamber 410. In this manner, previous fluid dispensers that required a piston to exert force on the fluid in the reservoir chamber 410 may be removed. The piston in previous designs suffered from several drawbacks. First, certain reagents (such as proteins) may stick to the reservoir chamber, therefore preventing the piston from traveling with the fluid in the reservoir chamber. Additionally, the interaction between the piston and the barrel rely on lubricants. Certain reagents are composed, in part, of detergents and the detergents interfere with the lubrication between the piston and the barrel. Both effects interfere with the performance of the fluid dispenser, thereby giving inconsistent dispensing of fluid. Further, outgassing interacts with the piston either to increase the flow out of the reservoir chamber 410 or to create a compressible air gap between the piston and the main section of the reservoir chamber 410.

Also, certain types of reagents interact with the quad seal 422, causing the quad seal 422 to break down. In order to minimize this interaction, the quad seal 422 is coated with fluorine. Fluorine reacts with the outer layer of the quad seal 422, thereby discouraging reactions with certain types of reagents.

In addition, as shown in FIGS. 15C and 16A, inside the air space 474 is an evaporation ring 405. The evaporation ring 405 is composed of low density polyethylene material manufactured by Whitmark (vendor part number 105060), and is ⅛ inch thick. As discussed previously, the ring acts as a barrier, making it more difficult for air to pass across the vent. In this manner, the ring acts as a restrictor (of air), thereby reducing the amount of evaporation, while still allowing the reservoir chamber 410 to breathe. The ring is a closed cell foam, and is inexpensive in nature. The ring may be composed of any material or foam that acts to restrict the air across the vent area 464. During manufacture of the fluid dispenser, the ring is inserted in between the cap 406 and the snap cap 404. The ring should abut the vent area 464, thereby restricting the air flow across the vent area 464. Moreover, the ring, being composed of cell foam, compresses to fill up the air section 474.

Figure 16B:
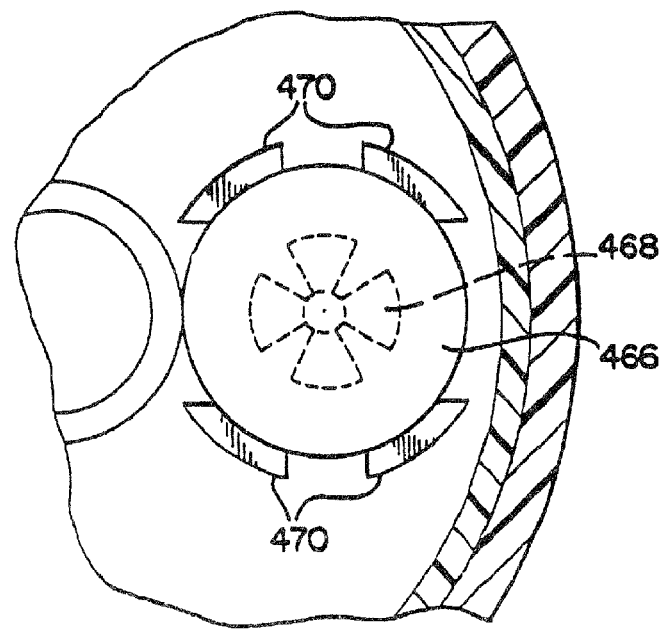
FIG. 16B is an underside view of the cap and vent of FIG. 16A.

Referring to FIG. 16A, there are protrusions 470 on the inside upper portion of the cap 406 which are used to align the piece of vent material. The vent 460 is therefore centered on top of that upper portion of the cap 406. Referring to FIG. 16B, there is shown an underside view of the vent 460. Included with the vent 460 is a platform 468 for the vent 460, star-shaped in design, which holds the vent 460 flat. When air is passing through the vent 460, particularly when outgassing, the vent 460 has a tendency to flex which may damage the teflon in the vent. In order to minimize flexing of the vent 460, the platform 468 is adjacent to the vent. Therefore, the surface area of the vent may still be relatively large but still have a grid support to stabilize the vent 460 during outgassing. The platform 466 is star-shaped due to ease of molding; however, the shape of the platform may be any design, which supports or stabilizes the vent.

Figure 16C:
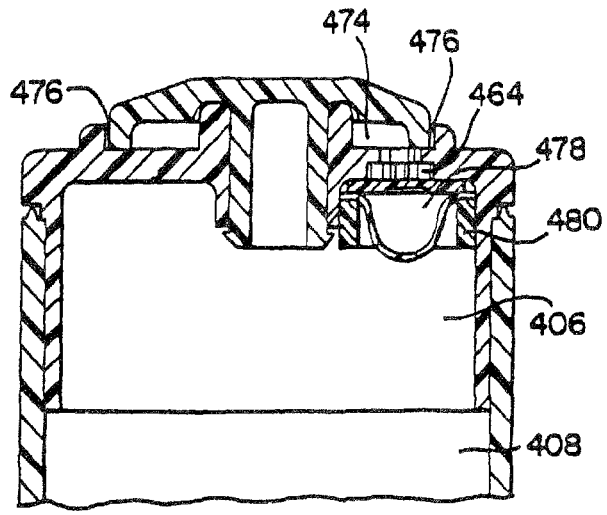
FIG. 16C is a cutaway view of the cap and vent of a prefilled fluid dispenser with a bi-directional duckbill valve.

In an alternative embodiment, as shown in FIG. 16C, the vent may be substituted with a bi-directional valve 478 or bi-directional duckbill (or two valves or two duckbills) as another means by which to allow air to flow into and out of the reservoir chamber 410. The bi-directional valve 478 has a bi-directional valve insert 480 for placement of the bi-directional valve 478. The bi-directional valve 478 also has a hydrophobic layer which allows air to flow through the bi-directional valve 478 while keeping fluid trapped inside the reservoir chamber 410. In one direction (air flowing into the reservoir chamber 410), the bi-directional duckbill 478 has a low cracking pressure, in order to equalize the pressure in the reservoir chamber 410 when fluid is dispensed. In the second direction (air flowing out of the reservoir chamber 410), the bi-directional duckbill 478 has a high cracking pressure, in order to alleviate any pressure due to outgassing. The bi-directional duckbill 478 allows air to flow through while keeping fluid trapped inside the reservoir chamber 410. Therefore, the bi-directional duckbill 478 allows air to flow into and out of the reservoir chamber 410 and allows for equalization of the pressure. In practice, a bi-directional duckbill 478 may have less refinement in terms of control when compared to two uni-directional duckbills.

Figure 16D:
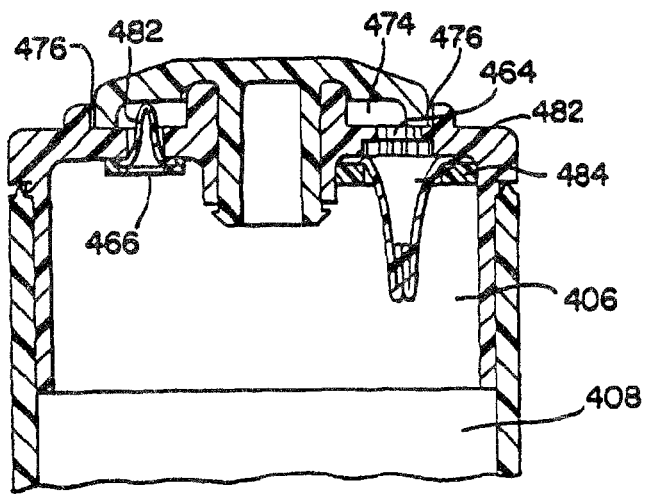
FIG. 16D is a cutaway view of the cap and vent of a prefilled fluid dispenser with a uni-directional duckbill valve.

If additional refinement is required, the bi-directional duckbill 478 may be replaced by two uni-directional duckbills, as shown in FIG. 16D. Moreover, when integrating the two uni-directional duckbills, with another uni-directional duckbill at the bottom of the barrel, the system becomes a three duckbill system. In this configuration, the duckbill that releases to atmosphere has the light cracking pressure, the duckbill that allows air into the reservoir chamber has the light cracking pressure, and the duckbill check valve 416 that is down in the barrel has a medium cracking pressure. The duckbill check valve 416 in the barrel should be of a higher cracking pressure than the duckbill releasing air to the atmosphere so that pressure built up in the reservoir should be relieved through the lighter cracking pressure duckbill.

Pressure differentials caused by outflow of fluid from the reservoir chamber 410, as discussed previously, may make the dispensing of fluid difficult. Further, in certain instances, outgassing may not interfere with the operation of the fluid dispenser 400. Therefore, the vent 460 may be substituted with a uni-directional valve or duckbill 482, (made by Vernay in Yellow Springs, Ohio, part number VL-857-101) with a duckbill valve insert 484. In the one direction (air flowing into the reservoir chamber 410), the uni-directional duckbill 482 has a low cracking pressure to alleviate pressure due to out-flow of fluid from the reservoir chamber 410. In this embodiment, vent material is not required since the air is flowing only into the reservoir chamber.

Figure 16E:
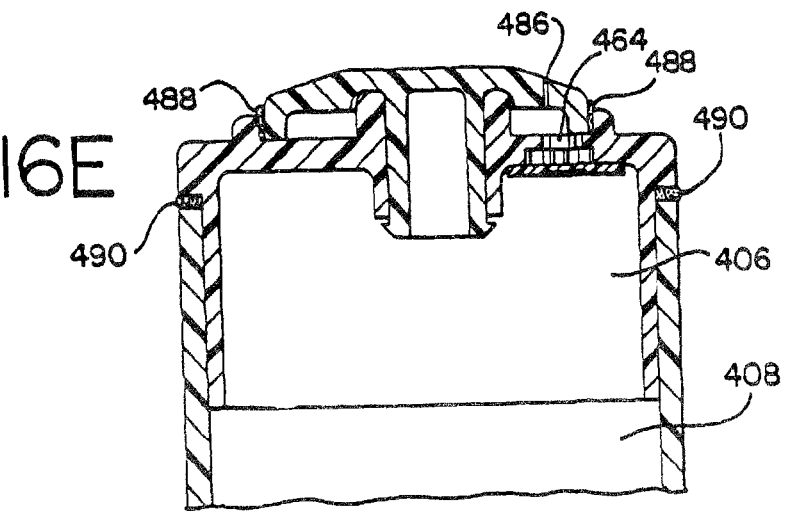
FIG. 16E is a cutaway view of the cap and vent of a prefilled fluid dispenser according to another embodiment.

In a further embodiment, as shown in FIG. 16E, the vent opening 464 may be reduced to approximately 10 thousandths of an inch (from 70 thousandths of an inch as shown in FIG. 16A). The snap cap 404, for prefilled fluid dispensers, or the flip cap 402, for user fellable fluid dispensers, may also be modified to include a seal 488 where the snap cap 404 or flip cap 402 engages the cap 406. Thus, this alternative embodiment does not have a gap 476 between the snap cap 404 (or flip cap 402) and the cap 406, but instead includes a seal 488. In order for the flow of air into or out of the reservoir chamber 410, there is an opening 486, such as a pin hole or a second vent, placed in the top of the snap cap 404 (or flip cap 402) which is adjacent to the air region 474 formed between the snap cap 404 and the cap 406.

In one embodiment, venting may be accomplished by using a mechanical valve. In one aspect, the mechanical valve comprises at least two pieces: a biasing member and a stem, the biasing member is connected or attached to the stem. In an alternate embodiment, the biasing member and stem form an integral piece. The biasing member and the stem may be comprised of the same material or the biasing member and the stem may be comprised of different materials.

In one embodiment, the mechanical valve operates such that in one position, a hole in the fluid dispenser is sealed, and in another position, the valve does not seal the hole. In one embodiment, in operation, the biasing member of the valve without external mechanical force biases the stem such that at least a portion of the stem seals the hole in the fluid dispenser. By applying a mechanical force to at least a portion of the biasing member, the stem, which is connected to or integral with the biasing member, moves, thereby unsealing the hole in the fluid dispenser. Subsequently, the biasing member, without external force, biases the stem again such that the stem does not seal the hole. Applying mechanical force to at least a portion of the biasing member moves the stem so that at least a portion of the stem seals the hole in the fluid dispenser. In an alternate embodiment, the biasing member without external mechanical force seals the hole in the fluid dispenser so that by applying a mechanical force, at least a portion of the hole is unsealed.

Using an elastomeric mechanical valve (and in one embodiment, an umbrella valve), the reservoir of the fluid dispenser may be sealed. However, in the embodiment where an umbrella valve is used, the umbrella valve is not used in the normal manner as known to those skilled in the art. Umbrella valves are normally used as pressure actuated check valves that seal against flow in one direction and are opened by pressure in the other direction. In the normal manner of umbrella valve usage, the outer flange of the umbrella is urged against a flat sealing surface by the spring force of the deflected umbrella. Fluid pressure on top of the umbrella valve only tends to further seal the flange to its mating seat. The valve is opened by pressure under the umbrella pushing it away from its mating surface, allowing fluid to pass between the flange and its mating sealing surface.

One aspect of the invention makes a mechanical valve out of an umbrella valve, instead of a pressure actuated valve, by using the bulge on the stem, urged against a sharp corner at the end of a hole through which the stem passes as a sealing point. The flange is prevented from sealing by adding slots to its mating surface. The flanged head is used as a disk spring to urge the bulge to seal against it seat, which is opened when the center of the umbrella is deflected downward by the dispenser actuator. The movement of the center of the umbrella downward, or at least a portion of the umbrella downward, pushes the stem and its associated bulge down, uncovering the sealing area, thereby opening the valve and venting the reservoir. An oliophobic vent may be added in series to provide additional safety in preventing liquid from leaking out even if the mechanical vent fails.

Thus, this provides a method and apparatus to modify the pressure in a fluid dispenser. This further provides a method and apparatus that prevents a vacuum from forming in the reservoir chamber of a fluid dispenser while the liquid contained in the dispenser may be pumped out, and at the same time preventing a pressure buildup in the reservoir due to outgassing during the pumping cycle. Moreover, the method and apparatus can prevent liquid from leaving the reservoir through an insert vent that may be placed underneath the mechanical valve of the fluid dispenser. In addition, the method and apparatus can prevent the vapor of an evaporated reagent from leaving the reservoir chamber. Finally, this may eliminate the need for a circuitous path or the use of foam between the vent and the surroundings as has been used in the past.

Figure 16F:
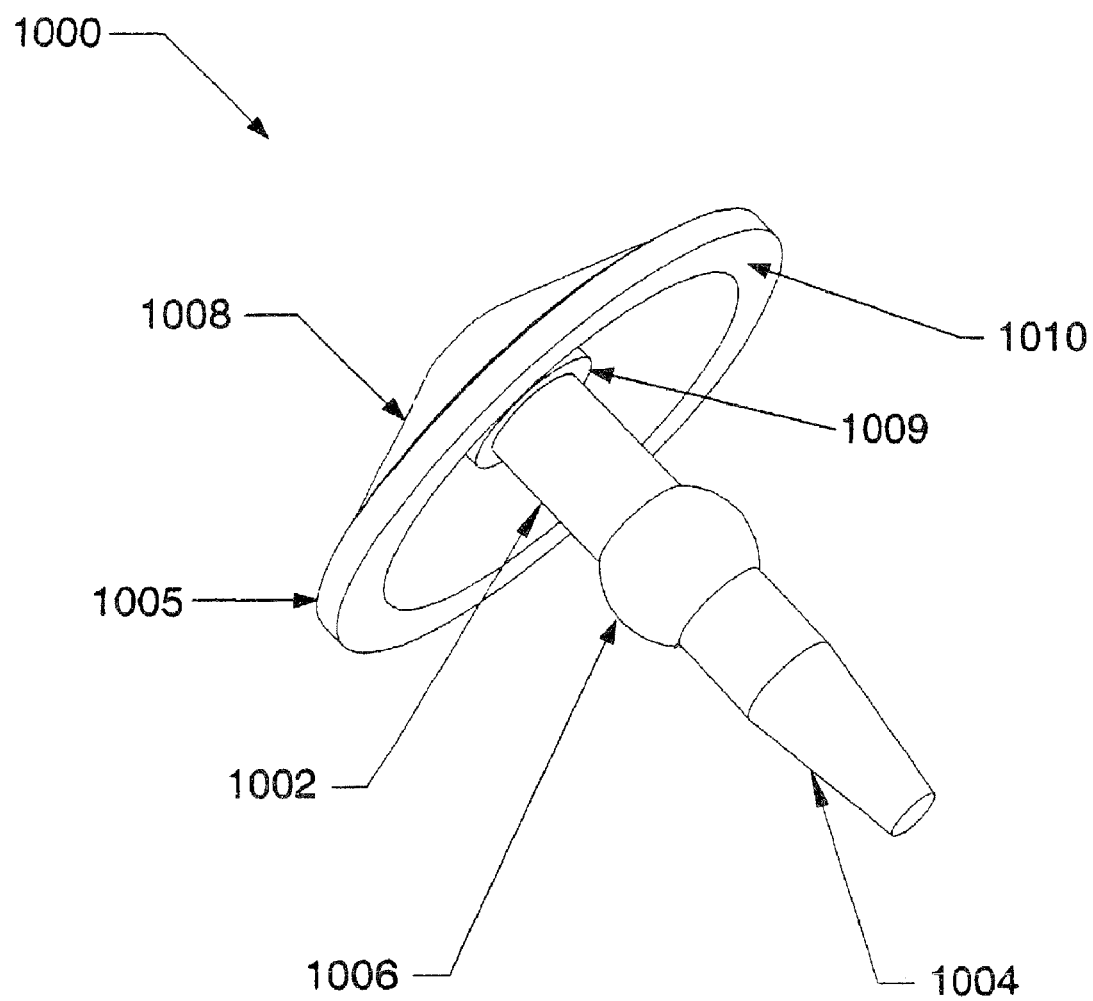
FIG. 16F is a perspective view of a valve arranged to operate in accordance with an exemplary embodiment of the present invention.

Referring to FIG. 16F, an assembly of a valve 1000 is shown arranged to operate in accordance with one embodiment of the present invention. The valve may take a variety of forms such as an umbrella shape, as shown in FIG. 16F, or any other shape consistent with the operations of the mechanical valve. Examples of other forms consistent with the operations of the mechanical valve include, but are not limited to: a spring mechanism, or an elastomeric mechanism. The valve 1000 may have a stem with two portions, either being an integral piece or a series of pieces. The upper portion 1002 of the stem may connect to the head 1008 of the valve 1000. The head 1008 may be a flanged head as shown in FIG. 16F. Other forms may include a flat surface, or a non-circular head.

The upper portion 1002 of the stem may be connected to the lower portion 1004 of the stem by a bulge 1006. The lower portion 1004 of the stem may extend below the bulge 1006. The upper portion 1002 of the stem and the lower portion 1004 of the stem may not be the same size, shape, or length. In a preferred embodiment, at least a section of the upper portion 1002 and lower portion 1004 of the stem of the valve 1000 may be cylindrical in shape. The valve 1000 may be entirely made of an elastomeric material with each component interconnected. In another embodiment, at least one of the bulge 1006 or the head 1008 are comprised of an elastomeric material.

In one embodiment, the head 1008 of the valve 1000 may act as a spring force. The head 1008 may be capable of being deflected and re-formed for a purpose of applying a force to the stem portion of the valve 1000. The head 1008 may be comprised of a curved surface. In another embodiment, the head 1008 may have an umbrella shape. The underside of the head 1008 may be comprised of an open space to allow for the deflection of the head 1008. An annular portion 1009 may exist on the underside of head 1008 at the upper end of stem 1002 that acts as a stop for motion of head 1008. The head 1008 may be deflected by pressing down on the top of the head 1008. In a preferred embodiment, the head 1008 may be deflected by pressing down on a center portion of the head 1008. Furthermore, the head 1008 may be deflected by pressing down on the uppermost portion of the head, although those skilled in the art will recognize that the head 1008 may be depressed by applying a force onto any portion of the head 1008. An outer perimeter portion 1010 of the underside of the head 1008 may be substantially flat in order to contact a surface.

The bulge 1006 of the valve 1000 may be of a spherical shape. Other forms may include an oblong shape or an elliptical shape. In one embodiment, the bulge 1006, the upper portion 1002 of the stem, and the lower portion 1004 of the stem may be one integral piece. In another embodiment, the bulge 1006 may be a separate piece of the valve 1000 connected to the upper portion 1002 and the lower portion 1004 of the stem. In one embodiment, the bulge 1006 may have a larger diameter than the upper portion 1002 of the stem. In another embodiment, the bulge 1006 may have a larger diameter than the lower portion 1004 of the stem. At least a section of the lower portion 1004 of the stem may have a diameter that decreases in distance from the bulge 1006. This may allow for the valve 1000 to be easily placed into holes or small areas since at least a section of the lower portion 1004 of the stem may have a conical shape.

Figure 16G:
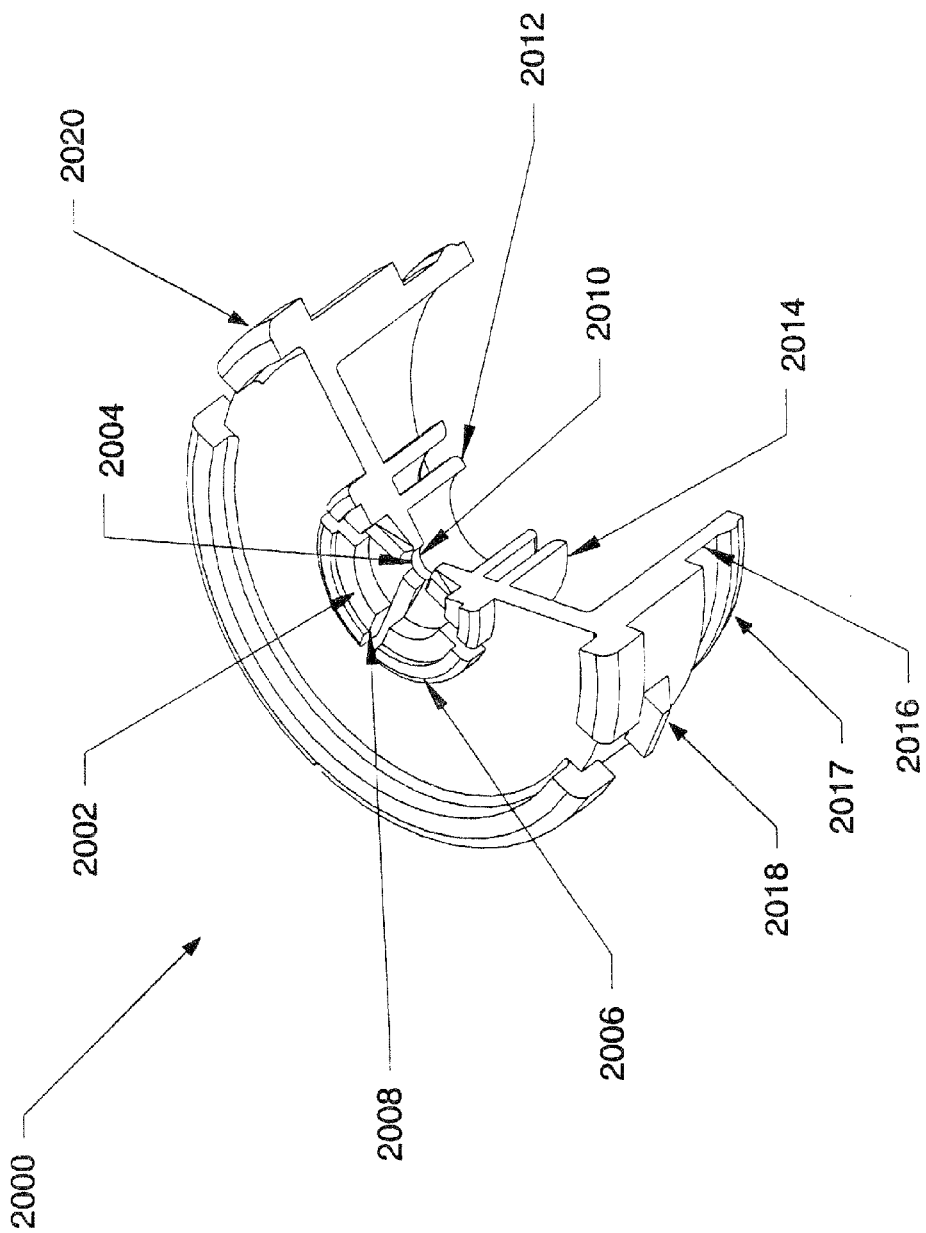
FIG. 16G is a perspective view of a cap of a fluid dispenser arranged to operate in accordance with an exemplary embodiment of the present invention.

Referring to FIG. 16G, a cap 2000 of a fluid dispenser is shown arranged to operate in accordance with one embodiment of the present invention. The cap 2000 may be mounted on top or on the side of a fluid dispenser. The cap 2000 may have a sealing surface 2016 which may seal the cap 2000 with the fluid dispenser. The cap may be comprised of a plastic material, or another rigid material. The sealing surface 2016 may have a ridge 2017 which may fit tightly into the fluid dispenser. A hole 2004 may be present in the cap 2000. The hole 2004 may be placed at any position on the cap 2000. In the preferred embodiment, the hole 2004 is placed in the center of the cap 2000. The bottom corner 2010 of the hole 2004 should preferably have a small radius (e.g., 0.002 inch), so that the bottom corner 2010 is sharp.

The cap 2000 may have a surface 2002 that mates with the head 1008 of the valve 1000. The surface 2002 may be raised from the hole 2004 by a small amount in order to provide an area for the head 1008 of the mechanical valve 1000 to be deflected into, as discussed above. The surface 2002 may have cuts, such as cut 2008, breaks, or passageways for air through the surface 2002 so that gas and/or vapor may always pass underneath the head 1008 of the valve 1000. The cuts may act as breaks or trenches for air. Moreover, the cuts may be of any shape and any size large enough to allow air to pass through. The cuts may be positioned in order to always allow air to pass through, even when valve 1000 is inserted into the cap 2000. Air may only pass through the hole 2004, and subsequently through the breaks or cut 2008, when the valve 1000 is depressed or open.

A small protective ridge 2006 may surround the surface 2002 and the head 1008 of the valve 1000. The protective ridge 2006 may be raised from the surface 2002 of the cap 2000. The protective ridge 2006 may provide an outer perimeter for the head 1008 of the valve 1000 to be placed. The protective ridge 2006 may be raised an amount equal to the thickness of an outer edge 1005 of the valve in order to provide a secure housing for placement of the valve 1000. The cut 2008 may pass through the protective ridge 2006 in order to allow for a passageway for air.

An inner circular wall 2012 and an outer circular wall 2014 may mate to an insert vent 4000, as will be described later. The inner circular wall 2012 and the outer circular wall 2014 may extend below the hole 2004 of the cap 2000. The inner circular wall 2012 and the outer circular wall 2014 may be thin and may be separated by a distance substantially equal to the thickness of the insert vent 4000 housing. The outer circular wall 2012 may extend directly below the protective ridge 2006 of the cap 2000. The inner circular wall 2012 and the outer circular wall 2014 may have a length substantially equal to the length of the stem of the mechanical valve 1000. The outer circular wall 2014 and the inner circular wall 2012 may be comprised of the same material as the cap 2000 of the fluid dispenser. Alternatively, the outer circular wall 2014 and the inner circular wall 2012 may be comprised of a different material than the cap 2000.

In one embodiment, the cap 2000 may contain a fastener member 2018 on each side of the cap 2000. In a preferred embodiment, two fastener members 2018 are placed on the cap 2000, but those skilled in the art will recognize that any desired number of fastener members 2018 may be present. The fastener member(s) 2018 may be placed directly across from one another. The fastener member(s) 2018 may hold the cap 2000 in place on the fluid dispenser. The fastener member(s) 2018 may be shaped to allow the cap 2000 to slide into the fluid dispenser and click into place, but not slide out. The fastener member(s) 2018 may have a smooth surface which allows the cap 2000 to slide into the fluid dispenser. The fastener member(s) 2018 may lock onto a ridge of the fluid dispenser upon placement of the cap 2000 into the fluid dispenser.

Figure 16H:
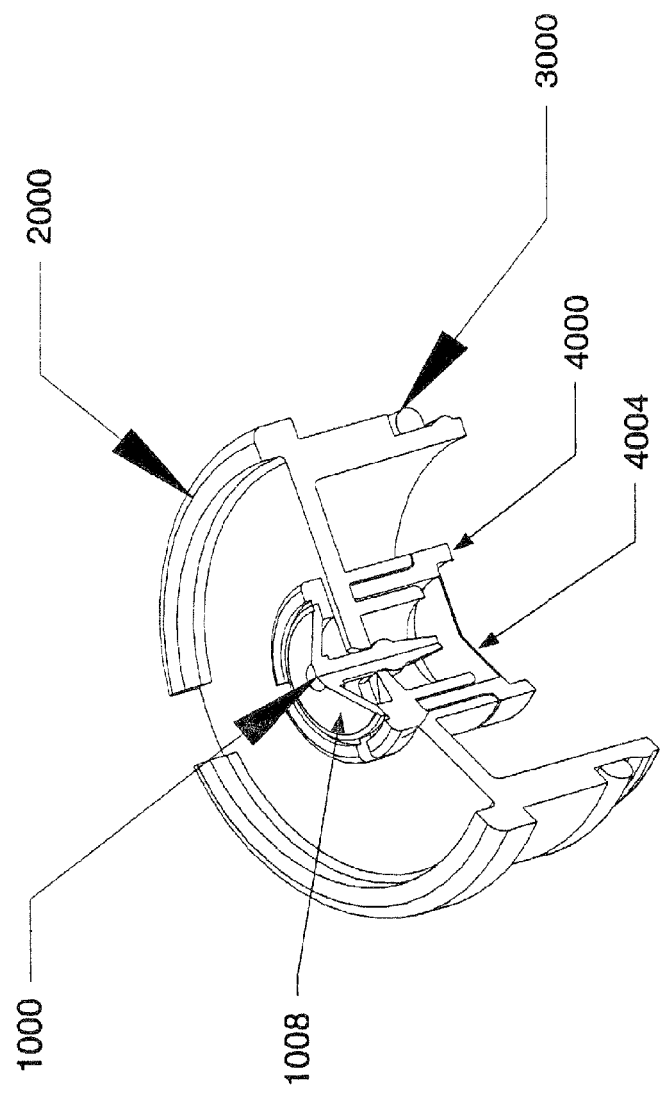
FIG. 16H is a perspective view of a valve of FIG. 16F inserted into the cap of FIG. 16G.

Referring to FIG. 16H, a cap 2000 with the valve 1000 installed is illustrated arranged to operate in accordance with one embodiment of the present invention. The bulge 1006 on the stem of the valve 1000 may mate with the bottom corner 2010 of the hole 2004. The bulge 1006 may be urged against the bottom corner 2010 of the hole 2004 to form a seal to the hole 2004 by the spring tension of the head 1008 of the valve 1000. The force from the head 1008 of the valve 1000 may be transmitted to the bulge 1006 by the upper portion 1002 of the stem. The upper portion 1002 of the stem may pass through the hole 2004 in the cap 2000. The hole 2004 may be slightly larger than the diameter of the stem, so that vapor or gas may pass through the hole 2004 if the bulge 1006 is not sealed against the hole 2004. The bulge 1006 may be slightly larger than the hole 2004, so that the bulge 1006 may seal to the bottom corner 2010 of the hole 2004.

In one embodiment, upon urging the bulge 1006 against the bottom corner 2010 of the hole 2004, the bulge 1006 may form a seal that prevents gas, vapor and/or liquid from exiting a reservoir chamber of the fluid dispenser. The bulge 1006 may be biased by a biasing member, such as head 1008, used to seal the hole 2004 of the cap 2000. The bulge 1006 may become compressed upon urging the bulge 1006 against the bottom corner 2010 of the hole 2004. This may occur because the bulge 1006 may be comprised of an elastomeric material. If the pressure in the reservoir increases so that the pressure is higher than the surrounding atmosphere, the pressure may cause the bulge 1006 to seal more tightly than before. As shown in FIG. 16H, an o-ring 3000 may be provided to aid in the sealing of the cap 2000 to the fluid dispenser. The o-ring 3000 may be comprised of an elastomeric material in order to allow for the cap 2000 to tightly fit into the fluid dispenser. The o-ring may 3000 may become compressed upon inserting the cap 2000 into a fluid dispenser.

As shown in FIG. 16H, an insert vent 4000 may be placed underneath the valve 1000. The housing of insert vent 4000 may fit between the inner circular wall 2012 and the outer circular wall 2014. Specifically, the housing of the insert vent 4000 may slide between the inner circular wall 2012 and the outer circular wall 2014 and fit tightly to disallow air, vapor, or liquid to pass through the vent. The insert vent 4000 may be any shape, preferably of a circular shape to conform to the shape of the cap 2000 for the fluid dispenser. The insert vent 4000 may be placed underneath the valve 1000 at a distance great enough to allow for an open space between the insert vent 4000 and the valve 1000. The insert vent 4000 may also contain an oliophobic vent 4004 in the center of the insert vent 4000 as an added safety feature.

Figure 16I:
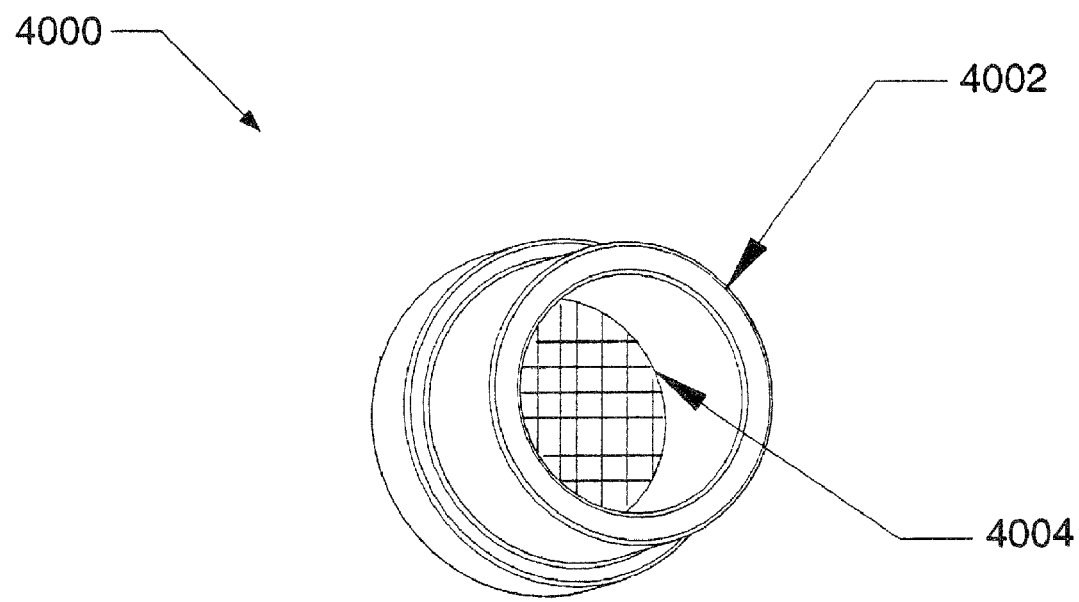
FIG. 16I is a perspective view of a vent as shown in FIG. 16H arranged to operate in accordance with an exemplary embodiment of the present invention.

Referring to FIG. 16I, an insert vent 4000 is shown in accordance with an embodiment of the present invention. An exemplary insert vent found suitable for use in the cap 2000 of the fluid dispenser is one made and sold by W.L. Gore & Associates, and having model number D10, although those skilled in the art will recognize that any insert vent with similar characteristics would also be suitable. The insert vent 4000 may have an oliophobic vent 4004 attached to one end. The oliophobic vent 4004 does not allow liquid to pass through. The oliophobic vent 4004 may connect to a plastic cylinder 4002. The oliophobic vent 4004 may be placed on one end of the housing of the insert vent 4000. The insert vent 4000 may mate to an inner circular wall 2012 and an outer circular wall 2014 of the cap 2000 as shown in FIG. 16H. The inner circular wall 2012 and the outer circular wall 2014 may allow the insert vent 4000 to fit tightly into the cap 2000. The insert vent 4000 may act as an added safety feature for the venting of the fluid dispenser, or as an added liquid barrier for the cap 2000 of the fluid dispenser. The insert vent 4000 may allow air to pass through in order to modify the pressure in the reservoir chamber of the fluid dispenser, but the insert vent 4000 may not allow liquid to pass through thereby creating a liquid barrier.

Figure 16J:
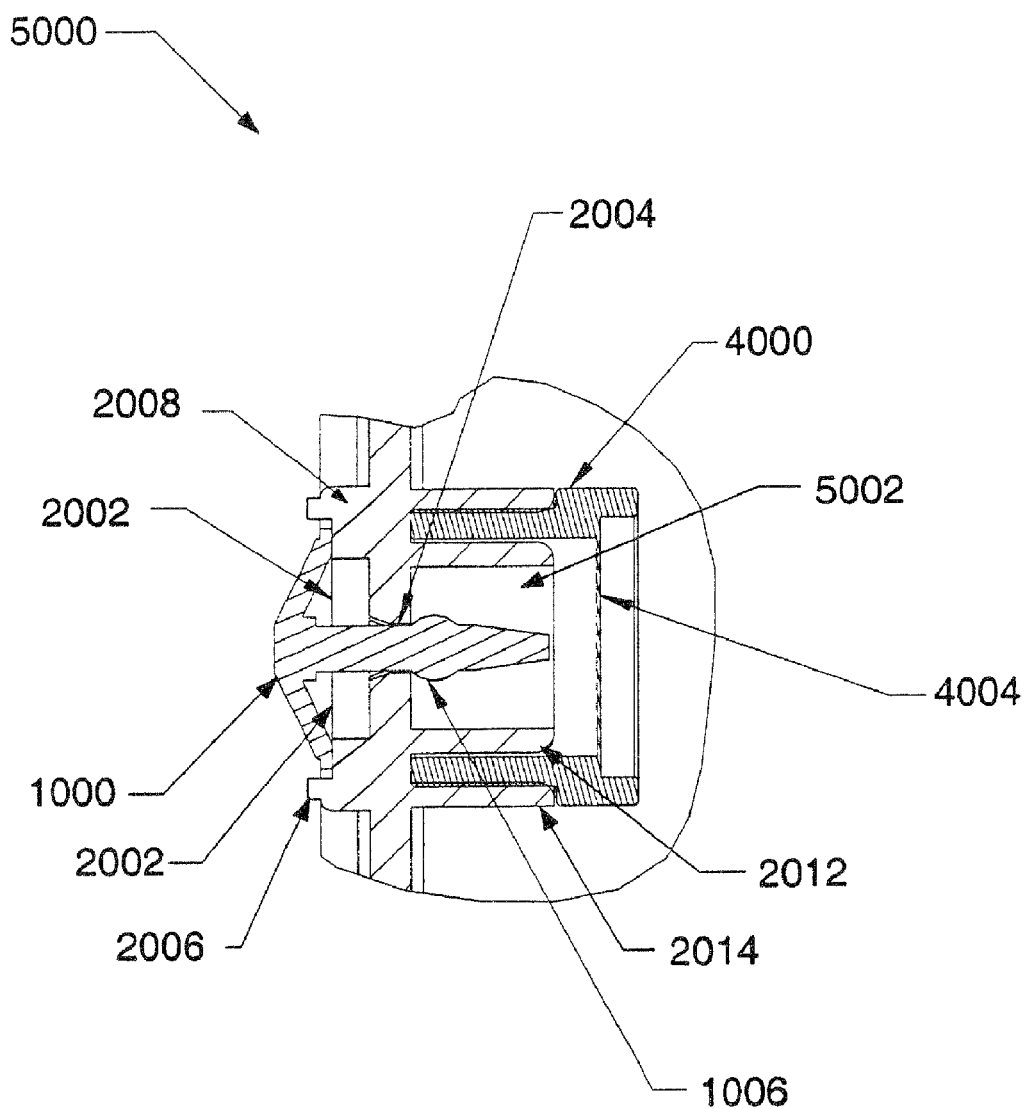
FIG. 16J is a side view of the cap of FIG. 16H inserted into a fluid dispenser arranged to operate in accordance with an exemplary embodiment of the present invention.

Referring to FIG. 16J, a side view of the valve 1000 inserted into the cap 2000 is illustrated arranged to operate in accordance with one embodiment of the present invention. The top 5000 of the fluid dispenser is positioned horizontally with reference to the fluid dispenser. In an alternate embodiment, the cap 2000 may be positioned vertical with reference to the fluid dispenser. One cut 2008 underneath the valve 1000 is shown at surface 2002 with protective ridge 2006. In a preferred embodiment, four cut are provided for passageways for air to vent the reservoir of the fluid dispenser. The cut may be equally spaced around the surface 2002. The insert vent 4000 is shown inserted between the inner circular wall 2012 and the outer circular wall 2014 of the cap 2000. The oliophobic vent 4004 is shown placed at one end of the insert vent 4000. The oliophobic vent 4004 may be a thin membrane inserted between the outer and inner housing of the insert vent 4000.

As shown in FIG. 16J, the valve 1000 may fit into the cap 2000 in order to provide for a match with the surface 2002 of the cap 2000. A space 5002 inside the inner circular wall 2012 of the cap 2000 may be open to allow for air to pass through as shown. The insert vent 4000 may be placed underneath the valve 1000 at a distance so as not to touch the valve 1000. A space or a small distance may be present between the oliophobic vent 4004 of the insert vent 4000 and the valve 1000 to allow for the valve 1000 to be pressed downward. The small distance available between the oliophobic vent 4004 and the lower portion of the stem 1004 is substantially the amount of distance that the bulge 1006 may be displaced in order to allow air to pass underneath the mechanical valve 1000.

Figure 16K:
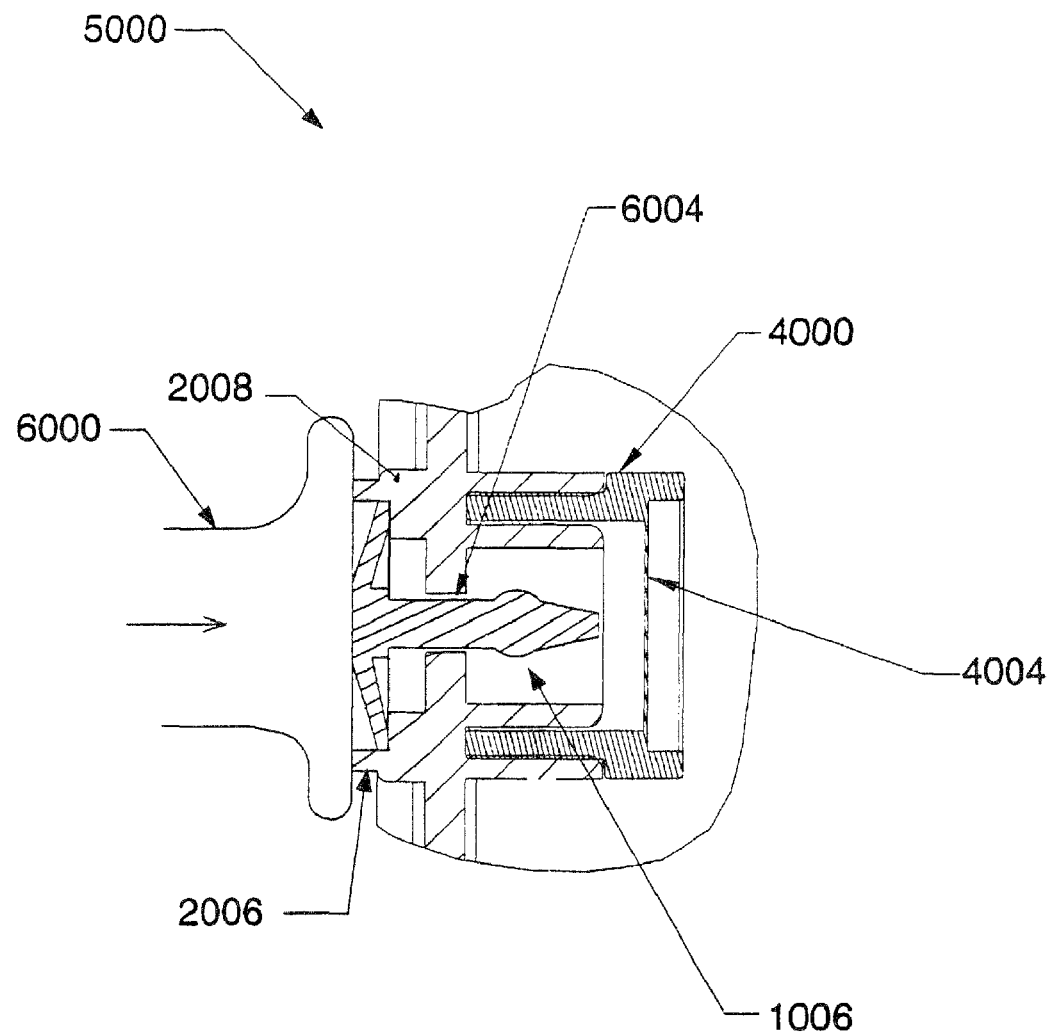
FIG. 16K is a side view of one method of operating the valve of FIG. 16F arranged to operate in accordance with an exemplary embodiment of the present invention.

The fluid in a fluid dispenser may be dispensed by movement of the barrel. An example of a barrel is shown in FIG. 12A. Referring to FIG. 16K, the fluid dispenser may be placed into a machine with a plunger 6000, or other means of applying force, to press down upon the barrel of the fluid dispenser. When pushing on the barrel, the plunger 6000 may contact the cap 2000 of the fluid dispenser. Thus, the plunger 6000 of the machine may mechanically open the valve 1000 as shown in FIG. 16K. When the plunger 6000 on the machine contacts the fluid dispenser, the plunger 6000 may first contact the top of the head 1008 of the valve 1000 which is inserted into the cap 2000. Any portion of the head 1008 may be contacted. In one embodiment, the plunger 6000 contacts the center of the head 1008 of the valve 1000 exerting a mechanical force on the head 1008. This mechanical force in the direction perpendicular to the head 1008 depresses the head 1008 downward. When the head 1008 of the valve 1000 is pressed down, this displaces the stem and its associated bulge 1006 as shown in FIG. 16K. The top of head 1008 is displaced downward until flush with protective ridge 2006 where plunger 6000 then contacts protective ridge 2006.

In one embodiment, the head 1008 of the valve 1000 may be deflected downward because the head 1008 is made of an elastomeric material. The head 1008 may be deflected downward until the plunger 6000 contacts protective ridge 2006. The contact of the annular portion 1009 of the head 1008 with the surface 2002 does not prevent air from passing underneath the valve 1000. Since the head 1008 of the valve 1000 may be positioned on top of the surface 2002 of the cap 2000, air may be able to pass underneath the valve 1000 through the cuts. The cuts on the surface 2002 allow for passageways for air to pass underneath the valve 1000. The valve 1000 contacts the surface 2002 upon mechanically opening the valve 1000, but the cut are made in the surface 2002, and thus allow for air to pass underneath the valve 1000.

Upon deflection of the head 1008, the head 1008 exerts a force onto the stem portion of the valve 1000. The upper portion 1002 of the valve 1000 may transmit the force from the head 1008 onto the bulge 1006 which displaces the bulge 1006 from the hole 2004. Once the bulge 1006 is displaced from the hole 2004, the valve 1000 will be open as shown in FIG. 16K. Since the hole 2004 is of a smaller diameter than the stem of the valve 1000, a space may be present between the upper portion 1002 of the stem and the outer area of the hole 2004. This may allow for the pressure in the reservoir to equilibrate with that of the surrounding atmosphere by allowing air to pass through the space 6004 between the upper portion 1002 of the stem and the outer area of the hole 2004, and subsequently pass through the cut.

The cut on the surface 2002 of the cap 2000 allow for a passageway of free communication of air between the outer atmosphere and the inside of the reservoir chamber when the bulge 1006 is displaced from the hole 2004. Air may pass through the cut underneath the valve 1000 because of a pressure differential between the inside of the reservoir chamber and the outside of the reservoir chamber. The air will move from a region of higher concentration of pressure to a region of a lower concentration of pressure. In one embodiment, the pressure inside the fluid dispenser may be higher than the pressure on the outside of the fluid dispenser. In another embodiment, the pressure inside the fluid dispenser may be lower than the pressure on the outside of the fluid dispenser. Air may pass out of the fluid dispenser until the pressure inside the fluid dispenser is equal to the pressure outside the fluid dispenser.

The seal of the bulge 1006 against the hole 2004 may be re-formed to disallow air to pass underneath the valve 1000 upon removing the plunger 6000 from the top of the head 1008 of the valve 1000. Once the plunger 6000 is removed by the machine, the head 1008 may not be deflected, and the head 1008 may slowly re-form due to the stored potential spring energy of the head 1008 of the valve 1000 and pull the upper portion 1002 and the lower portion 1004 of the stem of the valve 1000 upward a small distance. When the stem is moved upward, the bulge 1006 may move upward as well. The bulge 1006 may then become pressed against the hole 2004 of the cap 2000 and form a tight seal. A portion of the stem may become compressed upon moving the stem upward. Moreover, the bulge 1006 may become compressed as well upon pressing the bulge 1006 against the hole 2004 to form a tight seal.

Using the elastomeric valve 1000 may seal the reservoir of the fluid dispenser. In one embodiment, a requirement of a valve is for the valve to have a dual-purpose vent. The first purpose is to allow air to pass into the reservoir to prevent a vacuum from forming as liquid is removed. The second purpose of the vent is to allow any internal pressure that might build up inside the reservoir to equilibrate with ambient pressure before the first dispense. Internal pressure is not in itself a substantial problem. However, internal pressure may not be tolerated when the dispenser is actuated, as the pressure would expel too large of a volume of liquid. The valve 1000 provides a manner of sufficiently venting the fluid dispenser.

Referring to FIG. 17A, there is shown a cutaway view of the lower portion of the barrel 408, duckbill check valve 416, duckbill check valve insert 414, quad seal 422, ball 426, ball check valve insert 424 and coupler 428 of a fluid dispenser 400. The barrel 408 has protrusions 408A, which mate with the coupler in order to, maintain the position of the barrel 408 on the upstroke. Otherwise, if the spring pushes the barrel 408 upward too high, the seal, as provided by the quad seal 422, may be broken thereby creating an air path and causing the fluid dispenser 400 to lose prime. The barrel 408 also has a flange 408B which mates with the stop 420 on the downstroke. The barrel 408 also has a pocket 408C, where the duckbill check valve insert 414 is inserted. This pocket acts as a funnel so that no puddles are formed at the bottom of the barrel 408 at the interaction point with the duckbill check valve 416 or duckbill check valve insert 414, thereby minimizing waste. The barrel 408 also has at its lower portion a piston 454 by which fluid is expelled in the dispenser 400. At the lower portion of FIG. 17A is a nozzle cap 458 for engagement with the nozzle 430 of the coupler 428. The nozzle cap 454 and nozzle 430 are matched using a luer fitting design in order to be a fluid tight seal. Referring to FIG. 17B, there is shown a cutaway view of the lower portion of the barrel, duckbill check valve, and duckbill check valve insert of a fluid dispenser. Referring to FIG. 17C, there is shown a cutaway view of the quad seal of a fluid dispenser.

FIG. 17A also shows a cutaway view of the coupler 428. The coupler 428 has grooves 428B in which the ball check valve insert 424 snaps. The grooves 428B act to prevent any leakage of fluid downward or air upward through the walls of the ball check valve insert 424 and the coupler wall. The coupler 428 also has protrusions 428C, which ensure that the dispenser is aligned on the reagent tray 10. For example, if the dispenser is misaligned, the dispense cylinder may not engage the dispenser properly. The coupler also has stabilizing bumps 428D, which reduce any rocking back and forth of the fluid dispenser 400.

Further, in an alternative embodiment as shown in FIG. 18A, there is shown a barrel 408 which has a lower section which acts as a piston 454 at its lower end, similar to FIGS. 12A-12C. Instead of a throughhole at the bottom of the piston 454 at the lower section of the barrel in the piston area, there are holes 450 in the side of the piston 454 that contact O-ring seals 452. In this manner, when the barrel 408 is pushed downward, the holes 450 are exposed, dispensing fluid from the reservoir chamber 410. When the barrel is returning to the up position, the pressure differential is such that the duckbill check valve 482 opens and fills the dispense chamber 410 with fluid. Because of the lack of a high pressure differential on the upstroke of the barrel, the duckbill check valve 482 in FIG. 18A is a duckbill check valve of low cracking pressure. Further, when the barrel is in the up position, the end of the piston 454A is closed by the O-ring seals 452 thereby sealing the bottom of the barrel 408 except for the holes 450.

Referring to another alternative embodiment as shown in FIG. 18B, there is shown a barrel 408 which has a lower section which acts as a piston 454 at its lower end, similar to FIG. 18A. Instead of placing O-ring seals 452 to cover the hole 450 in the lower end of the piston 454A, a quad seal 422, similar to the quad seal used in FIGS. 14A and 14B, is used.

Figure 20:
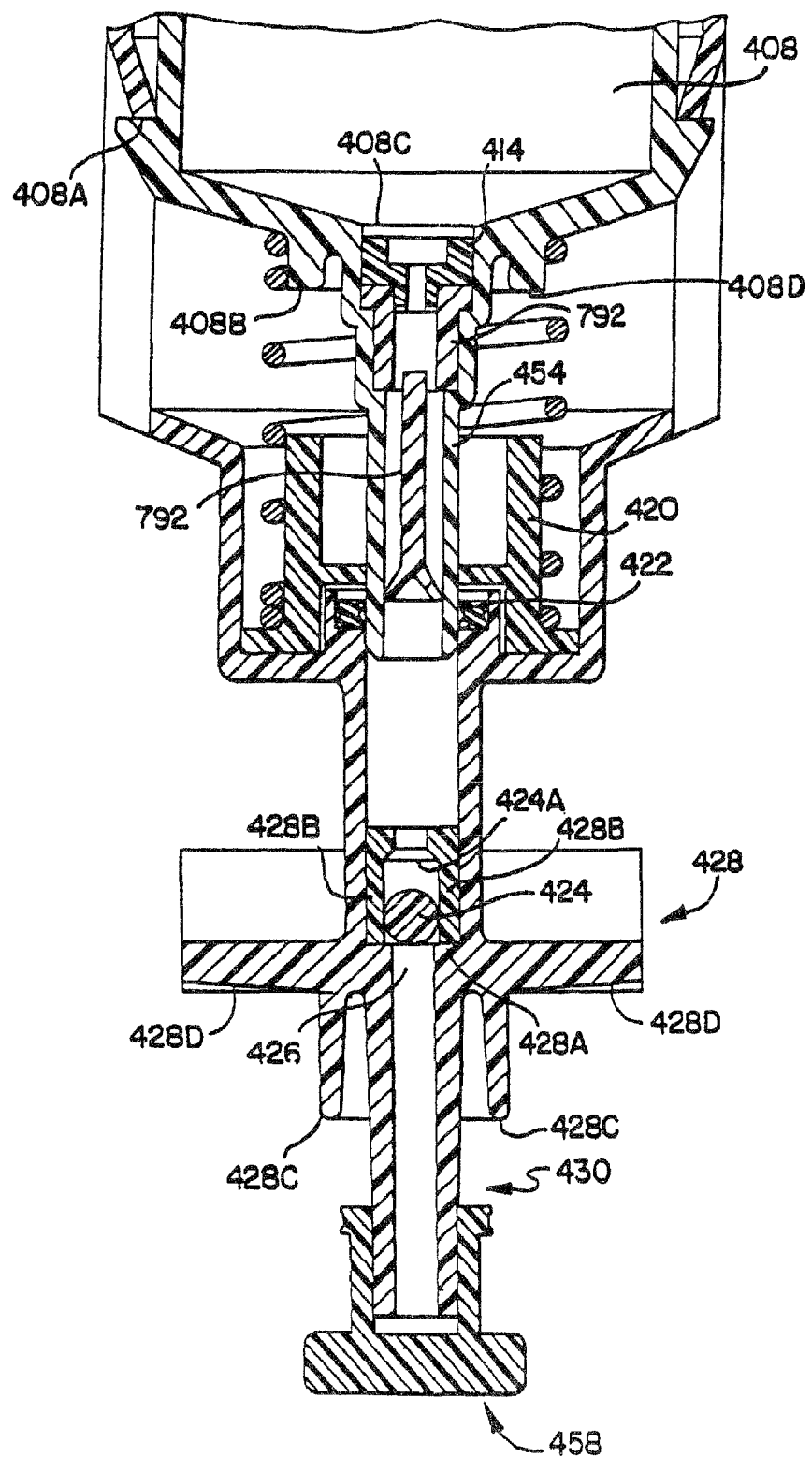
FIG. 20 is an alternative embodiment of a cutaway view of the lower portion of the fluid dispenser with a cup check valve.

Referring to FIG. 20, there is shown an alternative embodiment of a cutaway view of the lower portion of the fluid dispenser with a cup check valve 792. The lower portion of the cup check valve 792 (i.e., the cup piece 794) abuts against the piston 454 of the barrel 408, thereby disallowing liquid to pass through the lower portion of the barrel 408. The upper portion of the cup check valve 792, which is composed of an upper ledge 800 and side walls 802, abuts against the duckbill check valve insert 414 and the side of the piston 454. The cup check valve 792 operates in a manner similar to the duckbill check valve 416, as shown in FIG. 17A in that it operates based on a pressure differential. During the downstroke of the barrel 408, the cup piece 794 of the cup check valve 792 remains rigid so that the piston, and the cup piece, push the liquid out of the dispense chamber 412. During the upstroke of the barrel 408, the ball 434 in the ball chamber 432 seats against the check valve ball insert 424, as described in FIG. 13A, creating a vacuum in the dispense chamber. This vacuum creates a pressure in the dispense chamber and in the adjacent piston area of the barrel 408, causing the cup piece 794 of the cup check valve 792 to flex inward, so that the cup piece 794 does not abut against the piston 454. When this occurs, fluid in the reservoir chamber is allowed to pass around the cup check valve 792 and into the dispense chamber. The cup piece 794 is flexed inward until the pressure equalizes between the dispense chamber and reservoir chamber. As such, the dispense chamber receives fluid on the upstroke of the barrel 408. For better flexing effect due to the vacuum caused in the dispense chamber, the cup piece 794 of the cup check valve 792 should sit low in the piston 454 of the barrel 408. In this manner, the less area under the cup, the more suction effect caused by the vacuum.

Figure 21A:
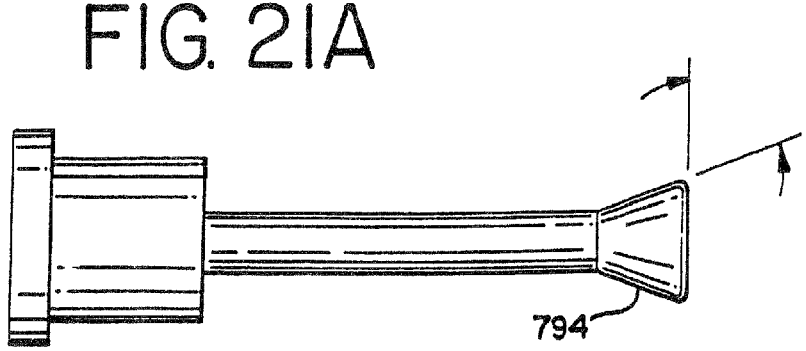
FIG. 21A is a side view of the cup check valve.

Referring to FIG. 21A, there is shown a side view of the cup check valve 792. The cup piece 794 spreads outward at angle of approximately 71° from the horizontal. However, the cup piece 794 may be curved outward or inward, depending on the flexing needs of the cup piece 794. Moreover, the upper ledge 800 and side walls 802 are formed to abut against the duckbill check valve insert 414 and the side of the piston 454. This upper piece may be of such a form in order to be held securely in place.

Figure 21B:
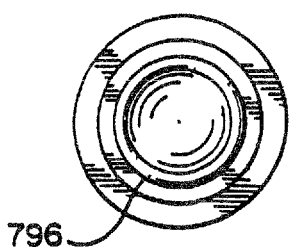
FIG. 21B is a bottom view of the cup check valve.

Referring to FIG. 21B, there is shown a bottom view of the cup check valve 792. The bottom 796 is round, in order to abut the round sidewalls of the piston 454. The bottom of the cup check valve 792 may be any shape that forms against the surface abutting it, in this case, the piston 454.

Figure 21C:
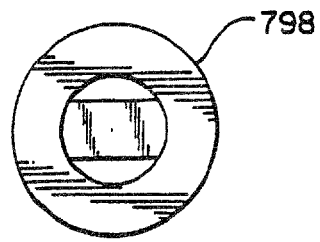
FIG. 21C is a top view of the cup check valve.

Referring to FIG. 21C, there is shown a top view of the cup check valve 792. The top 798 is round, in order to abut the round sidewalls of the duckbill check valve insert 414. The top of the cup check valve 792 may be any shape that forms against the surface abutting it, in this case, the duckbill check valve insert 414.

Figure 21D:
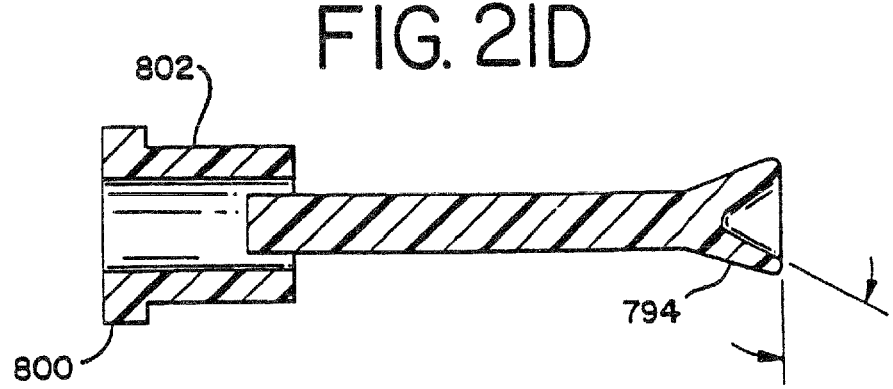
FIG. 21D is a view of the cup check valve at cross-section A-A in FIG. 21C.
Figure 21E:
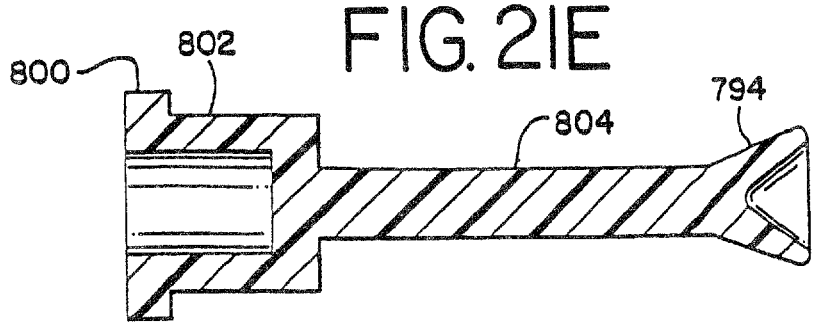
FIG. 21E is a view of the cup check valve at cross-section B-B in FIG. 21C.

Referring to FIGS. 21D and 21E, there are shown views of the cup check valve 792 at cross-sections A-A and B-B in FIG. 21C, respectively. The cup piece 794 of the cup check valve 792 is forked for ease of flexing. The thickness and shape of the cup piece 794 may be varied depending on the flexing needs of the cup piece. Further, the connecting piece 804 may be any shape that connects the upper piece of the cup check valve 792 to the cup piece 794. In the preferred embodiment, the connecting piece 804 is cylindrical so as not to interfere with the flow of fluid through the piston 454.

In another embodiment of the invention, there is provided a means by which to transfer data from the manufacturer to the customer. The manufacturer uses a manufacturing database in order to maintain a record of reagents, master lots, and serial numbers for kits and dispensers. The manufacturing database is an Interbase (client/server) database contained in a single file. The manufacturing database definition consists of domains, tables, views, and triggers. Domains define the variable types and requirements used in tables. Tables define the data that is stored for each record. Views (meta-tables) are accessed as tables but do not contain data. The views collect data from tables. Triggers are programs that are executed on the Interbase server in response to defined events.

Information is stored on the database to define kits (which contain several dispensers) or single dispensers. Each package, whether a kit or a dispenser, will include a barcode identifying the contents. For kits, the barcode will contain the part number, master lot number and serial number. For single dispensers, the barcode will contain the part number, lot number and serial number. Serial numbers are assigned to kits sequentially for each master lot starting at 1 (i.e., the first kit created from each master lot will be assigned serial #1). The package barcodes are separate from the barcodes that appear on the individual dispensers within the package. In particular, in the case of a single dispenser package, the serial on the package barcode label need not match the serial number of the single dispenser contained in the package.

The barcode is encoded with the Code 128 Symbology. The plain text interpretation of the barcode is to appear as standard ASCII text below the barcode. This allows for operator verification of the data obtained by scanning. The three fields on the package label will be fixed in length and combined into a single barcode by concatenation. For the dispensers, one of the fields is a 4 digit product code, which determines the contents of the dispenser, and another one of the fields is a serial number. The serial number is unique to the type of dispenser (i.e., the serial number for each dispenser of a certain type is incremented by one). By scanning in these two fields, the device that programs the touch memory device, which is described subsequently, recognizes the type of dispenser. Moreover, the host device, which obtains the scanned code from the barcode reader on the remote device, which is described subsequently, also determines the type of the dispenser based on the barcode. For a barcode on a kit, there is a field that corresponds to a particular kit form, so that, when the kit barcode is scanned in, the computer determines, through a look-up table, the particular kit form associated with the kit barcode, as described subsequently.

Figure 22:
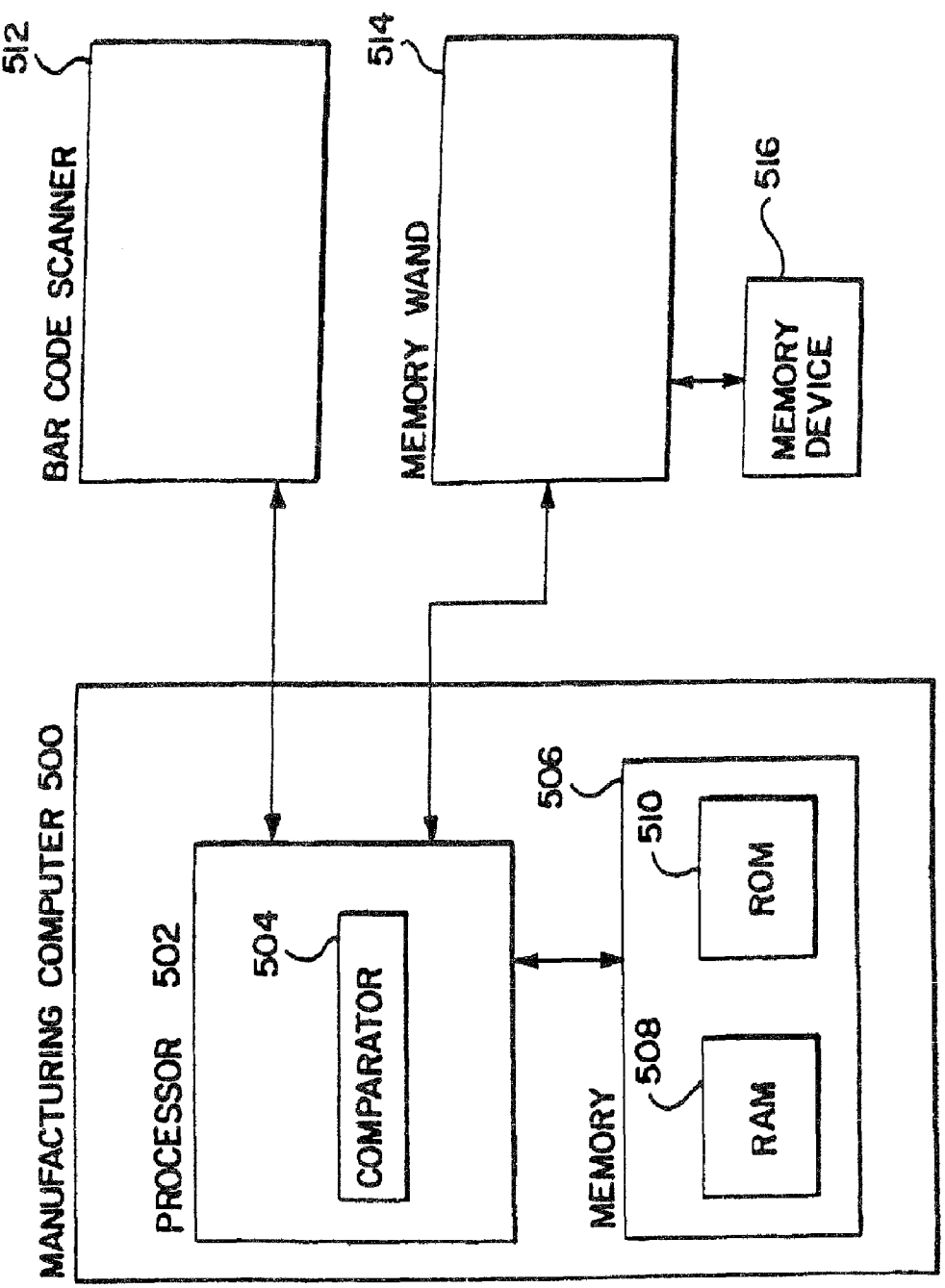
FIG. 22 is a block diagram of the manufacturer's system for programming an external memory device.

Referring to FIG. 22, there is shown a block diagram of the manufacturer's system for programming an external memory device. The manufacturing computer 500 is a typical personal computer, with a processor 502 including a comparator 504, and memory 506 including RAM 508 and ROM 510. As described subsequently, the processor 502 is in communication with a barcode scanner 512 and a memory device 516 such as an EPROM (erasable programmable read only memory). In the preferred embodiment, the processor 502 is in communication with the memory device 516 via a memory wand 514, as described subsequently.

Figure 23B:
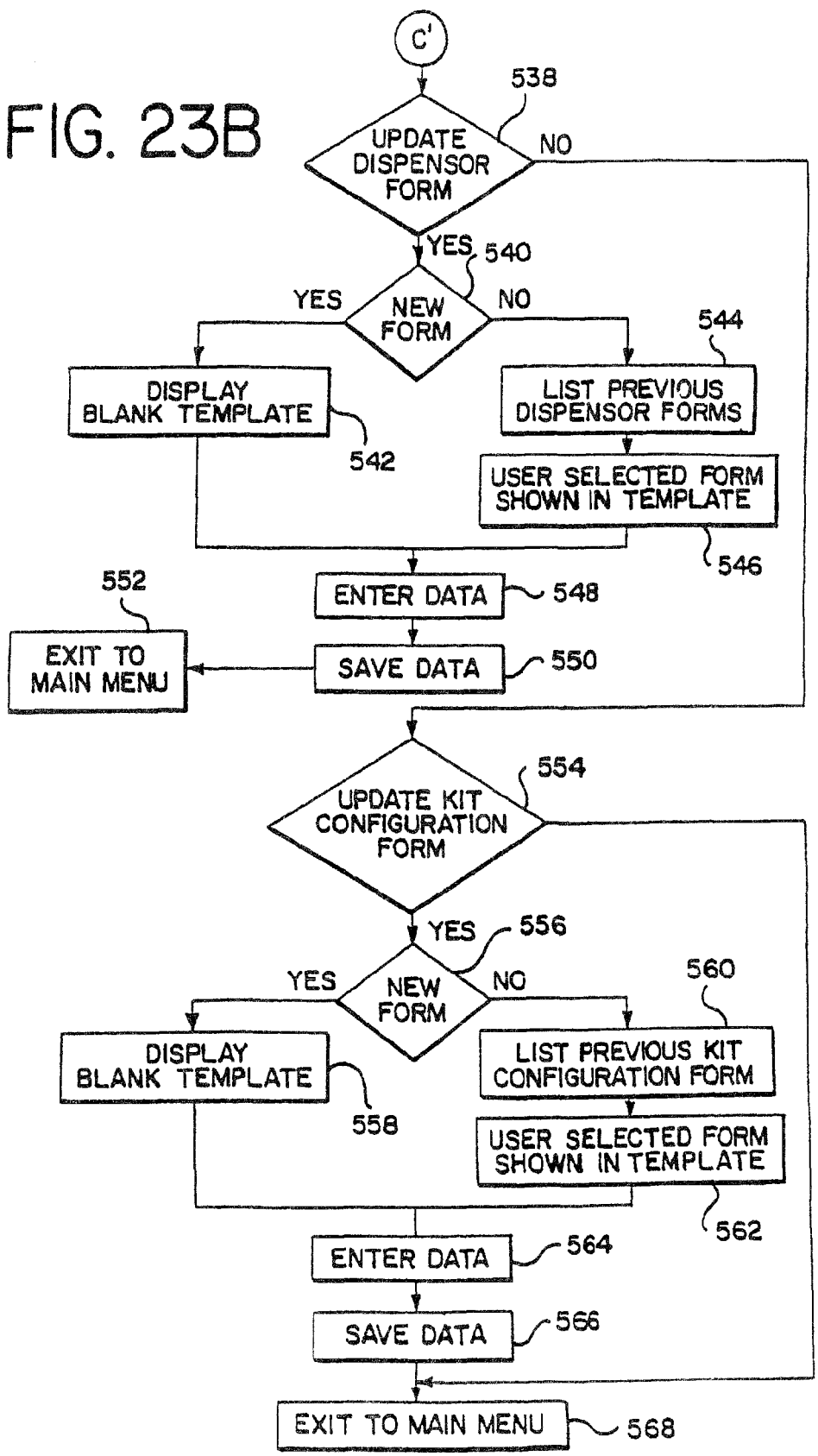
FIGS. 23A and B are flow charts for updating the forms on the manufacturer's reagent database.

As described in Appendix A, there is software that implements the acquisition of data from registration tables, and stores the data into an external memory device. Referring to FIG. 23, there is shown a flow chart for updating the forms on the manufacturers database. The forms are used as templates for the manufacturing database for kits, dispensers, dispenser models, etc., which are later entered to program the touch memory device. The forms include reagents, dispenser models, dispensers, kits and filled kits. For example, in the reagent form, data about a particular reagent, such as the reagent name, group name, etc. may be entered. The dispenser models include user fillable and prefillable dispensers. Referring to FIG. 23, the operator is asked if he or she wishes to update the reagent form 522. If so, the manufacturing database determines if the reagent form is new or old 524. If new, a blank template is displayed for the operator to enter data 526. If a reagent form is to be modified, the reagent template is displayed 528, 530. The contents are entered or modified and the data saved to the database 532, 534. Likewise, the forms may be modified for the dispenser form, which includes data on the part number, reagent, code, whether the dispenser is prefillable, the dispenser model, whether the reagent is active, etc. The operator is prompted whether the form is new 540, and if new a blank template is displayed 542. If old, the previous dispenser forms are displayed 544 and the user selects a form 546. Data is entered 548 and saved 550. The forms may be modified for the kit configuration as well. The kit configuration includes data on the dispensers included in a kit sent to the end user. This information includes the part number, the description of the kit, whether the dispensers in the kit are active, the number of reagents in the kit, and data on the dispensers in the kit. The operator is prompted whether the form is new 556, and if new a blank template is displayed 558. If old, the previous dispenser forms are displayed 560 and the user selects a form 562. Data is entered 564 and saved 566. The forms interact with one another for ease of updating. For example, if the dispenser model is modified, the dispenser form, which is dependent on the dispenser model, is modified as well. Further, if the dispenser is modified, so is the kit configuration, which in turn depends on the dispenser.

Figure 24A:
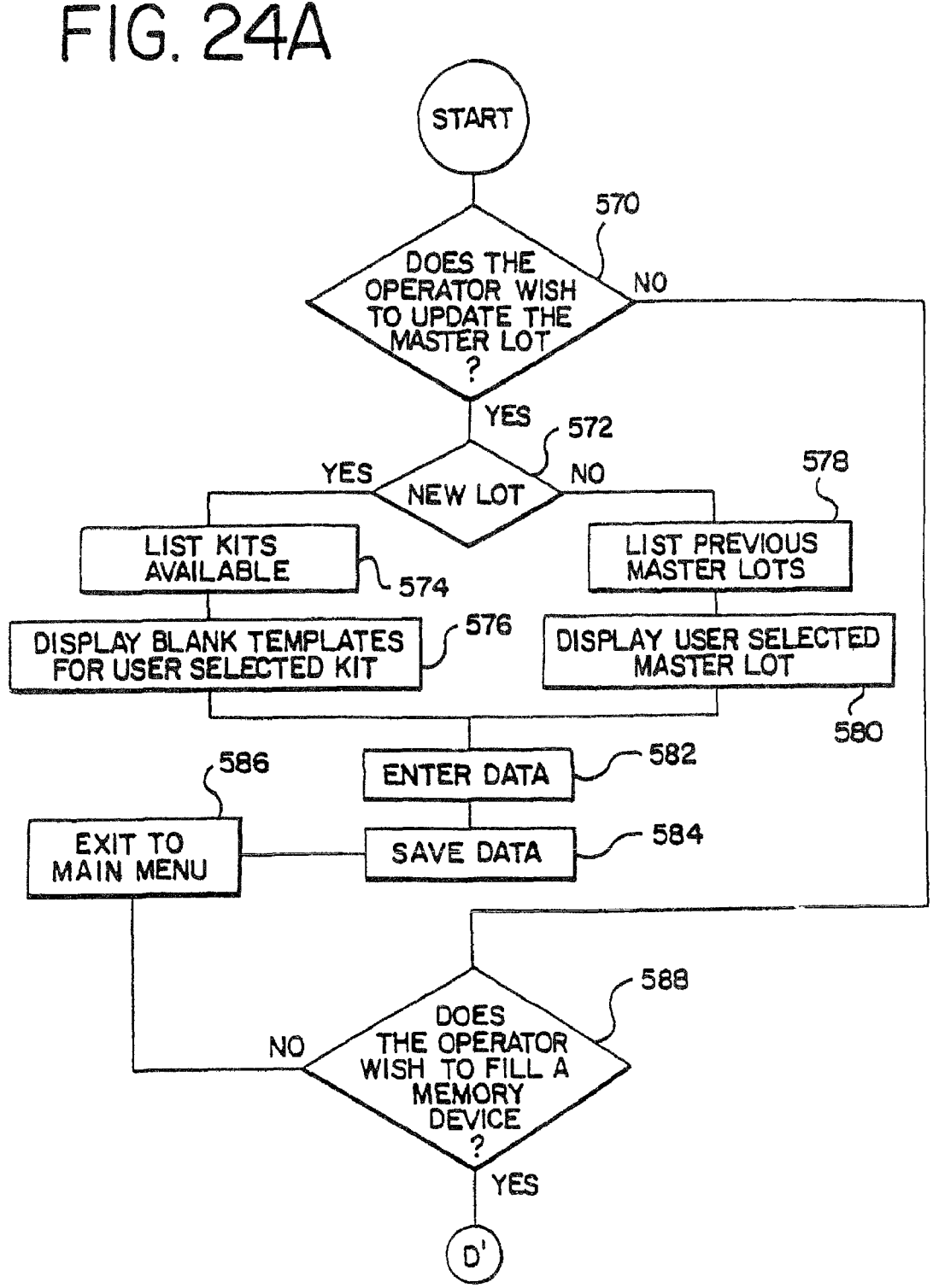
FIGS. 24A and B are flow charts for updating the master lot on the manufacturers reagent database and for inputting data into a memory device.
Figure 24B:
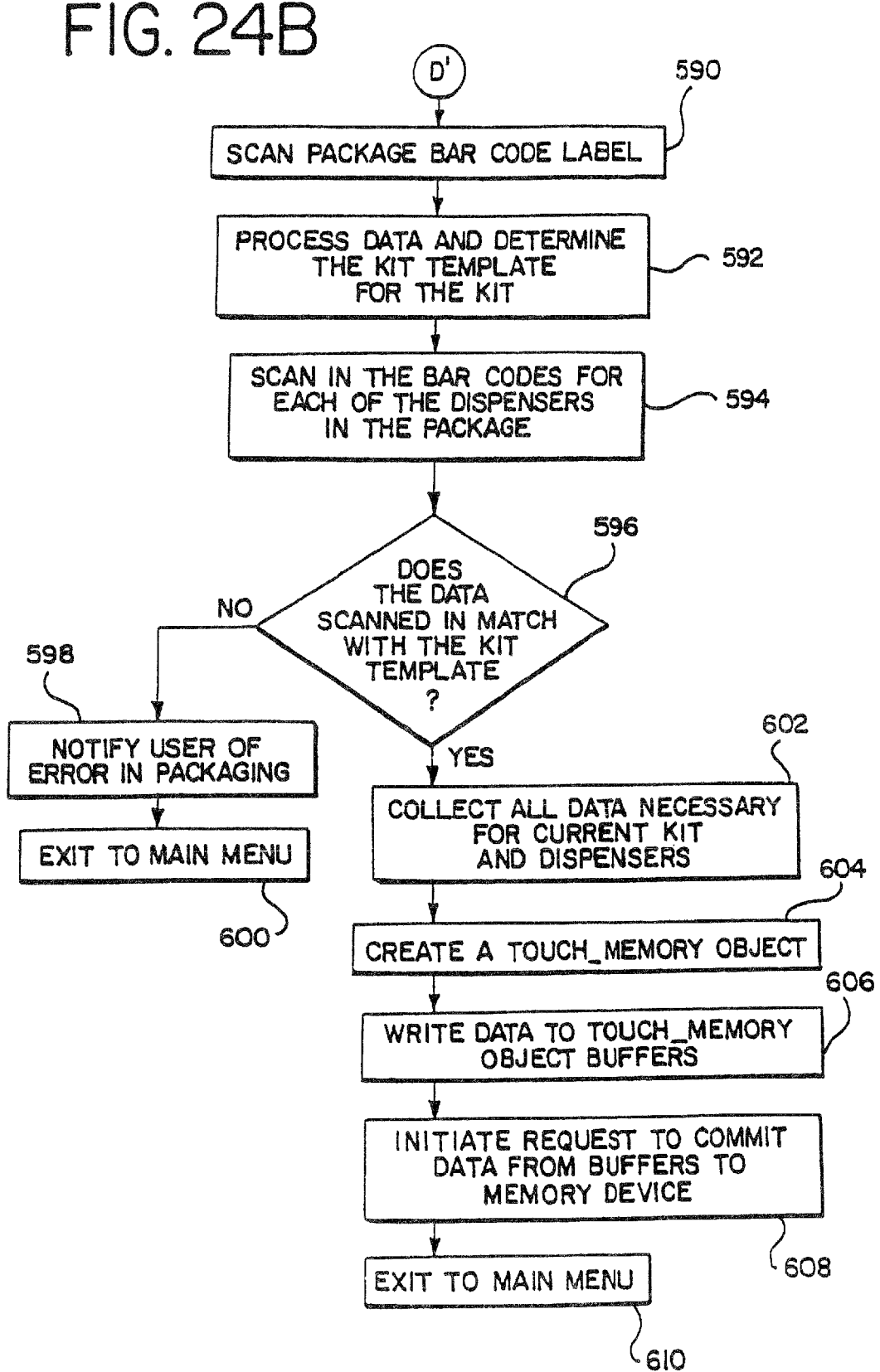

The updating of the master lot and entering data into the memory device is shown in the flow chart in FIG. 24. The master lot form supports assignment of master lot numbers to predefined kits, as well as lot numbers and expiration dates to each of the dispensers in the kit. The expiration date of the kit is the earliest of the expiration dates of the dispensers in that kit. If the operator wishes to update the master lot 570, the manufacturing database determines if the master lot is old or new 572. If new, the list of kits is displayed 574 and a blank template for the user selected kit 576. If old, the previous master lot is listed 578 and the user selected master lot is displayed 580. Data is entered for the master lot 582 and then saved 584.

Once the forms are set, the operator may begin to program the touch memory device 588. In the preferred embodiment, the memory device 576 is an EPROM such as the Dallas Semiconductor DS1985 F5 16 Kbit add-only touch memory device. Other memory devices may be used to store the information and allow the end user to retrieve the information. For example, diskettes may be used as memory devices.

First, the package bar code labels are scanned 590. A Welsh Allyn Scanteam 5400/5700 hand held scanner is used. The scanner need only be configured once to identify the hardware platform and bar code symbology. The scanner is programmed to send a '!' as a prefix character and also a '!' as a suffix character. The prefix is used to differentiate input from the scanner from input from the keyboard. The suffix is used to identify completion of acquisition.

Based on the information scanned from the package, the kit type is determined based on the information in the kit forms 592. In an alternative embodiment, the user is prompted to enter the type of kit. Based on this information, the computer determines the kit type.

The barcodes for each of the dispensers in the package is then scanned 594. Information in the kit form is compared with the information scanned in 596. For example, the number of dispensers in the package is checked. If the number is too high or too low, the user is notified and the memory device is not programmed. Further, if the type of the dispensers in the package does not match the type of dispensers in the kit form, the user is notified and the memory device is not programmed. This is one of the methods to increase the quality control. If there was an error in the packaging of the package, (e.g., an incorrect dispenser was placed in the package), the user will be notified to correct the problem 598.

If the number and type of dispensers are correct, the database collects all data necessary for the current kit and dispensers 602. The touch memory data is programmed into the touch memory device using object oriented programming. To do this, a touch_memory object is created which contains the form in which the memory will be stored 604. The data for the current kit and dispensers is written to the touch_memory object buffers 606. Finally, the touch_memory object buffers are transferred to the touch memory device 608.

In order to program or read the touch memory device, a probe (Dallas Semiconductor DS9092GT) mounted in a hand held wand 514 is used. This wand 514 is attached to the serial port of the manufacturing computer 500 programming the touch memory device 516 through a Dallas Semiconductor DS9097 or DS9097E serial port (DB-25) adapter. In an alternative embodiment that uses a diskette as a memory device, a disk drive is used to transfer the data on the memory device to the computer 500.

Figure 25:
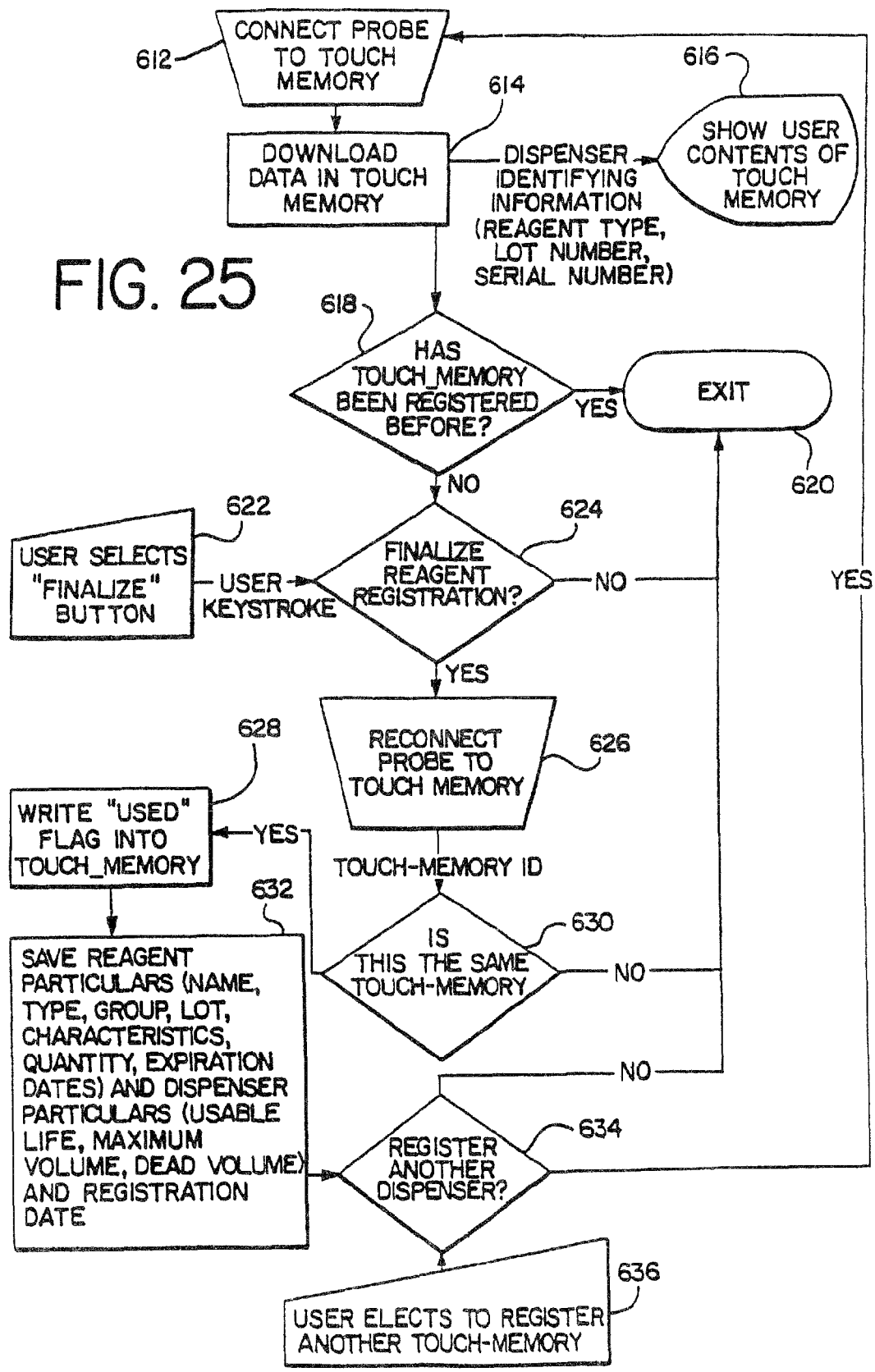
FIG. 25 is a flow chart for downloading data from a memory device to the host system.

At the end user, the memory device accompanies the kit or single dispenser. Referring to FIG. 25, there is shown a flow chart for downloading data from a memory device to the host system. The probe is first connected to the touch memory device 612. The contents of the touch memory device are downloaded to the host computer 614 and displayed to the user 616. It is then determined whether the touch memory device has been downloaded previously 618. This is done based on the contents of the touch memory device. If the memory contents were previously downloaded, a flag is set in the memory contents. Therefore, this kit has already been "used" and therefore should not be reprocessed. The user is prompted whether he or she wants to update the user's databases with the kit/dispenser data 624. If so, the probe is reconnected to the touch memory device 626, verified that it is the same touch memory device by comparing the current downloading with the previous download of data 630. The flag indicating that the touch memory device is "used" is set inside the memory device 628. In this manner, a memory device may be downloaded only once for purposes of security. The contents of the user's databases are updated with information contained in the touch memory device such as name, type, group, lot, serial number, characteristics, quantity, expiration dates for the reagents, and the usable life, maximum volume, dead volume and registration date for the dispenser 632.

Regulations require that a user must maintain a database of the fluids used in staining. Prior to this invention, users were required to manually input data into the database. This process was not only time-consuming, but also prone to error. In contrast, the current invention uses information in the touch memory device to update the required database.

The user database, which is required by the regulations, contains various tables including the registration, receive and quality control tables for use by the operator. Within each of the registration, receive and quality control tables, there are five different types of categories: (1) antibodies; (2) reagents;

(3) kits; (4) consumables, and (5) control slides. Antibodies are chemicals that have living cells within which attach to the patient's tissue. Reagents are non-antibody chemicals that typically contain no living material. Kits, as described above, contain various combinations of dispensers. Consumables are materials such as the Liquid Coverslip™, wash buffer, etc. Each of these materials are regulated in different manners, thereby requiring different information contained within the registration, receive and quality control tables. For example, since antibodies are living material, they are regulated more highly and therefore require additional information in the tables.

The registration table contains the background information for the specific material. For example, the registration table contains the name of the material (antibody, reagent, kit, consumable, or control slide), the manufacturer, the clone number (for antibodies) and other information describing the material. As described previously, one field in the dispenser barcode is the type of dispenser. This information is programmed into the touch memory device, which is subsequently downloaded to the registration table. Therefore, when the barcodes for the dispensers are scanned in preparation for a run, as described subsequently, the registration table is used to determine what type of fluid is contained in the dispenser. This table is updated only when the material is first received.

The receive table is a table which records each time when a certain material is received and the expiration date of that material as well as other information specific to this lot of material including the serial number. Therefore, while the registration table may describe the properties of a certain antibody, the receive table will describe on which dates each dispenser of that antibody was received, the expiration date for that antibody, the serial number and the lot number. This information is used not only to generate reports that are required by regulation, but also to check for the expiration date of the chemical during a run, which is described subsequently.

The quality control table records when a particular chemical was validated. Regulations require that when a new chemical or when a new lot for a previously received chemical is received, the lab must check to make sure the material performs in the expected manner (i.e., the material was processed correctly and not damaged in shipment). To determine if the material is "acceptable" to use in testing on patient tissue samples, end users have tissue samples that are known to test positive with undamaged reagents. The quality control table will track whether the chemical was tested for effectiveness and which tissue sample was used to test the chemical. In this manner, the tables, which are generated in large part by information from the touch memory, allow the end user to comply with the regulations without the need for time consuming data entry.

Other tables are used during a run which provide for better quality assurance in testing. For example, there is a dispenser table that contains, for each dispenser, the pertinent information for quality assurance during a run. For example, for each dispenser with a corresponding barcode (which contains the serial number for the dispenser), the table contains the expiration date, and the number of drops in the dispenser.

Figure 26A:
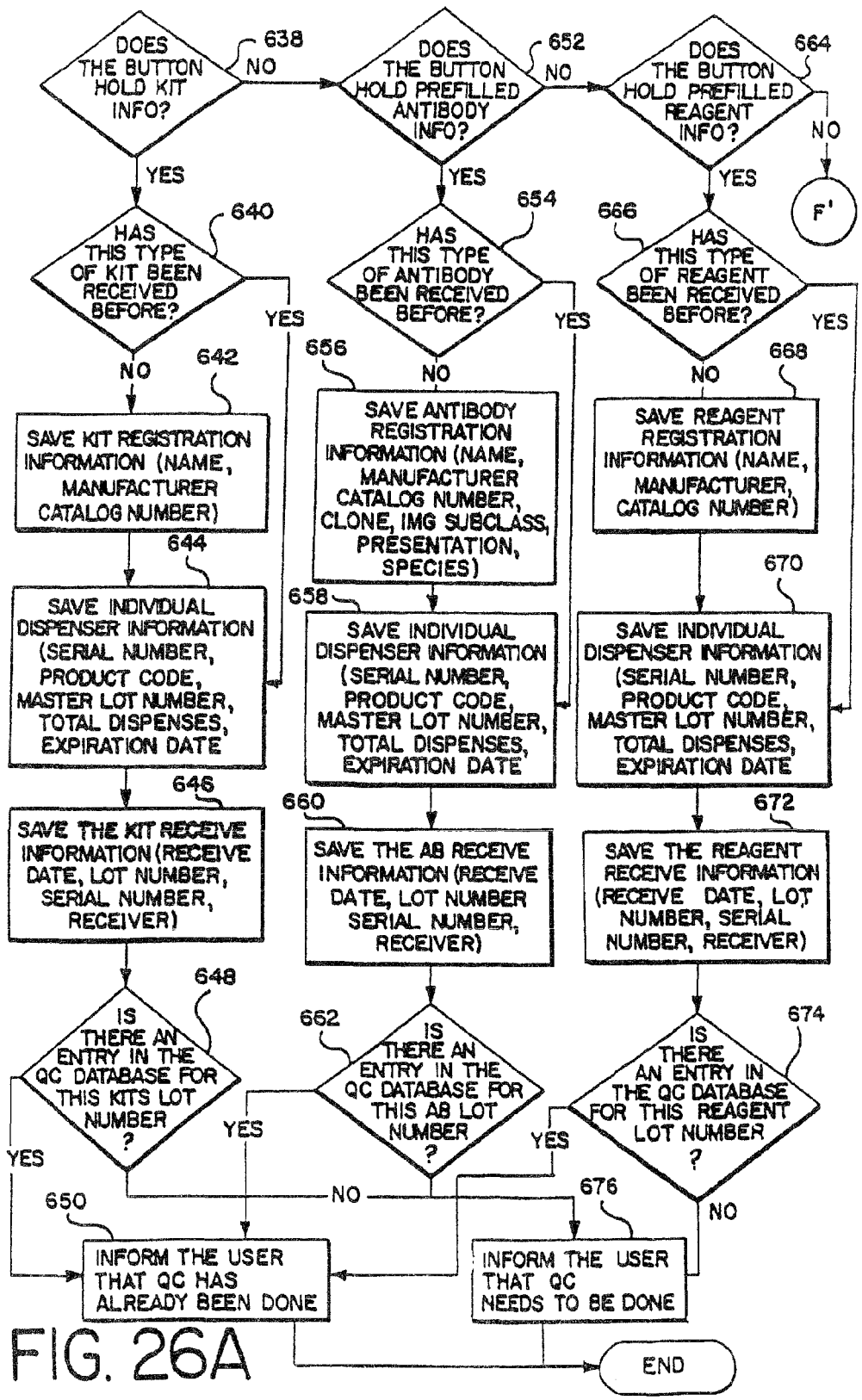
FIGS. 26A and B are flow charts for updating the memory devices of the user through information downloaded from an external memory device.
Figure 26B:
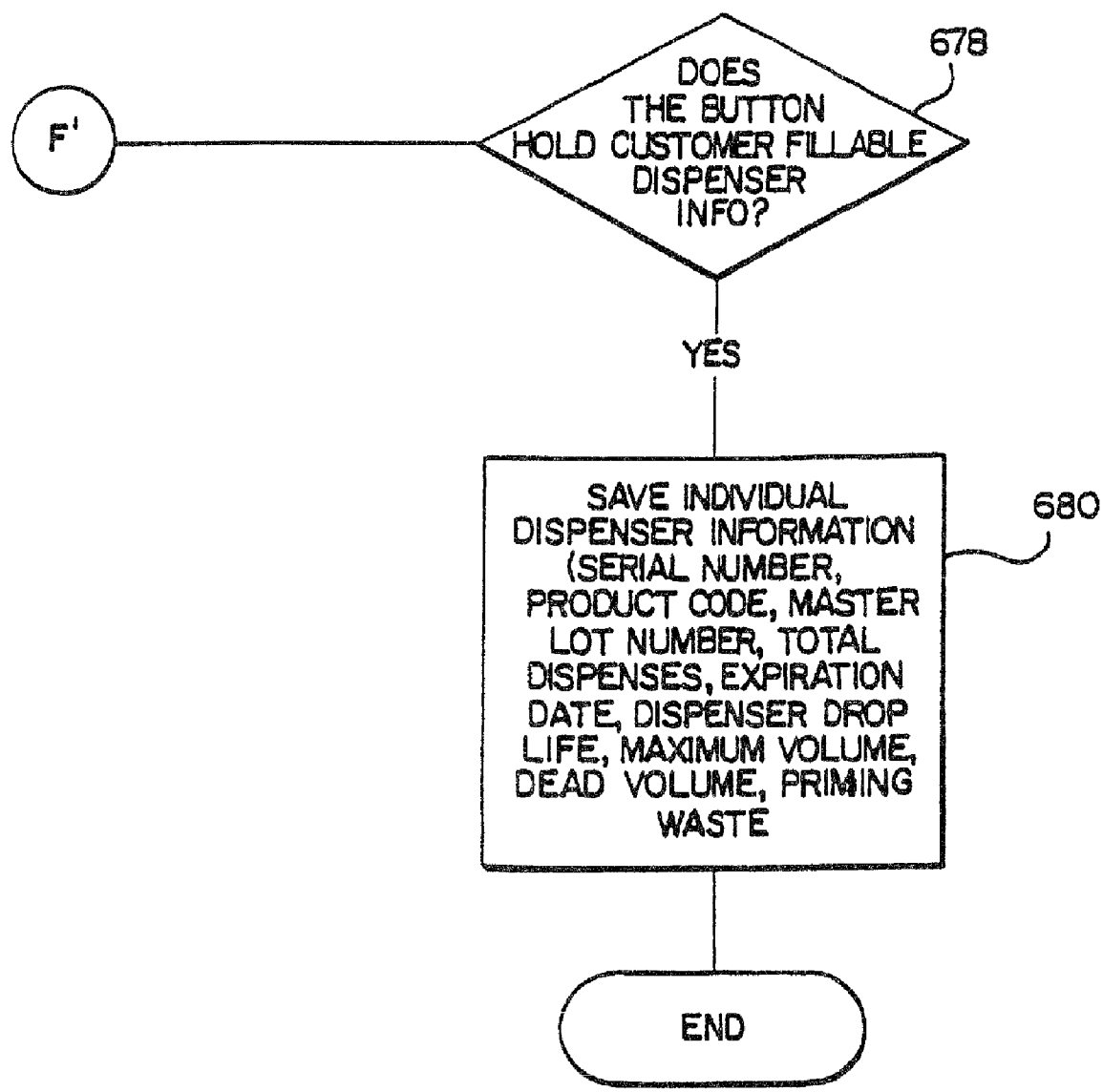

Referring to FIG. 26, there is shown a flow chart for updating the registration, receive and quality control tables on the host computer for use by the operator. Based on the data in the touch memory device, the computer determines whether the touch memory holds kit information, prefilled antibody information or prefilled reagent information. In particular, the computer may examine the format of the data in the touch memory device and determine what type of data the touch memory object holds. In the alternative, the touch memory device may specifically state whether the data relates to kit information, prefilled antibody information or prefilled reagent information. In particular, one of the fields in the touch memory device signifies what is the type of information.

Dispenser/kit information is read from the touch memory device. The computer determines if the touch memory device holds kit information 638. If so, the touch memory device searches the registration table to determine if the kit was previously received 640. If the kit was not received previously, the registration table must be updated with the kit registration information (i.e. background information) such as manufacturer and catalog number 642. This kit registration information is obtained from the touch memory device. The individual dispenser information within the kit, also obtained from the touch memory device, is updated in the dispenser table including the serial number, product code, master lot number, total dispenses (by number of drops) and expiration date 644.

The receive table is also updated to include the receive date, lot number, serial number, and receiver 646. The receive date is generated based on the date in the host device processor and the serial number is obtained from the touch memory device. The receiver field in the receive table is the person that has input the data from the touch memory device. In the preferred embodiment, the host device 32 determines who is currently logged on to the host device and writes the user's name as the receiver.

The quality control table is searched to determine if there is an entry in the table for this kit's lot number (i.e., if this is a new kit or a new kit lot number) 648. If the kit lot number (as obtained from the touch memory device) has already been quality control tested, the user is informed that this has already been done 650. If not, the user is informed that a quality control test must be performed 676. In an alternative embodiment, a separate look-up table is used to select known tissue samples to test the effectiveness of a received chemical received. Based on the chemical received, the known tissue samples are suggested to the user to test the effectiveness of the chemical in order to update the quality control table.

The computer determines if the touch memory device holds prefilled antibody information 652. If so, the touch memory device searches the registration table to determine if the antibody information was previously received 654. If the antibody information was not received previously, the registration table is updated with the antibody registration information (located in the touch memory device) such as name, manufacturer, catalog number, clone, 1 mg subclass, presentation, and species 656. The individual dispenser information is also updated in the dispenser table including the serial number, product code, master lot number, total dispenses (by number of drops) and expiration date 658. The receive table is updated to include the receive date (as determined from the host device), lot number, serial number, and receiver 660. The quality control table is searched to determine if there is an entry in the table for this antibody lot number (i.e., if this is a new antibody or a new antibody lot number) 662. If the antibody lot number has already been quality control tested, the user is informed that this has already been done 650. If not, the user is informed that a quality control test must be performed 676.

The computer determines if the touch memory device holds prefilled reagent information 664. If so, the touch memory device searches the registration table to determine if the reagent information was previously received 666. If the reagent information was not received previously, the registration table is updated with the reagent registration information (located in the touch memory device) such as name, manufacturer, and catalog number 668. The individual dispenser information (located in the touch memory device) is updated in the dispenser table including the serial number, product code, master lot number, total dispenses (by number of drops) and expiration date 670. The receive table is updated with information from the touch memory device to include the receive date, lot number, serial number, and receiver 672. The quality control table is searched to determine if there is an entry in the table for this reagent lot number (i.e., if this is a new reagent or new reagent lot number) 674. If the reagent lot number has already been quality control tested, the user is informed that this has already been done 650. If not, the user is informed that a quality control test must be performed 676.

The computer determines if the touch memory device holds customer fillable dispenser information 678. If so, the individual dispenser information (located in the touch memory device) is input including the serial number, product code, master lot number, total dispenses, expiration date, dispenser drop life, maximum volume, dead volume and priming waste 680. In an alternative embodiment, the user is prompted to input the amount of liquid, in milliliters, which is placed in the dispenser. This amount in milliliters is converted into a number of drops and stored in the table. The user may, at a later time, fill the user finable dispenser and, at that later time, update the dispenser table with the amount of fluid put in the dispenser.

Figure 27:
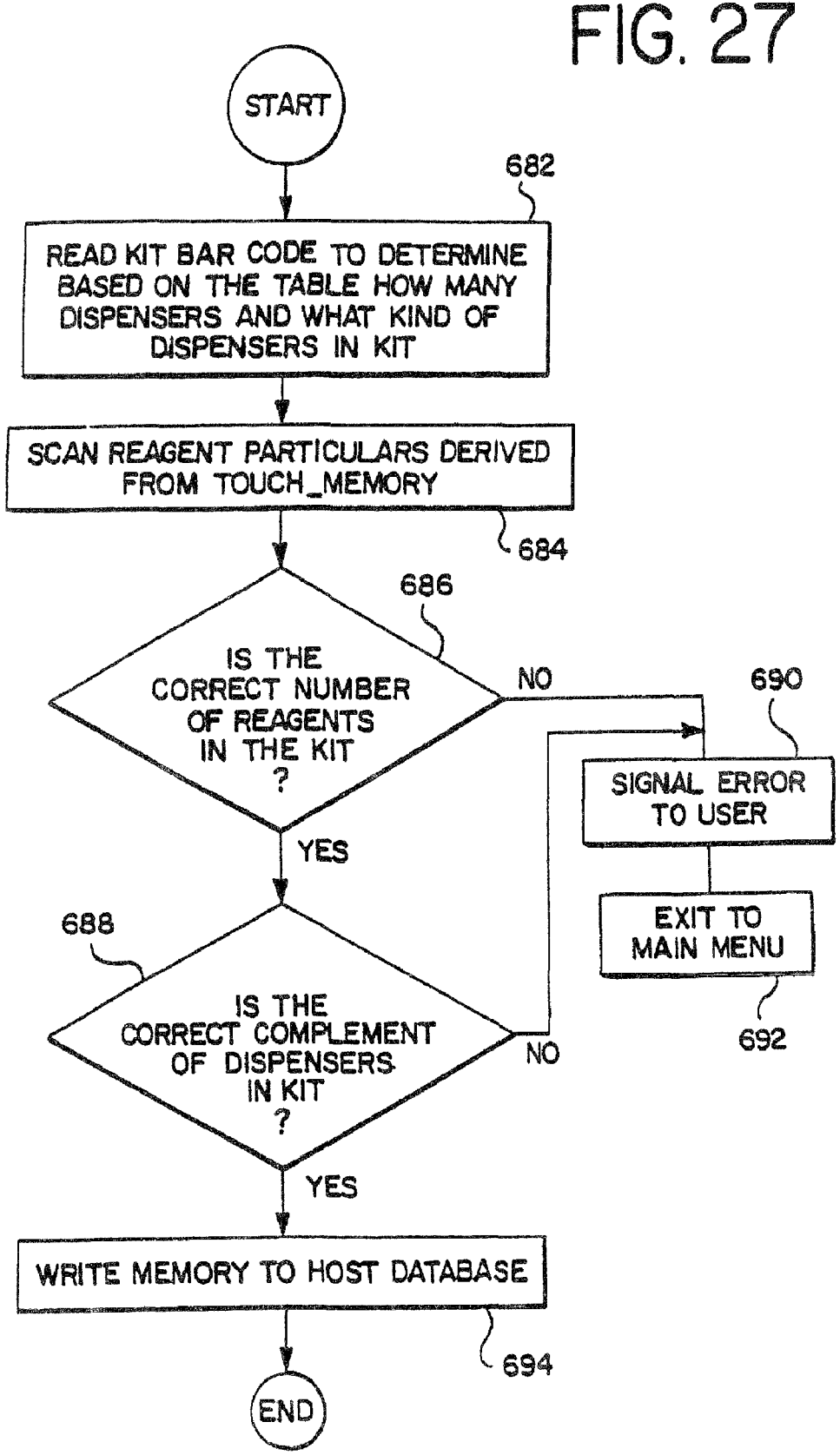
FIG. 27 is a flow chart for determining if the kit/dispensers for use by the operator is the correct number and correct complement.
Figure 28B:
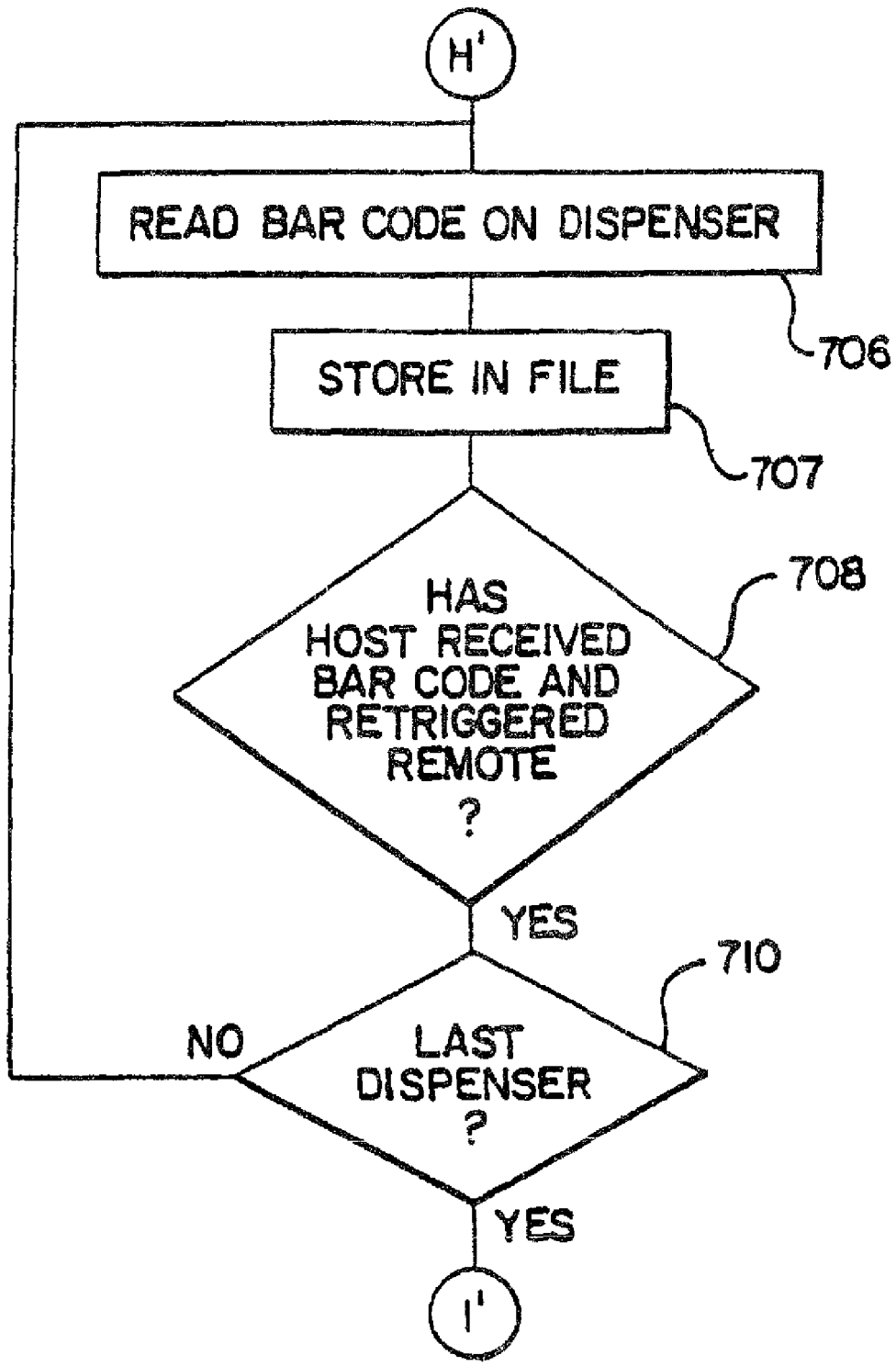
Figure 28C:
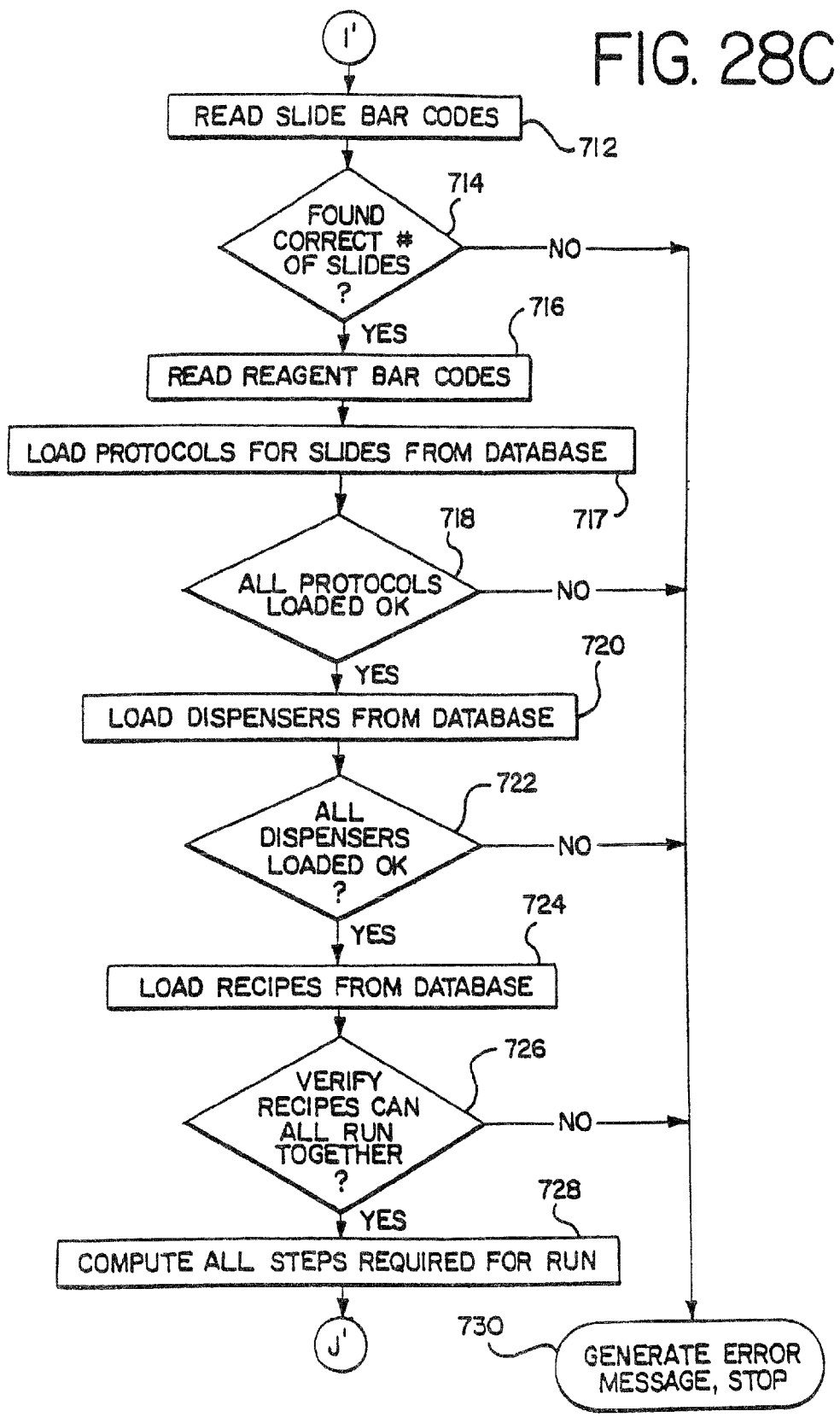
Figure 28D:
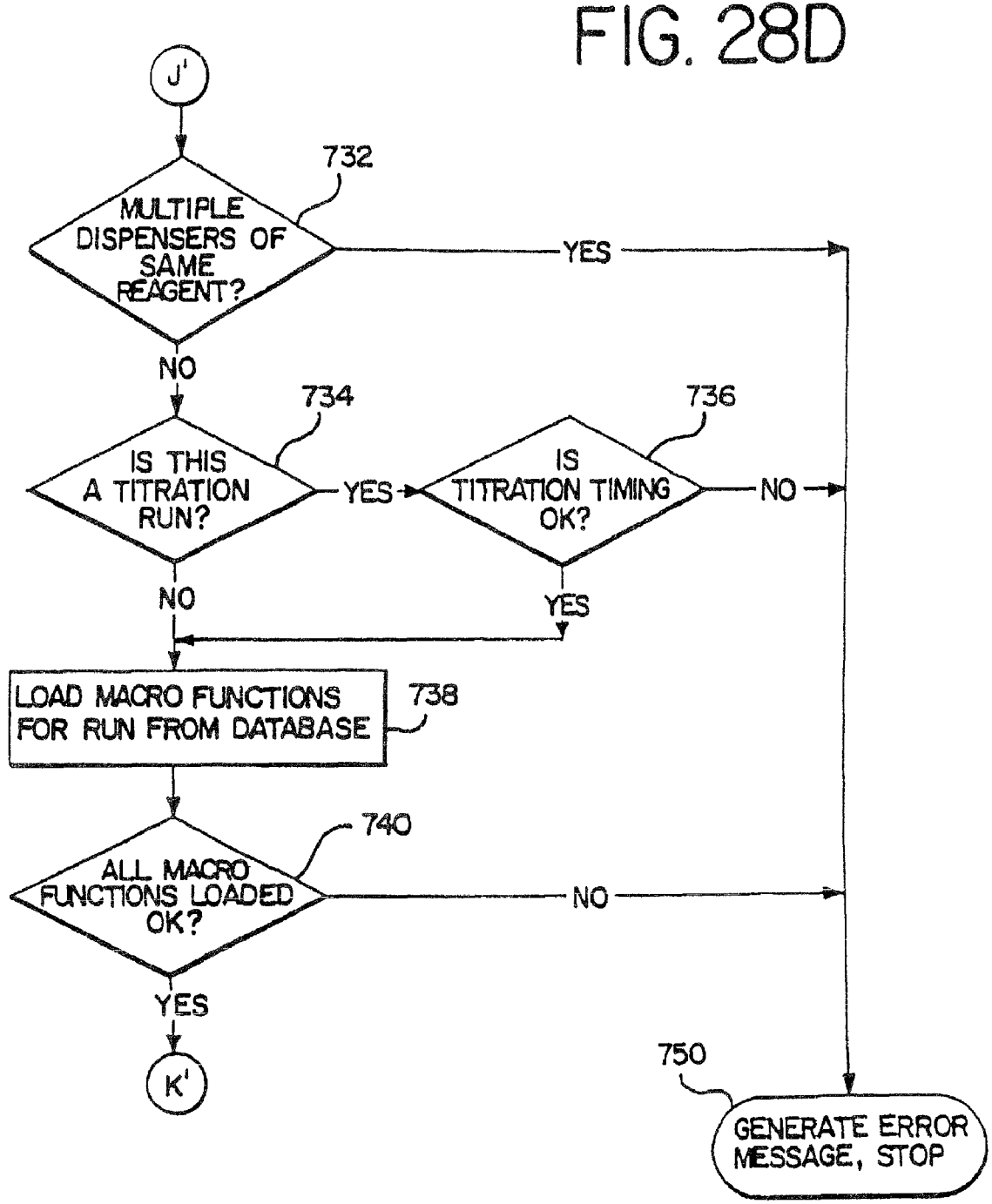
Figure 28E:
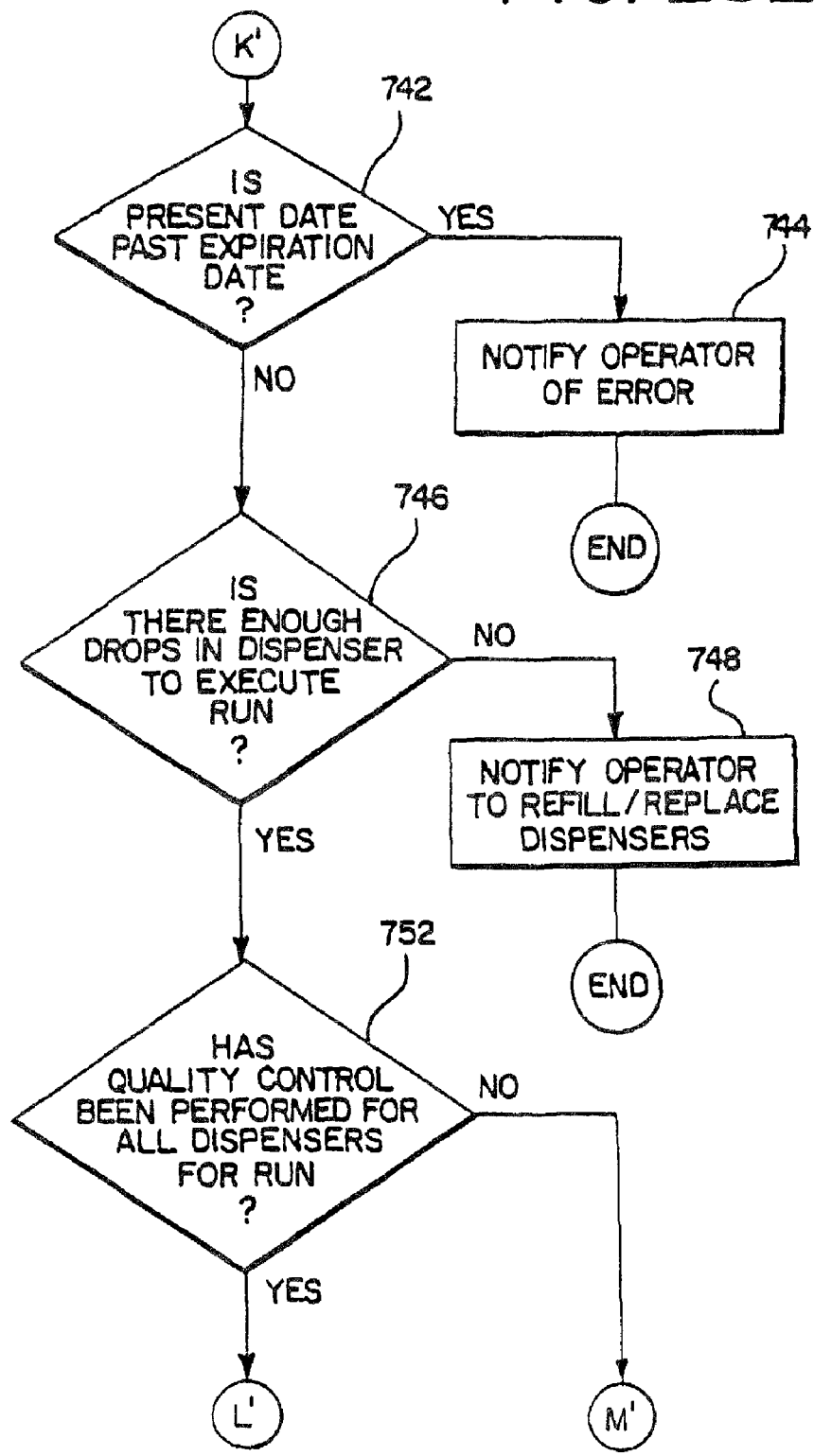
Figure 28F:
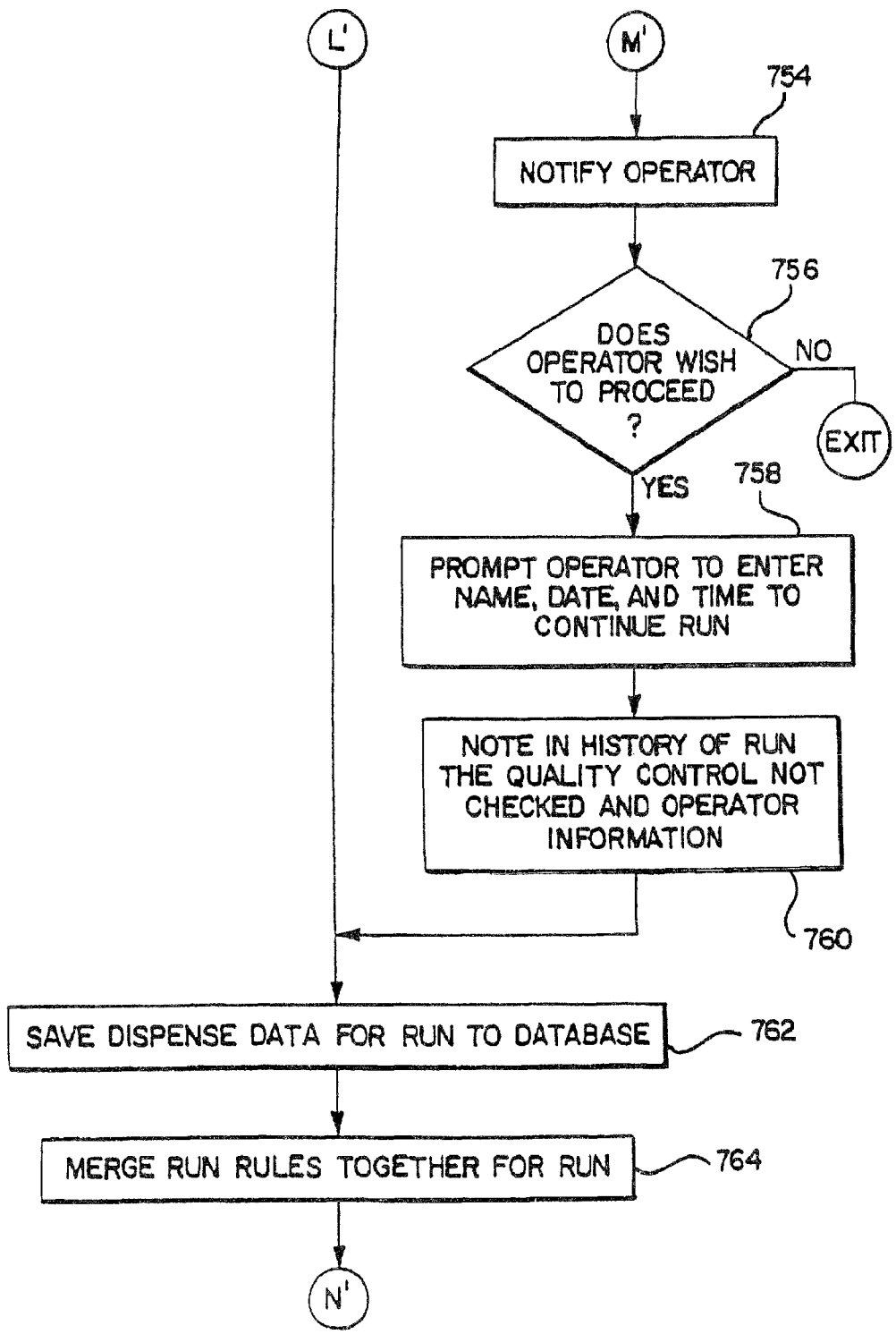
Figure 28G:
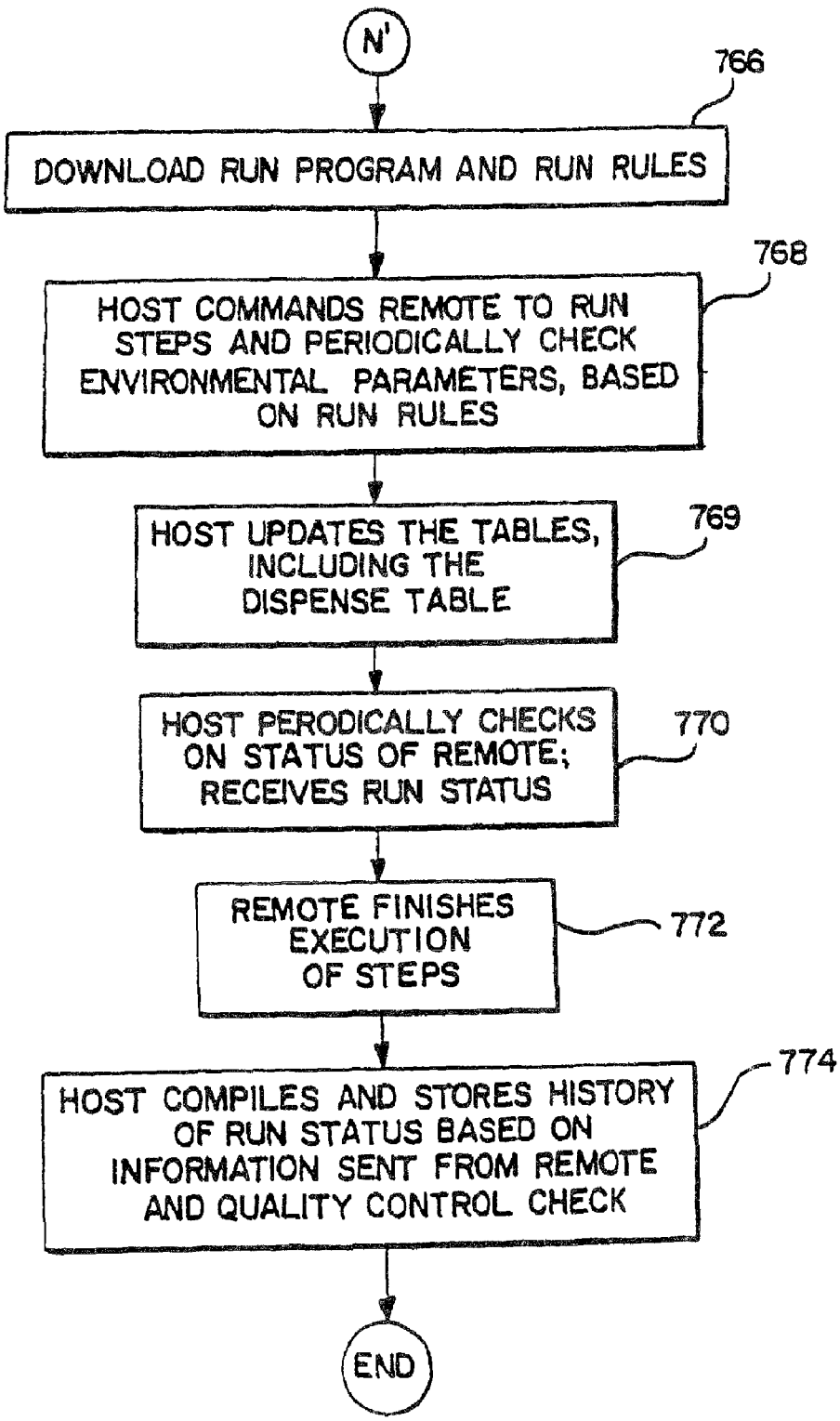

In an alternative embodiment of the invention, the host device performs a series of checks using the information from the touch memory. Referring to FIG. 27, there is shown a flow chart for determining if the kit/dispensers for use by the operator is the correct number and correct complement, similar to the check performed while programming the touch memory device, as described in FIG. 24. The kit barcode information from the touch memory is read to determine the type of kit and dispensers contained in the package 682, 684. Based on this barcode information, there is a look-up table which describes the number of reagents in the kit and the type or complement of reagents in the kit. This historical information in the look-up table is compared with what was actually sent in the package. If there is a discrepancy as to the number of dispensers in the kit or in the type of reagents in the kit 686, 688, the user is notified and the user's database is not updated with the kit barcode information 690. In this manner, checking whether the proper dispensers were included in the kit may increase the quality control.

After the downloading of the data from the touch memory device, the host device 32 and remote devices 166 may execute a run. As described previously, the host device 32 and remote devices 166 are modular in design. The host handles higher level system functions whereas the remote devices 166 perform the execution of the steps for staining. This modularity of design utilizing a personal computer as a host device 32 is beneficial in several respects. First, the host computer can be used to start runs on other remote devices 166. Second, the host device 32 can periodically update the software more efficiently on the remote device 166 based on upgrades in the operating system. For example, the lowest level code in the remote devices 166, which handles the basic input and output for the remote device 166 and the execution of programs, may be updated based on changes in error messaging, changes in output device design (such as different types of valves), and changes in the messaging protocols between the host and the remote. Third, the modularity multiplies the number of staining modules that may be run by a single machine. Fourth, since the host device 32 is comprised, in the preferred embodiment, of a personal computer, the host machine may be easily upwardly compatible, as opposed to previous standalone staining modules. Further, the personal computer can be integrated with a network environment to integrate with other computers. For example, there is a trend in hospitals to standardize the computer hardware used and to interconnect the computer hardware. The host device 32 may be connected to a hospital network, receiving commands from other computers on the network to execute a staining run, described subsequently, or sending results of a run to another computer on the network. Fifth, the host device 32 may serve as a platform through which various staining modules may be integrated. For example, there are various types of staining modules, some of which use dispensers versus vials, some of which use horizontal slide trays versus vertical slide trays, etc. The host device 32 may be integrated with a variety of staining modules, downloading programs to the different modules, described subsequently, depending on the particular configuration of the module. Sixth, the remote device 166, as a modular piece in the automated biological reaction system, may be serviced more easily. Instead of having a large machine dedicated to staining, the remote device 166 is smaller and can be shipped through the mail easily. In this manner, when an end user has difficulty with a remote device 166, the user may receive a second remote device through the mail, and send the faulty remote device back to be fixed. Therefore, the user need not rely on on-site maintenance for the remote device, and the attendant cost associated with on-site maintenance.

The host device may execute three different types of runs. The first run is a test run, which is described subsequently. The second run is a system run, whereby the remote device 166 reads the barcodes for the slides or the dispensers, or other non-staining functions required to setup a staining run. The third run is a staining run whereby the remote device 166 stains the slides. The second and third runs are described in FIG. 28. When executing a run, the host downloads a sequence of steps in a run program to the remote device 166. The run program is comprised of two separate pieces: (1) a main program (defined as macro 0); and (2) subroutines (defined as macros 1-255). The main program is composed of, but is not necessarily limited to, calls to the subroutines. Therefore, the entire length of the run program through calls to subroutines is less than a line by line execution of the entire program. For example, if a subroutine is called 50 times, the main program calls the subroutine 50 times rather than downloading a program which includes the code for the subroutine 50 times. In addition, the subroutines are defined by a programming language of thirty-one low-level commands which perform basic functions on the remote such as checking the timer, turning on an output such as a valve or a heater, or moving the carousel. When downloading the run program, the macros are downloaded as needed to execute a single run.

In addition to downloading a run program, the host device 32 downloads the sensor monitoring and control logic called the run rules. This program is made up of a series of continuous checks that must be done during the execution of the run program. As discussed previously, one of the checks is the upper and lower limit of the temperature of the slides. If, during a run, the environmental temperature is below the lower limit, as indicated by slide temperature monitoring sensor 68, the slide heater 302 is turned on. Likewise, if the environmental temperature is above the upper limit, as indicated by slide temperature monitoring sensor 68, the slide heater 302 is turned off. Another run rule relates to the opening of a system door. Additional run rules relate to the environment in which the remote device 166 executes the run. If any of the sensors are outside of the boundaries sent by the run rules, the remote device 166 sends a message which is retrieved by the host device 32. As discussed generally in FIG. 5C with respect to placing messages in the queue, the first priority is the execution of the steps in the run program. In addition to this, where spare processing is available, the host device 32 polls the remote device 166 for status. The host device 32 does this approximately every 1½ seconds to receive the status of the remote device 166 including the current temperature of the remote device 166, current step number being processed in the run program, elapsed time of the run, and any errors during the run. The host device 32 makes a record of any anomalies during the remote device run and prints the final report at the end of the run.

An example of a staining run is shown in flow chart form in FIG. 28. In preparation for a run, the operator determines the type of staining for the particular slides. Each slide has a barcode attached to it. Based on this barcode, the operator may program the type of staining. In order to assist the operator, the host device provides a set of recipes. For example, one test is a DAB paraffin test. Because this test is commonly used, the user may assign the barcode for the particular slide to that recipe thereby choosing the particular steps to perform the test. In addition, some of the recipes require the operator to enter certain parameters, called protocols. For example a protocol may be the specific temperature for the test or the time period for heating. In contrast to the protocols, the recipes define steps which the user does not control. For example, turning on valves, heating the slides, etc. are operations which the users cannot alter. In an alternative embodiment, each barcode on a slide may be standardized In order to simplify the procedure. For example, if the staining for the slide is to test for prostate cancer, a particular field within the barcode is placed on that slide which is used for every slide which is to be tested for prostate cancer. In that manner, the user is not required to enter a recipe for the particular slide, but rather the reading of the barcode determines the type of test.

After the operator has entered the recipes and protocols corresponding to each slide barcode for the staining run, step 695 in FIG. 28, the host device 32 may prepare for a staining run.

After the inputting of the recipes and the protocols, and prior to executing a run, the operator is prompted by the host device 32 (696). The host device first questions whether there is sufficient buffer solution in the wash buffer bottle 246, whether there is sufficient Liquid Coverslip™ in the Liquid Coverslip™ bottle 244, whether the level of waste in the waste tub 254 is acceptable, and whether the reagents and reagent tray 10 is loaded. The operator is then prompted for the number of slides that are loaded on the slide tray.

The first run is a system run to read the barcode on the slides. The operator then begins the run by downloading the file of steps to read the barcode on the slides and to wait for the host device 32 to retrieve the barcode 697. The remote device reads a barcode on the slide 698, stores the barcode in a file 699, to be used subsequently, then waits for the host device 32 to retrieve the barcode and retrigger the remote device 166 to read another barcode on the slide 700. The remote device 166 does this until the last slide is read 702.

The second run is another system run wherein the host device 32 downloads the run program and run rules in order to read the barcodes on the dispensers 704. Similar to the first system run, the remote device 166 reads a barcode on the dispenser 706, stores the barcode in a file 707 to be used subsequently, then waits for the host device 32 to retrieve the barcode and retrigger the remote device 166 to read another barcode on the dispenser 708. The remote device 166 does this until the last dispenser is read 710.

The host device 32 then reads the slide barcodes already stored in the file 712. If the number of entries in the file is different from the number previously entered by the operator (696), as performed in the loop at step 698, an error message is generated 730. This is done since the barcode reader, at times, may not read one of the barcodes on the slide. In that case, the run is stopped.

The host device 32 then reads the barcodes for the reagents already stored in the database 716. Based on the barcodes, the host device loads the protocols for the slides from the database. For each specific recipe, there are a series of macros which are to be executed by the remote device 166. In the case of a DAB paraffin test, a lookup table indicates the series of steps or macros. As discussed previously, there are macros from 1 to 255 which define basic operations of the remote device 166. For the specific task of a DAB paraffin test, the look-up table includes all the necessary macros, in the proper sequence, to perform the test. Based on these macros, the host device 32 determines the types of reagents and amount of drops required to execute the steps 714. Moreover, in creating the run program, calls to the macros are included in macro 0 and macros 1-255 which are to be called are included after macro 0. All the protocols for the particular recipes are loaded and determined if they exist in the database 718. Those protocols were previously entered at step 695. If so, the host device loads data from the dispense table 720 and determines if all of the dispensers are present and loaded 722. If so, the recipes are loaded from the database 724. The host device 32 then verifies that the recipes can be run together 726 (i.e., whether there are any procedures which are incompatible or unsynchronized). For example, if there are two recipes which dictate the temperature of the slides (where the slides are in close proximity), and the temperatures are different, the two recipes cannot be executed; therefore, an error message is generated 730. The steps for the run are then computed 728. Because there are several slides being tested, and each slide has a series of steps associated with it, the host device 32 generates the run program which can execute all the steps for all of the slides. The host device 32 is constrained by being able, for example, to mix with the vortex mixers 271 at a certain station on the slide carousel 24, to dual rinse at a certain station, to add fluid at the volume adjust, etc. Based on these constraints, the run program is generated which tells the remote to execute the steps in the proper sequence at the proper station 728.

The host device 32 determines if there are multiple dispensers of the same reagent 732. If so, an error message is generated since, for quality control purposes, dispensers from the same kit may only be used in a run. In addition, if a step requires applying two different reagents at the same station, the host device 32 requires that the reagents be next to each other. Otherwise, it would take too long to move the carousel and dispense both reagents. As a guideline, each step should be performed within 6 seconds in order to speed up the process of staining.

The host device 32 then determines if this is a titration run 734. In a user filled dispenser, the user may wish to test varying concentrations of reagent in the fluid dispenser. If so, the user executes a titration run whereby the user is allowed, via the program, to stop the run in the middle and titrate different concentrations. The amount of time for the titrations must be short enough so that the slide will not dry out 736. Otherwise, an error message is generated 750. The macro functions are loaded from a database for the run 738 and determined if all the macro functions loaded properly 740.

The host device 32 determines, based on the dispenser table, whether any of the dispensers are past the expiration date 742. If so, the operator is notified 744. Similarly, the dispenser table is checked to determine if the dispensers have sufficient fluid to conduct the run 746. If not, the operator is notified to refill or replace the dispensers 748. Optionally, quality control can be checked to determine if all of the dispensers have been tested under quality control protocols 752.

Therefore, the host device 32 looks up in the dispenser table 716, described in FIG. 26, to determine if the reagents necessary (1) are past their expiration date; (2) are present to perform the run; (3) have enough drops in the dispensers to execute the run; or, optionally, (4) have been tested for quality control. If any of the first three conditions fail, the run cannot be executed and the operator is notified (i.e., one of the dispensers is past its expiration date, one of the dispensers is missing, or one of the dispensers is low on fluid).

Optionally, for quality control purposes, the dispenser table is searched to determine if quality control was performed on the dispenser 752. If it has not yet performed, the operator is notified 754 and asked if he or she wishes to proceed 756. If the operator wishes to proceed, he or she must enter his or her name, and the date and time in order to continue the run 758. Finally, when the run is executed, the information entered by the operator is included in the history of the run, described previously, to indicate that at least one of the dispensers had not been tested in compliance with the regulations, but that the run was performed anyway 760. In this manner, the quality of the run may be increased due to monitoring of the dispensers used in the testing of the tissue samples. The host device 32 then saves the dispense data for the run to a database 762 and merges the run rules, which determine the operating environment of the run, together for the run 764. The host device 32 downloads the run program and the run rules for the current staining procedure 766. The host device 32 commands the remote to run the steps and to run the checks or the run rules 768. The host device 32 then updates the tables based on the execution of the run. For example, the host device 32 decrements the number of drops in the dispenser table for each of the dispensers used in the run 769. As discussed previously, the host device 32 periodically checks the status of the remote device 770. After the remote device 166 finishes execution of the run program 772, the host device 32 compiles the history of the run and stores the information sent from the remote 774.

The host device 32 also communicates with the remote devices 166 by reading and writing information regarding the operation of the remote devices 166. For example, the host device 32 downloads a command indicating to the remote device the amount of time (in 10's of milliseconds) the valve 248G for the volume adjust line is on. This value is stored in non-volatile RAM on the remote device 166. Further, the host device 32 may poll the remote device 166 to send its stored value for the volume adjust time stored in non-volatile RAM. Other information, such as the slide temperature monitoring sensor 68, buffer heater temperature sensor 66 and system pressure transducer 290, as described in FIG. 6A, may be read by the host device 32 and may be calibrated by the host device 32. When reading the sensor information from the remote device 166, the calibration data is sent back to the host. Calibration data is used to adjust for constant errors inherent in each temperature sensor and pressure transducer. In order to correct for errors, the host device 32 writes to the remote device 166. For example, when calibrating the pressure sensor, the host device 32 commands the remote device 166 to perform span calibration of the system pressure transducer 290 at the preset pressure of 13.0 psi. The remote device 166 registers the current raw pressure as the 13.0 psi analog to digital point.

Referring to FIG. 29, there is shown a flow chart of the testing run for the remote device. One of the commands or steps downloaded to the remote device is a test command 776. The remote processes the commands in the run program 778 until the remote device 166 receives the test command 780. The remote device 166 then waits until a button 295 is pressed on the remote device 782, as described in reference to FIG. 6A. When the button 295 is pressed, the remote device 166 re-executes the run program, and then waits for the button 295 to be depressed again. In this manner, the operator may test individual steps or commands by pressing the button 295 and re-executing the previous set of commands. In an alternative embodiment, the remote device 166 interprets the test mode as a means by which to single step through the program. Every time the button 295 is pressed, the remote device 166 executes a command. In this manner, the operator may step through the run program and determine if there are any errors in the sequence of steps.

From the foregoing detailed description, it will be appreciated that numerous changes and modifications can be made to the aspects of the invention without departure from the true spirit and scope of the invention. This true spirit and scope of the invention is defined by the appended claims, to be interpreted in light of the foregoing specification.

We claim:

1. A fluid dispenser comprising:
   a barrel having a reservoir chamber, the barrel having an upper portion and a lower portion;
   a cap located on top of the upper portion of the barrel and connected to the reservoir chamber, the cap having an external surface with at least one hole therethrough;
   a valve comprising a biasing member and a hole sealer, the valve being located in the hole in the cap at the point where a downward force is applied against the cap;
   a coupler having a dispense chamber, the coupler being coaxial with the barrel and wherein the barrel lower portion moves into the dispense chamber during dispensing of fluid; and
   a vent located between the cap and the reservoir chamber, the vent including a vent opening and a vent material composed of oliophobic material.

2. The fluid dispenser of claim 1 wherein the valve is oriented with the biasing member contacting the external surface of the cap, and the hole sealer located in and in sealing relation to the hole.

3. The fluid dispenser of claim 1 wherein the valve comprises a single-piece umbrella-shaped valve having a biasing portion, a stem and a seal located in the cap hole.

4. The fluid dispenser of claim 1 wherein the hole sealer is a bulge substantially spherical in shape.

5. The fluid dispenser of claim 1 wherein the external cap surface further comprises a raised surface that mates with the biasing portion of the valve.

6. The fluid dispenser of claim 5 wherein the raised surface further comprises breaks in the raised surface that function as air passageways.

7. A fluid dispenser comprising:
   a barrel having a reservoir chamber, the barrel having an upper portion and a lower portion;
   a cap located on top of the upper portion of the barrel and connected to the reservoir chamber, the cap having an external surface with at least one hole therethrough;
   a valve comprising a single-piece umbrella-shaped valve having a biasing portion, a stem and a seal located in the cap hole, the valve being located at the point where a downward force is applied against the cap;

a coupler having a dispense chamber, the coupler being coaxial with the barrel and wherein the barrel lower portion moves into the dispense chamber during dispensing of fluid; and a vent located between the cap and the reservoir chamber, the vent including a vent opening and a vent material composed of oliophobic material.

8. The fluid dispenser of claim 7 wherein the valve is inserted through the cap hole, oriented with the biasing member contacting the external surface of the cap, and the hole sealer located in and in sealing relation to the hole.

9. The fluid dispenser of claim 7 wherein the hole sealer is a bulge substantially spherical in shape.

10. The fluid dispenser of claim 7 wherein the external cap surface further comprises a raised surface that mates with the biasing portion of the valve.

11. The fluid dispenser of claim 10 wherein the raised surface further comprises breaks in the raised surface that function as air passageways.

12. A fluid dispenser comprising:

a barrel having a reservoir chamber, the barrel having upper and lower portions;

a cap located on top of the upper portion of the barrel and connected to the reservoir chamber, the cap having an external surface with at least one hole therethrough, said cap further comprises a raised surface on the cap external surface that mates with the biasing portion of the valve;

a valve comprising a biasing member and a hole sealer, the valve being located in the hole in the cap at the point where a downward force is applied against the cap;

a coupler having a dispense chamber, the coupler being coaxial with the barrel and wherein the barrel lower portion moves into the dispense chamber during dispensing of fluid; and a vent located between the cap and the reservoir chamber, the vent including a vent opening and a vent material composed of oliophobic material.

13. The fluid dispenser of claim 12 wherein the valve is oriented with the biasing member contacting the external surface of the cap, and the hole sealer located in and in sealing relation to the hole.

14. The fluid dispenser of claim 12 wherein the valve comprises a single-piece umbrella-shaped valve having a biasing portion, a stem and a seal located in the cap hole.

15. The fluid dispenser of claim 12 wherein the hole sealer is a bulge substantially spherical in shape.

16. The fluid dispenser of claim 12 wherein the raised surface further comprises breaks in the raised surface that function as air passageways.

* * * * *